(12) United States Patent
Chauhan et al.

(10) Patent No.: US 8,404,265 B2
(45) Date of Patent: Mar. 26, 2013

(54) CONTACT LENSES FOR EXTENDED RELEASE OF BIOACTIVE AGENTS CONTAINING DIFFUSION ATTENUATORS

(75) Inventors: Anuj Chauhan, Gainesville, FL (US); Jinah Kim, Midlothian, VA (US)

(73) Assignee: University of Florida Research Foundation, Inc., Gainesville, FL (US)

(*) Notice: Subject to any disclaimer, the term of this patent is extended or adjusted under 35 U.S.C. 154(b) by 110 days.

(21) Appl. No.: 12/841,504

(22) Filed: Jul. 22, 2010

(65) Prior Publication Data

US 2010/0330146 A1  Dec. 30, 2010

Related U.S. Application Data

(63) Continuation-in-part of application No. PCT/US2009/031714, filed on Jan. 22, 2009.

(60) Provisional application No. 61/073,141, filed on Jun. 17, 2008, provisional application No. 61/011,860, filed on Jan. 22, 2008.

(51) Int. Cl.
*A61K 31/5377* (2006.01)
*A61K 31/4196* (2006.01)
*A61K 31/573* (2006.01)
*A61P 27/02* (2006.01)
*A61P 29/00* (2006.01)
*A61P 27/06* (2006.01)
*A61P 31/00* (2006.01)

(52) U.S. Cl. ......... 424/424; 424/427; 424/429; 514/458

(58) Field of Classification Search .............. 351/160 H; 424/427, 429; 510/112; 526/320
See application file for complete search history.

(56) References Cited

U.S. PATENT DOCUMENTS

| | | | |
|---|---|---|---|
| 6,387,379 B1 | 5/2002 | Goldberg et al. | |
| 2006/0008506 A1* | 1/2006 | Cipriano De Sousa et al. | 424/427 |
| 2006/0100408 A1* | 5/2006 | Powell et al. | 526/320 |
| 2007/0296914 A1* | 12/2007 | Hong et al. | 351/160 H |
| 2008/0094573 A1 | 4/2008 | Vermette et al. | |
| 2009/0060981 A1 | 3/2009 | Chauhan | |

* cited by examiner

*Primary Examiner* — Walter Webb
(74) *Attorney, Agent, or Firm* — Saliwanchik, Lloyd & Eisenschenk

(57) ABSTRACT

An appliance for the delivery of at least one bioactive agent to the eye has at least one diffusion attenuator within a hydrophilic or silicone-hydrogel contact lens. The bioactive agent can be a drug or a nutraceutical. The diffusion attenuator can be a plurality of solid particles or phase separated liquid aggregates within at least one continuous phase of the lens where the diffusion attenuators promote a tortuous path for the diffusion of the bioactive agent to mediate the rate by which the bioactive agent diffuses from the contact lens. The diffusion attenuator can be homogeneously dispersed throughout at least one continuous phase of the lens to modify the diffusivity of the bioactive agent through that phase. The diffusion attenuator can have little or no affinity for the bioactive agent or can be miscible with the bioactive agent. The diffusion attenuator can be incorporated while forming the contact lens by polymerization of a monomer mixture containing the diffusion attenuator. For liquid diffusion attenuators, the liquid can be co-absorbed with a solvent into the lens followed by removal of the solvent, where the bioactive agent can be co-absorbed or subsequently absorbed after the loading of the diffusion attenuator. The diffusion attenuator can be Vitamin E.

17 Claims, 51 Drawing Sheets

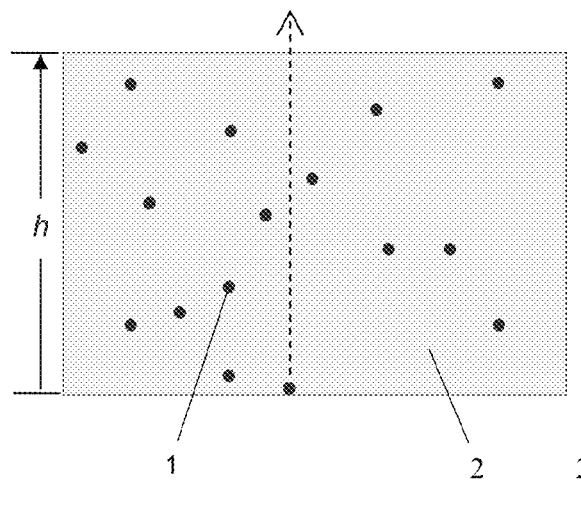
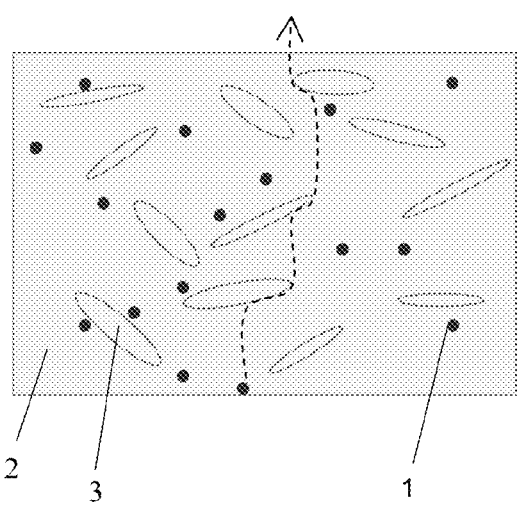
FIG. 1A  FIG. 1B
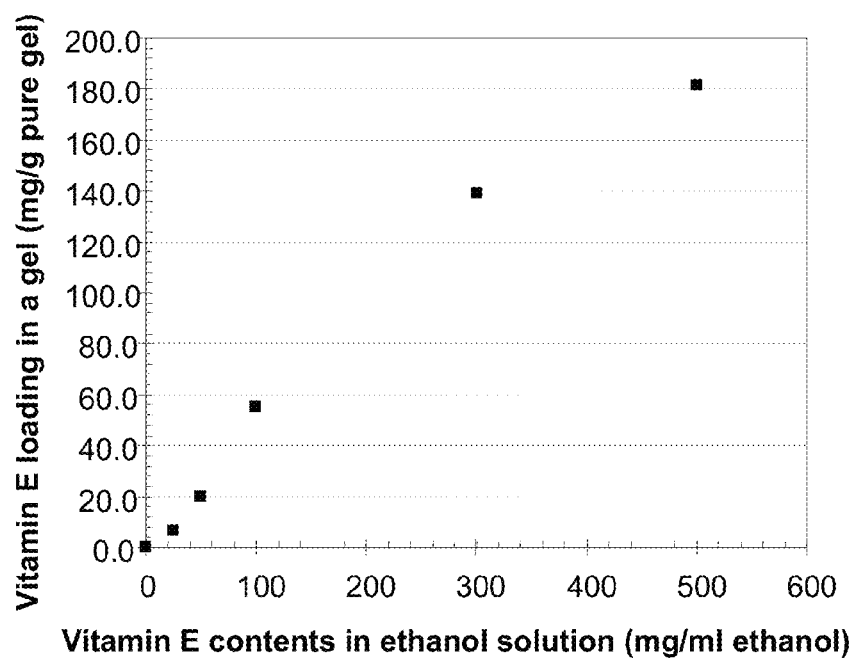
FIG. 2

CONTACT LENSES FOR EXTENDED RELEASE OF BIOACTIVE AGENTS CONTAINING DIFFUSION ATTENUATORS

CROSS-REFERENCE TO RELATED APPLICATIONS

This application is a continuation-in-part of International Patent Application No. PCT/US2009/031714, filed Jan. 22, 2009, which claims the benefit of U.S. Provisional Application No. 61/073,141, filed Jun. 17, 2008, and U.S. Provisional Application No. 61/011,860, filed Jan. 22, 2008, the disclosures of which are hereby incorporated by reference in their entireties, including any figures, tables, or drawings.

BACKGROUND OF THE INVENTION

Providing and maintaining adequate concentrations of bioactive agents, such as drugs, in the pre-corneal tear film for extended periods of time is one of the major problems plaguing methods and systems for ocular drug delivery. The delivery of such bioactive agents from a contact lens has been examined. This dosage form generally suffers from a phenomena known as burst release, where most or all of the agent is released in a very short period of time after placing the contact lens in the eye, with only a negligible release over longer periods of time. An important contact lens material is a silicone hydrogel, which is a material that is employed for extended wear lenses that can be used for periods up to about a month. Hence, the development of methods and contact lens appliances, where the release of a drug occurs over an extended period of time, is attractive.

The release of a bioactive agent or any other compound from a contact lens is ultimately controlled by diffusion within the lens material. For a diffusion controlled process, the duration of release can be approximately calculated by $l^2/D$, where l is the path length that a compound needs to traverse and D is the molecular diffusivity. For a typical contact lens, l is the thickness of the lens, which varies in the radial direction but is on average approximately 100 microns for a typical lens. The period of time over which a drug is released from a contact lens can be increased by either increasing l or by decreasing D. In most diffusion controlled systems, augmentation of diffusivity has been performed by changing the bulk material to one of a different diffusivity. However, because of the strict requirements of a contact lens where many material properties can not be compromised, there are practical limits to the selection of the bulk material. Furthermore, an effective strategy to modifying the diffusion process must be applicable to a wide range of bioactive agents with a similar bulk material.

One approach to the control of molecular diffusion in contact lenses has been disclosed by Qiu et al., U.S. Pat. No. 6,827,996 where a diffusion-controllable coating is placed on the surface of a lens. The method involves the deposition of one or more layers of a diffusion barrier on the surface of a lens. Deposition of a thin film on the surface can alter the surface properties, such as wettability, protein binding, and lubricity, which can have undesirable consequences. A single layer may not be sufficient to significantly alter the drug transport unless it is very thick, which can adversely impact transparency and mechanical properties. Construction of multiple layers complicates the fabrication process. Also, if the swelling of the deposition thin film differs from that of the bulk material, the shape of the coated contact lens can be altered from that of the uncoated lens making the process of lens design iterative and complicated. Although the need and statement of intent to control the release of drugs is disclosed, examples are provided only for preventing release of an agent and toward preparation of lenses that do not require an extraction process to remove monomers and other compounds involved in the formation of the lens.

An approach that attenuates drug release properties without impacting surface properties is desirable. Hence a method to modify the delivery of a bioactive agent from a lens remains a target in the development of a contact lens dosage form for bioactive agents.

BRIEF SUMMARY OF THE INVENTION

Embodiments of the invention are directed to an appliance for the delivery of a bioactive agent to a patient where the appliance is a hydrophilic or silicone-hydrogel lens within which is incorporated diffusion attenuators. Bioactive agents can be drugs and/or nutraceuticals. Among the drugs that can be included are: dexamethasone (DX), dexamethasone 21-disodium phosphate (DXP), ketotifen fumarate (KF), timolol maleate, and fluconazole; and can be used in their ionic or non-ionic form. The diffusion attenuator can be any combination of a liquid that modifies the molecular diffusivity, D, of the lens material or a plurality of phase separated liquid aggregates or solid particles dispersed to act as barriers to the diffusion of one or more bioactive agents included within the lens. As a diffusion barrier the path length, l, is changed from that of the unmodified lens.

In embodiments where the diffusion modifier acts as diffusion barriers the liquid or solid particles need not absorb the agents, but can cause the path of the agent during release to deviate from that of a short direct diffusion pathway to a tortuous pathway. Solid particles can be polymers, silica, glass, and inorganic crystals of appropriate size or refractive index to allow the maintenance of the optical clarity of the lens. When the particle is a polymer, it can be immiscible with all polymeric materials of the lens or it can be a copolymer similar to that of the lens but differs in composition by the proportions of comonomers or the cross-linking density of the lens. As these polymers are cross-linked, they do not dissolve into the lens and remain a discrete structure. These particles can be asymmetric in shape, for example discs, plates, rods, flakes, or spheroids can be employed. Additionally, these asymmetric shapes can be oriented and not simply dispersed with a random orientation in the lens. A liquid phase barrier can result from a liquid that is immiscible in the lens and can segregate within any of multiple phases of a lens or can partition to the interface between phases of a lens. A surface active agent can be included to stabilize the interface of the liquid barrier and the lens materials. Liquids that can act as the barrier include Vitamin E, Vitamin A, silicone oils, or hydrocarbon oils.

An embodiment of the invention involves a method of preparation of a contact lens containing at least one liquid diffusion attenuators for delivery of a bioactive agent. The method involves providing a hydrophilic or silicone-hydrogel lens which is subsequently: soaked in a solution of at least one diffusion barrier forming liquid: soaked in a solution having at least one bioactive agent: and subsequently removing one or more solvents. The non-aqueous solvent ethanol is among useful solvents for preparing the desired lenses.

Another embodiment of the invention is directed to a method of preparation for a contact lens containing diffusion attenuators where a monomer mixture having included at least one liquid or a plurality of solid diffusion attenuators is formed into a lens by polymerizing the monomer mixture. The lens is then soaked in a solution of the bioactive agent or agents and removed from the solution. The particle can be mixed into the lens monomers by mechanical or hydrosonic mixing of the diffusion barriers into a polymerization mixture.

Another embodiment of the invention is a method of delivering a bioactive agent to an eye where a hydrophilic or silicon-hydrogel contact lens with at least one bioactive agent and containing at least one diffusion attenuator dispersed therein is placed into an eye. The lens can deliver the bioactive agent for a period of time of 8 hours or more.

BRIEF DESCRIPTION OF THE DRAWINGS

FIGS. 1A-1B are a schematic drawing illustrating a mechanism of attenuation of drug release rates from contact lenses by using diffusion barriers according to an embodiment of the invention.

FIG. 2 shows a plot of the maximum concentration of Vitamin E taken up by the contact lens as a function of the concentration of Vitamin E in ethanol.

Figure 25A:
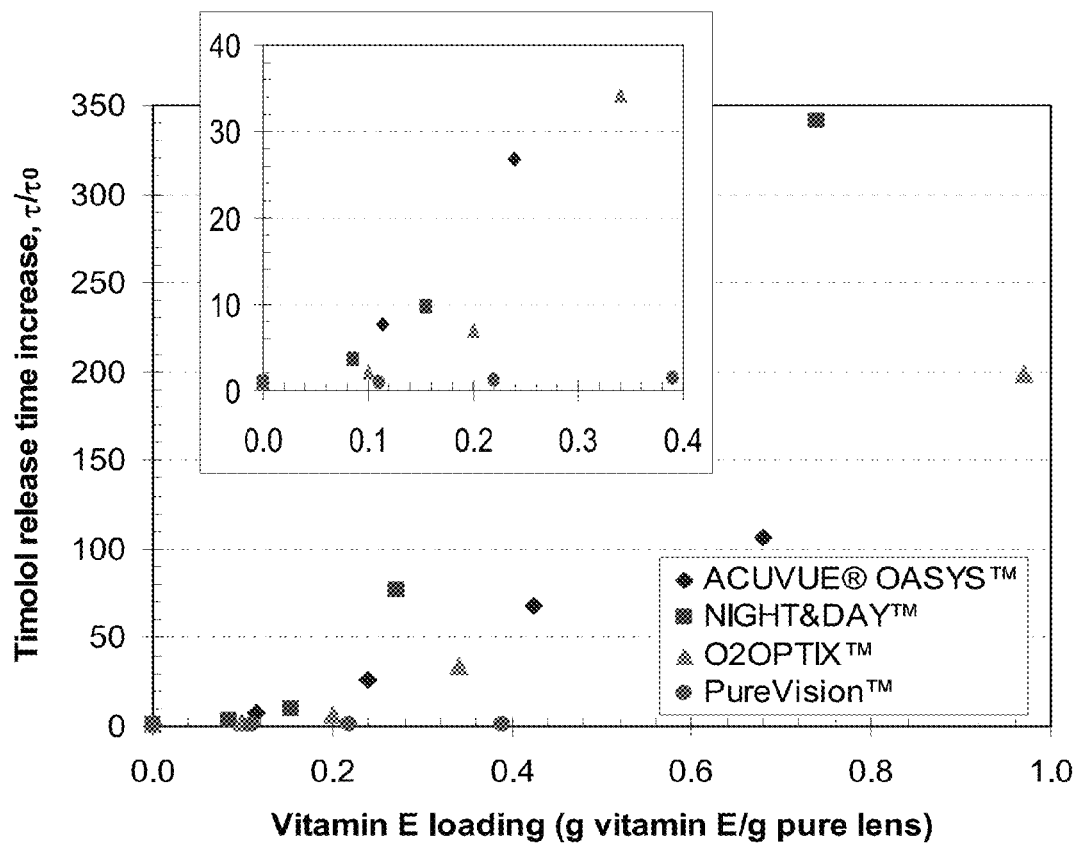
Figure 25B:
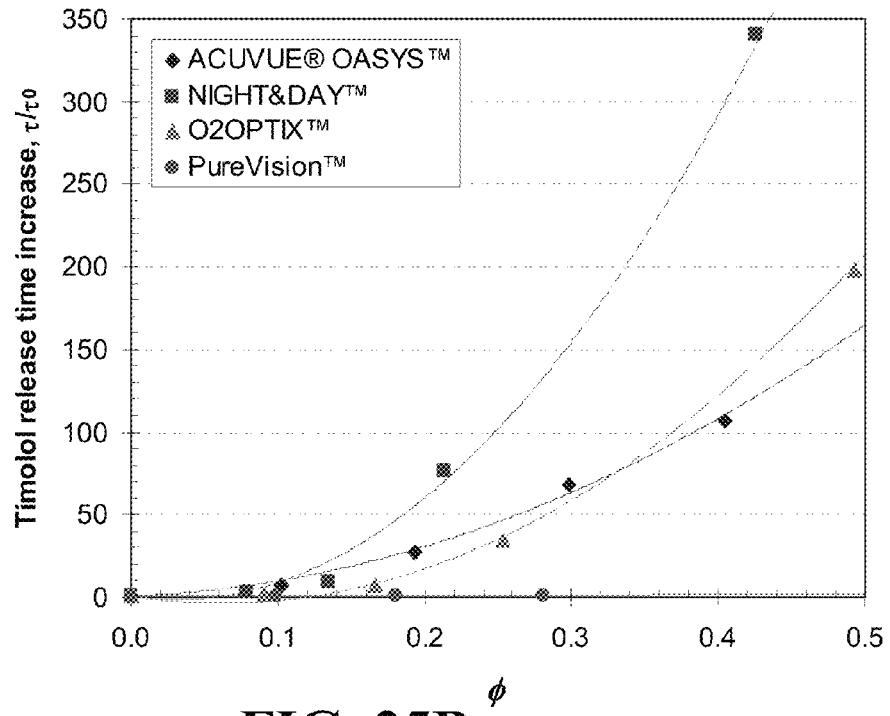

FIGS. 25A-25B shows plots of the timolol release duration difference for various commercial contact lenses for A) various loadings of Vitamin E and B) various volume ratios, φ, of Vitamin E in the dry lenses where lines in B) are best fit $2^{nd}$ order polynomial curves and the insert in A) is for low Vitamin E loadings to data of each lens and where the identity of the lenses is given in the legend.

Figure 26A:
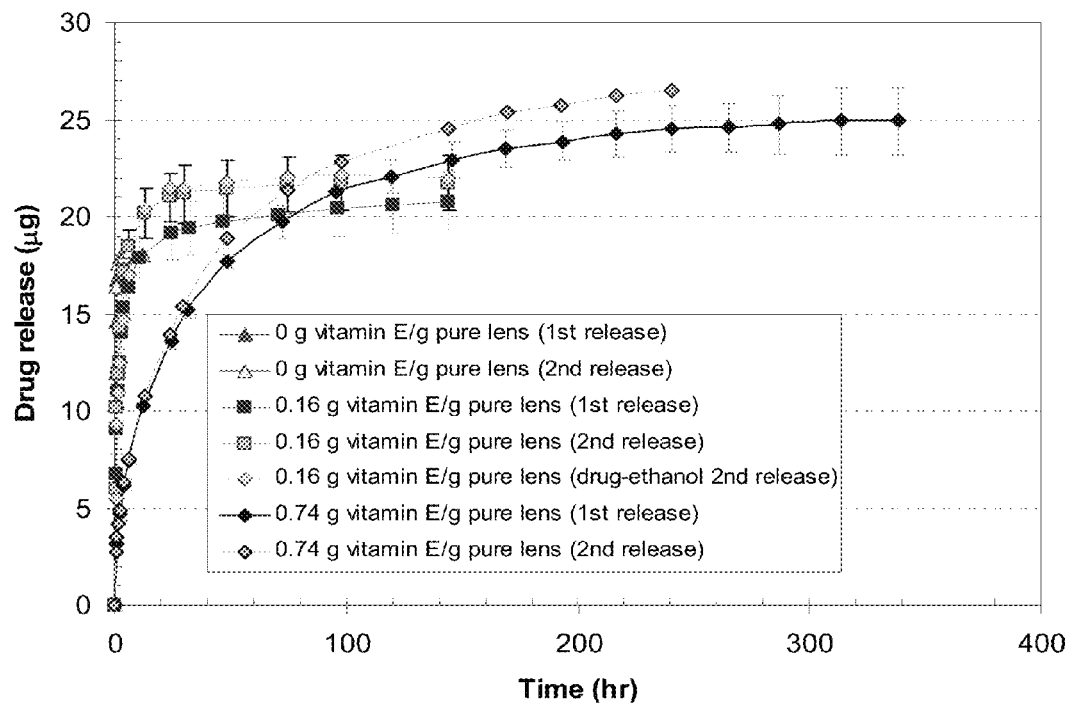
Figure 26B:
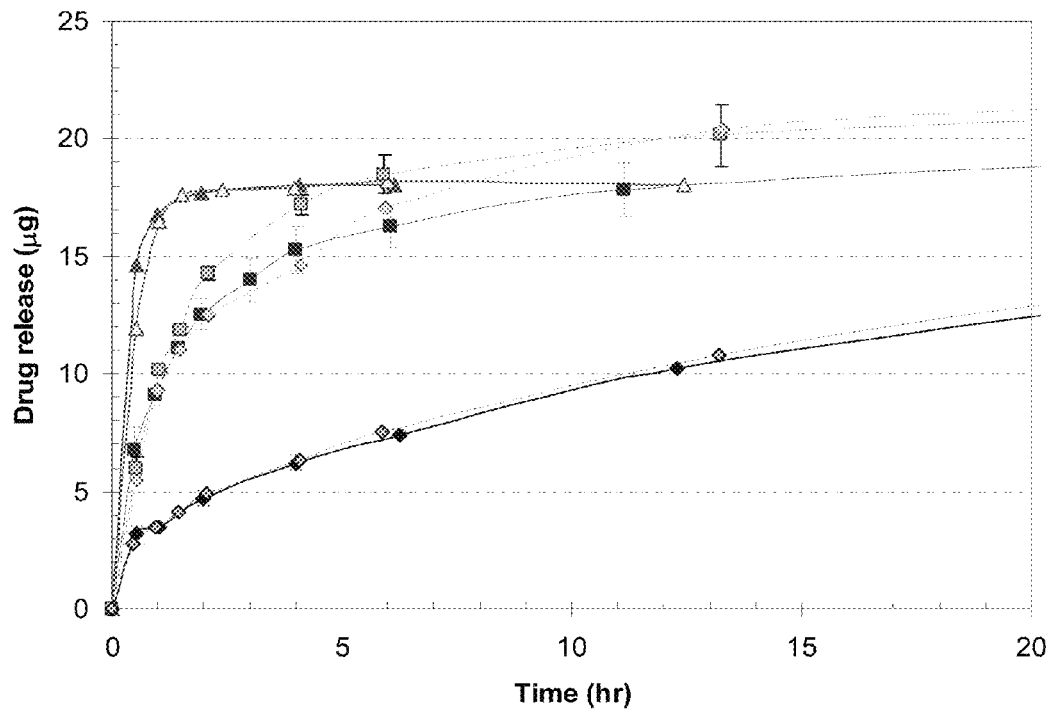
Figure 27A:
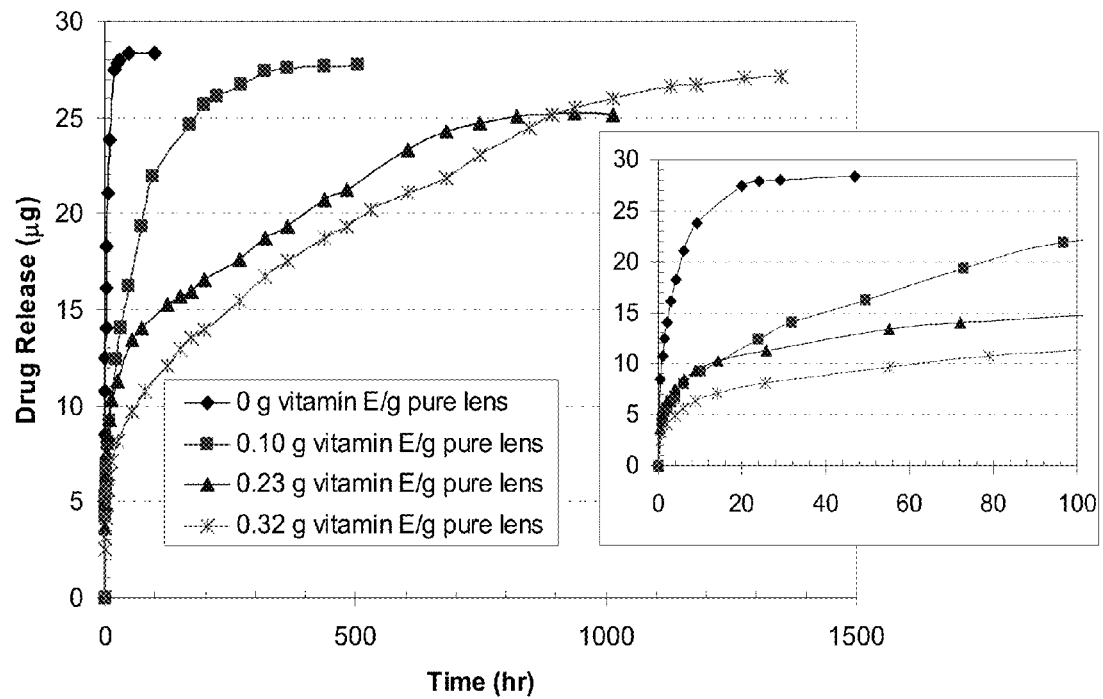
Figure 27B:
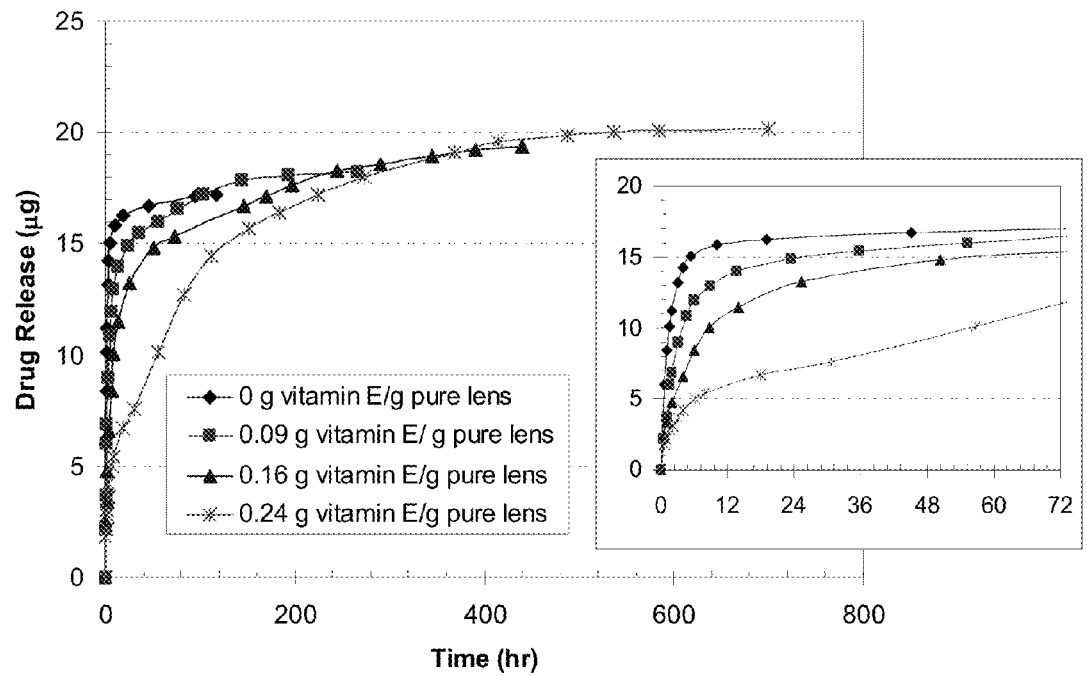
Figure 27C:
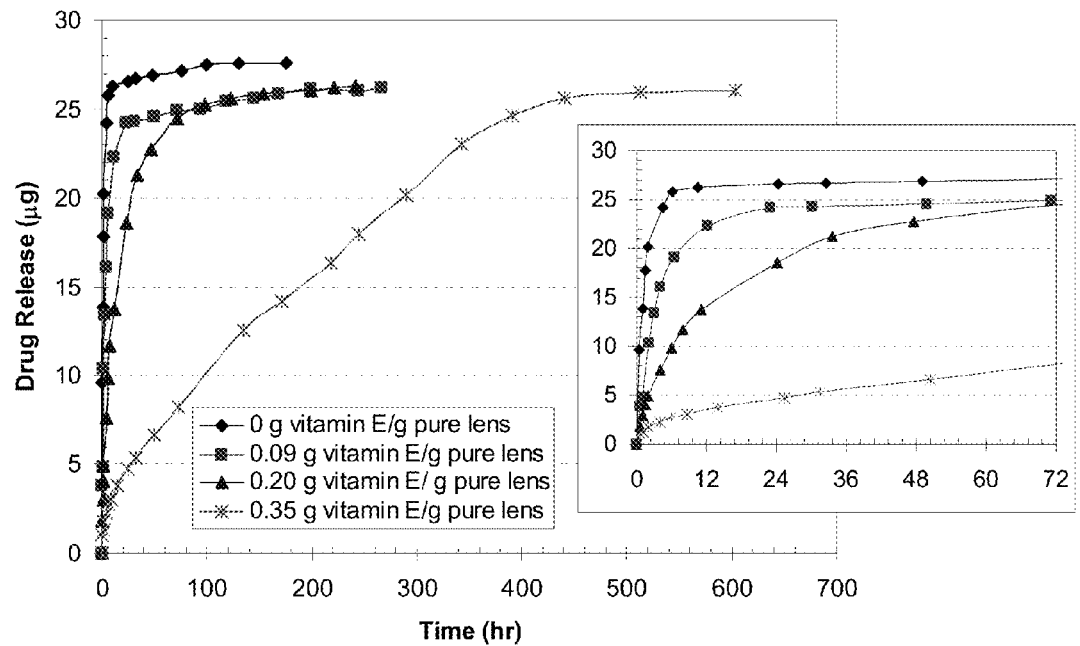
Figure 27D:
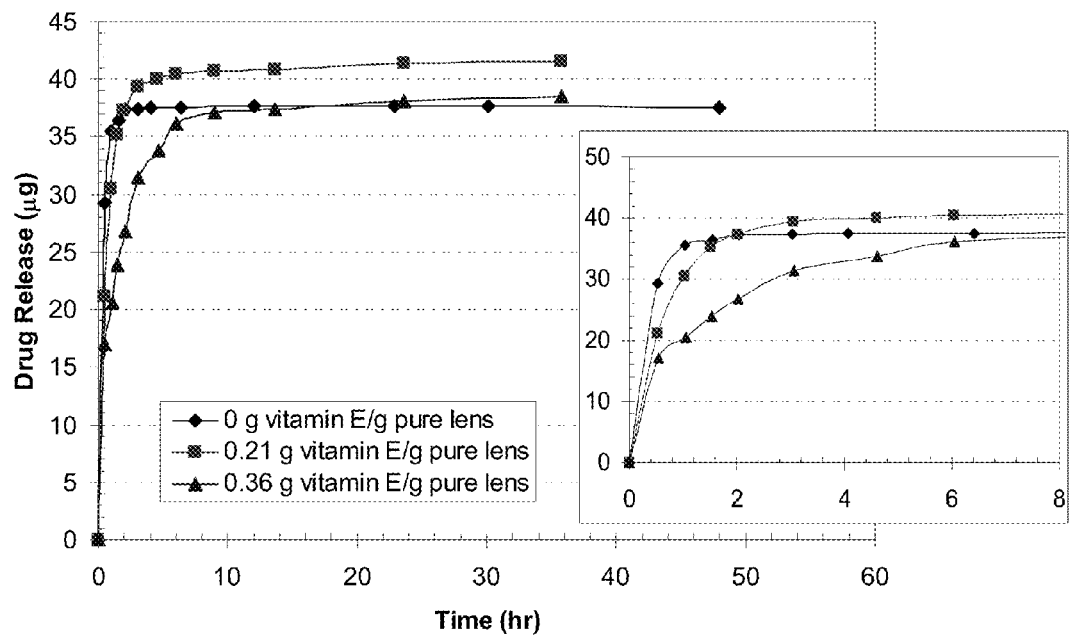
Figure 28A:
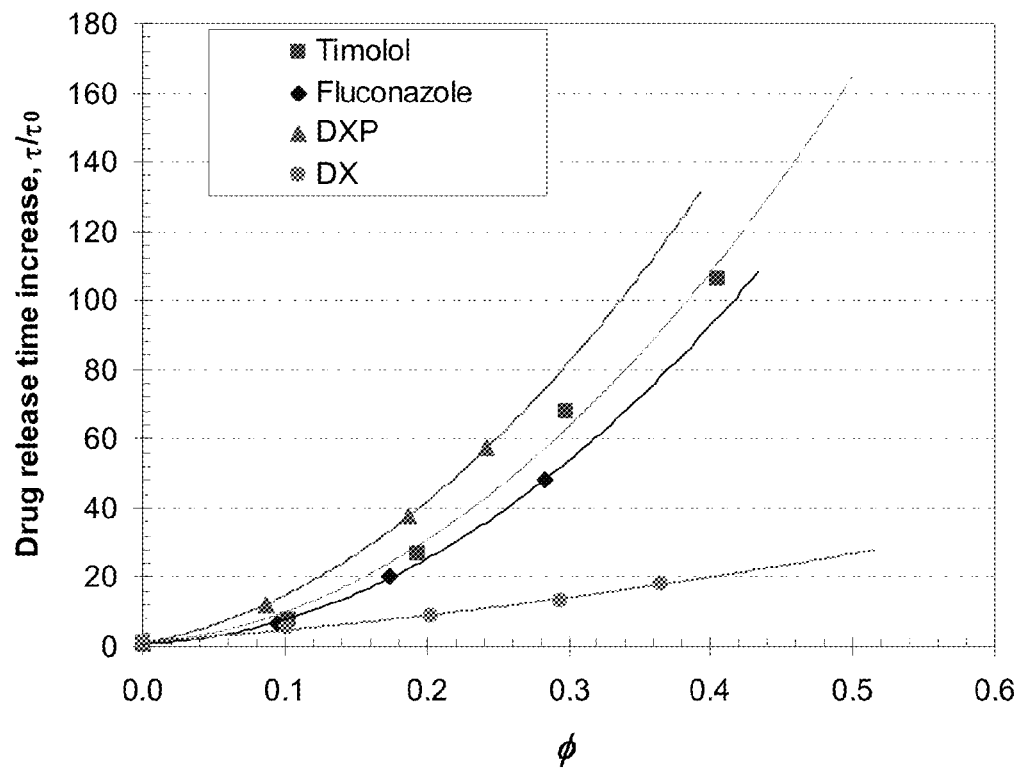
Figure 28B:
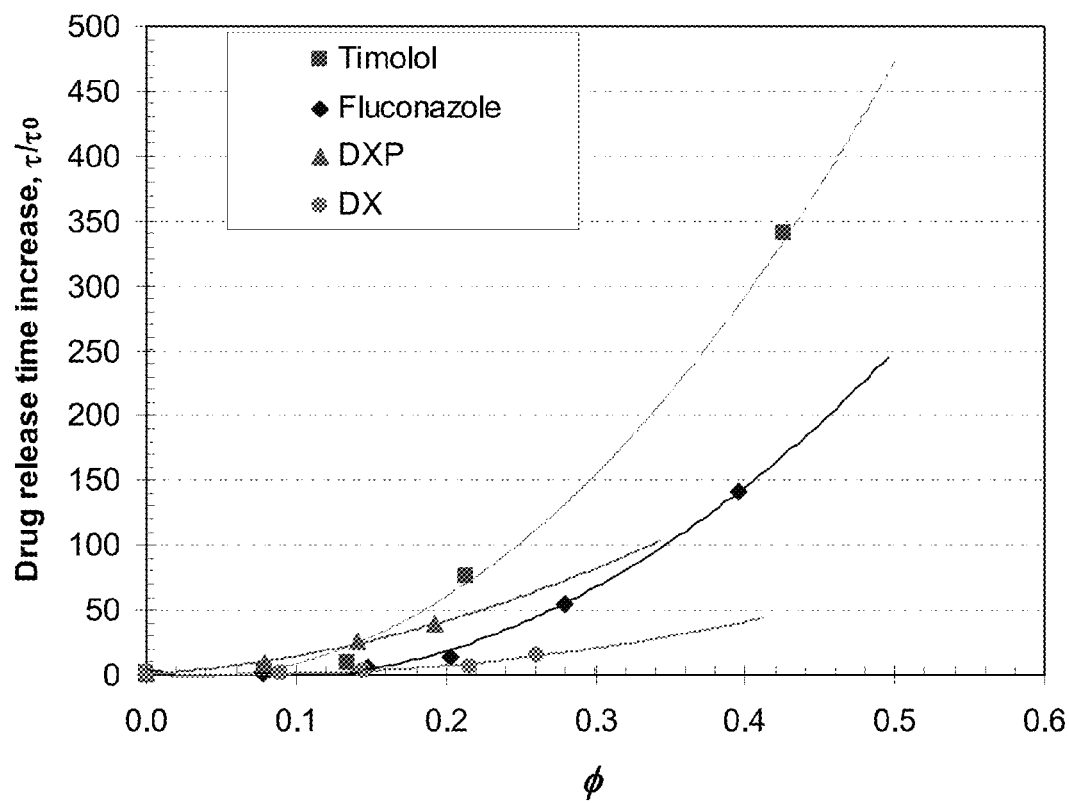
Figure 28C:
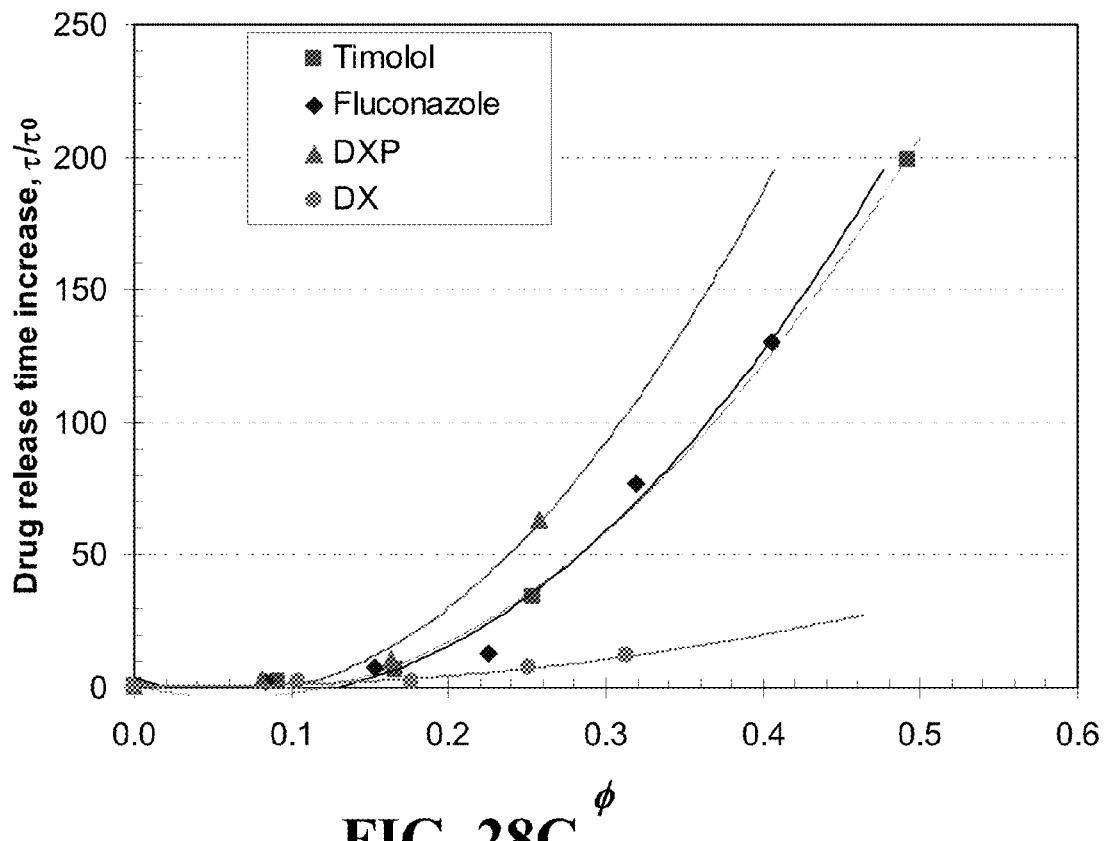
Figure 28D:
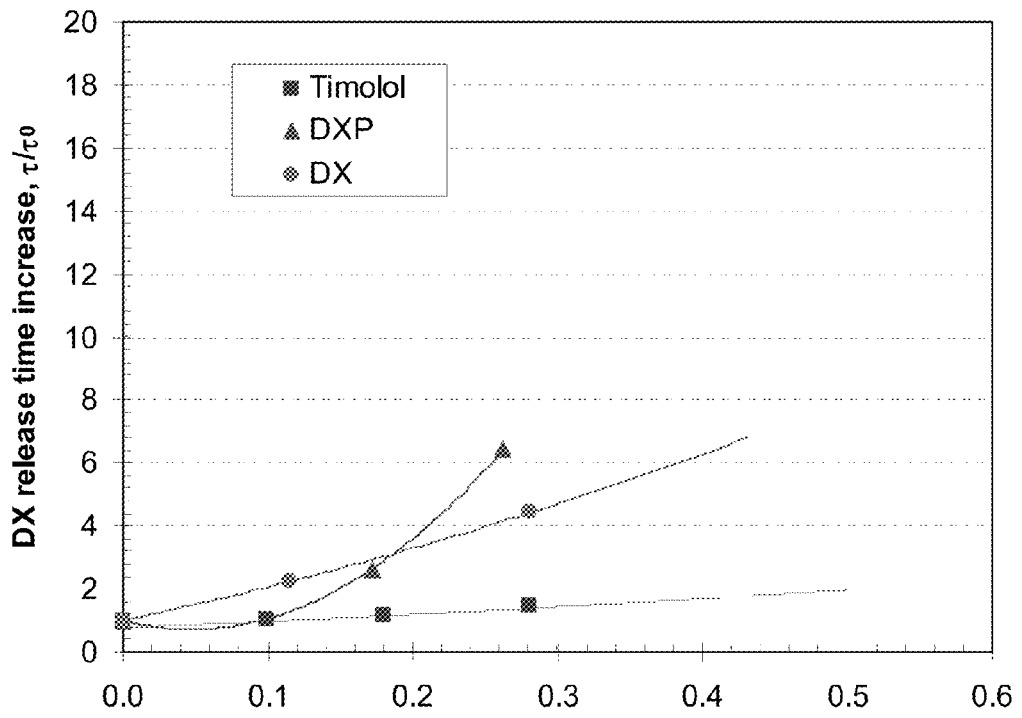

FIGS. 26A-26B shows plots of timolol release by Vitamin E loaded versus time for the second releases of timolol from a reused Vitamin E loaded lens loaded by soaking in a timolol-PBS solution (0.8 mg/ml) for 7 days for the Vitamin E loadings indicated in the legend over long times A) and the initial 20 hours B).

FIGS. 27A-27D shows plots of DXP release by Vitamin E loaded A) ACUVUE® OASYS™, B) NIGHT&DAY™, C) $O_2$OPTIX™, and D) PureVision™ lenses versus time where lenses were soaked in a Vitamin E-ethanol solution, dried and soaked in a DXP-PBS solution (0.7 mg/ml) for the Vitamin E loadings indicated in the legend where the inserts plot the initial release.

FIGS. 28A-28D shows plots of the release duration difference from Vitamin E free lenses for various drugs from A) ACUVUE® OASYS™, B) NIGHT&DAY™, C) $O_2$OPTIX™, and D) PureVision™ contact lenses versus the volume ratios, φ, of Vitamin E in the dry lenses where the lines are best fit $2^{nd}$ order polynomial curves and the drug is indicated in the legends.

Figure 29A:
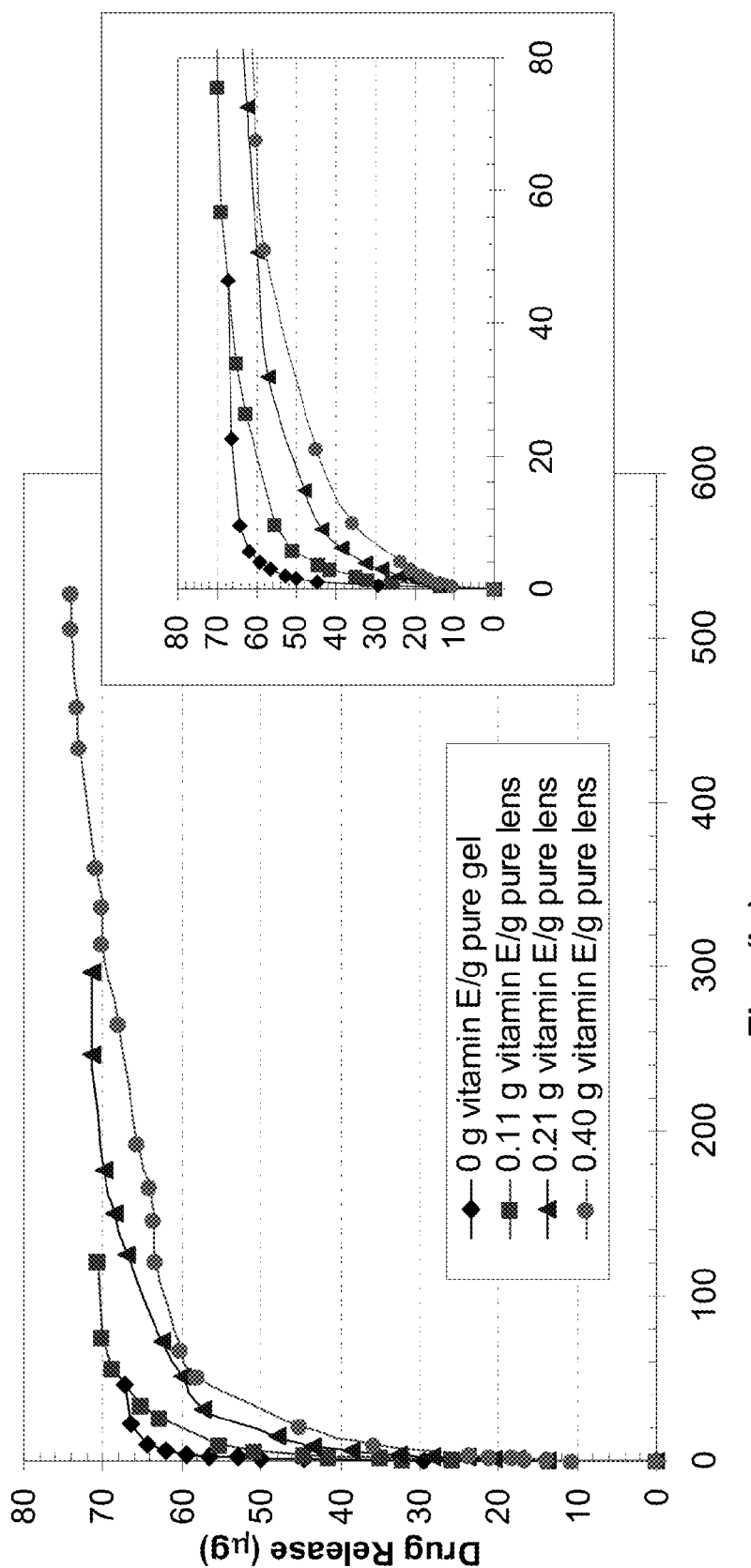
Figure 29B:
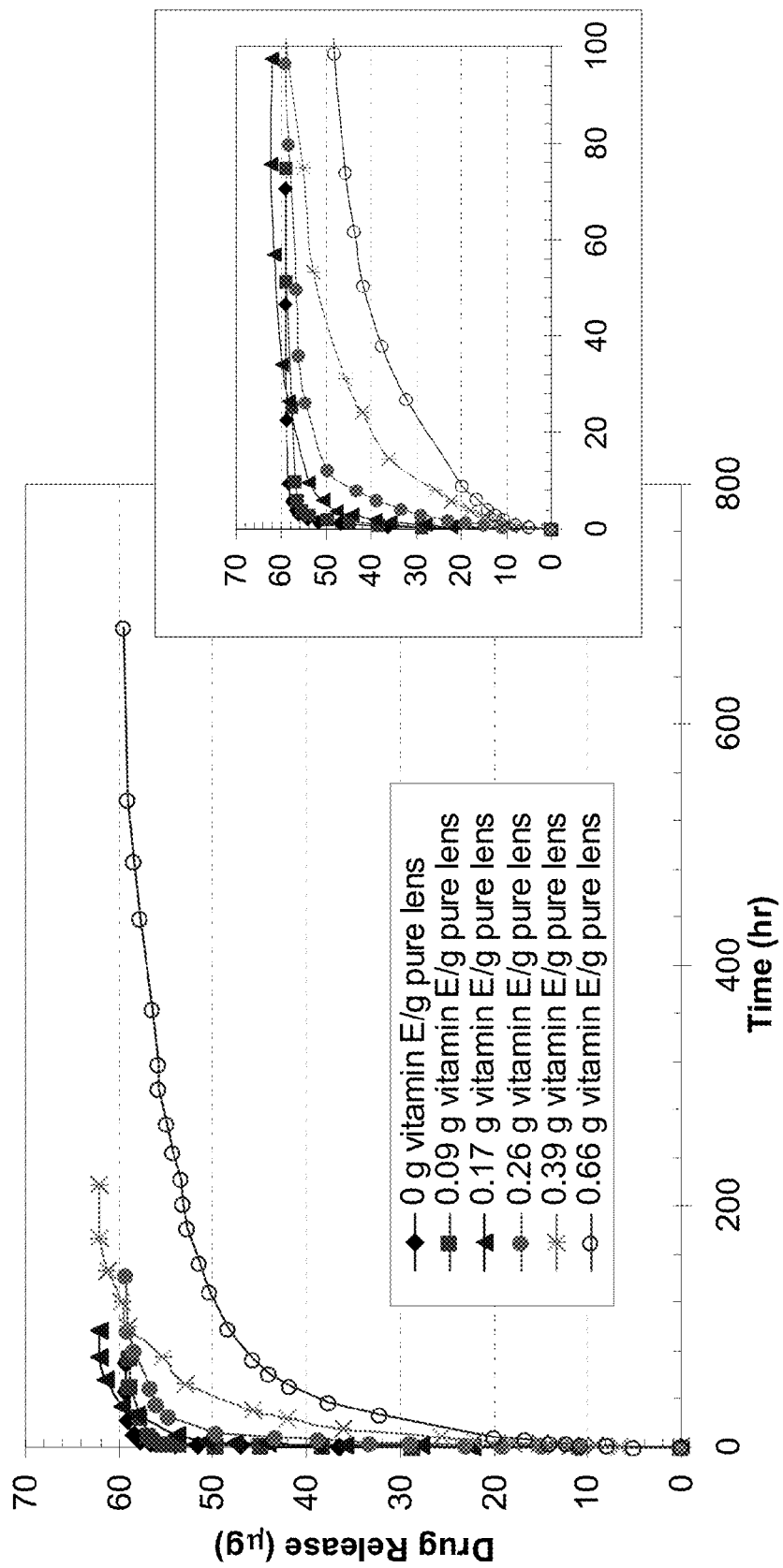
Figure 29C:
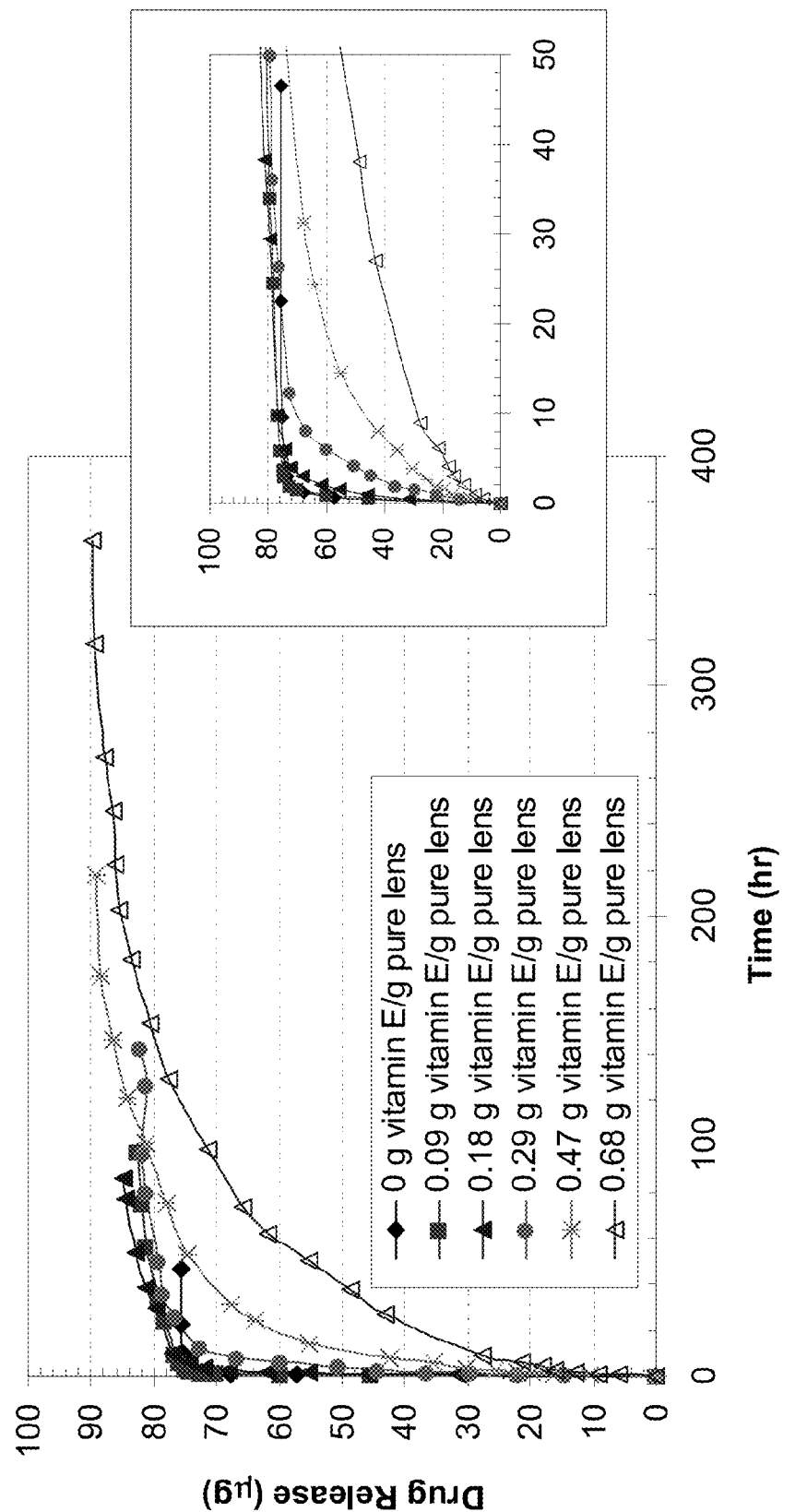

FIGS. 29A-29C shows plots of fluconazole (FCZ) release from Vitamin E loaded A) ACUVUE® OASYS™, B) NIGHT&DAY™, and C) $O_2$OPTIX™ versus time for lenses loaded by soaking in a Vitamin E-ethanol solution, dried, and soaked in a FCZ-PBS solution (0.7 mg/ml) for the Vitamin E loadings indicated in the legend and where the inserts plot the initial release.

Figure 30A:
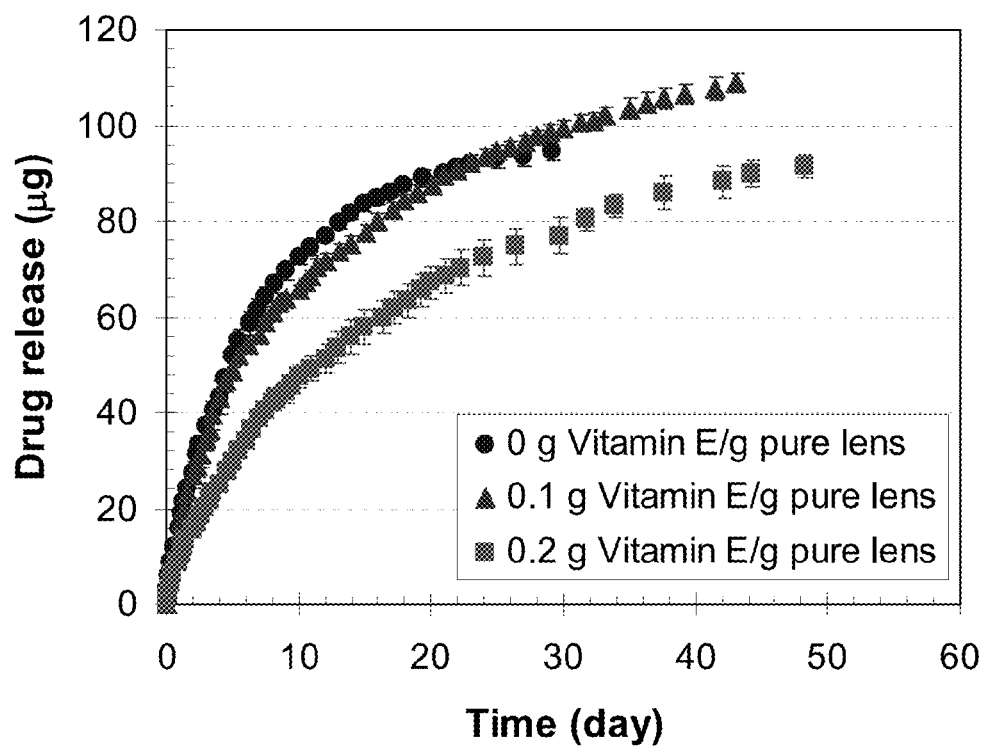
Figure 30B:
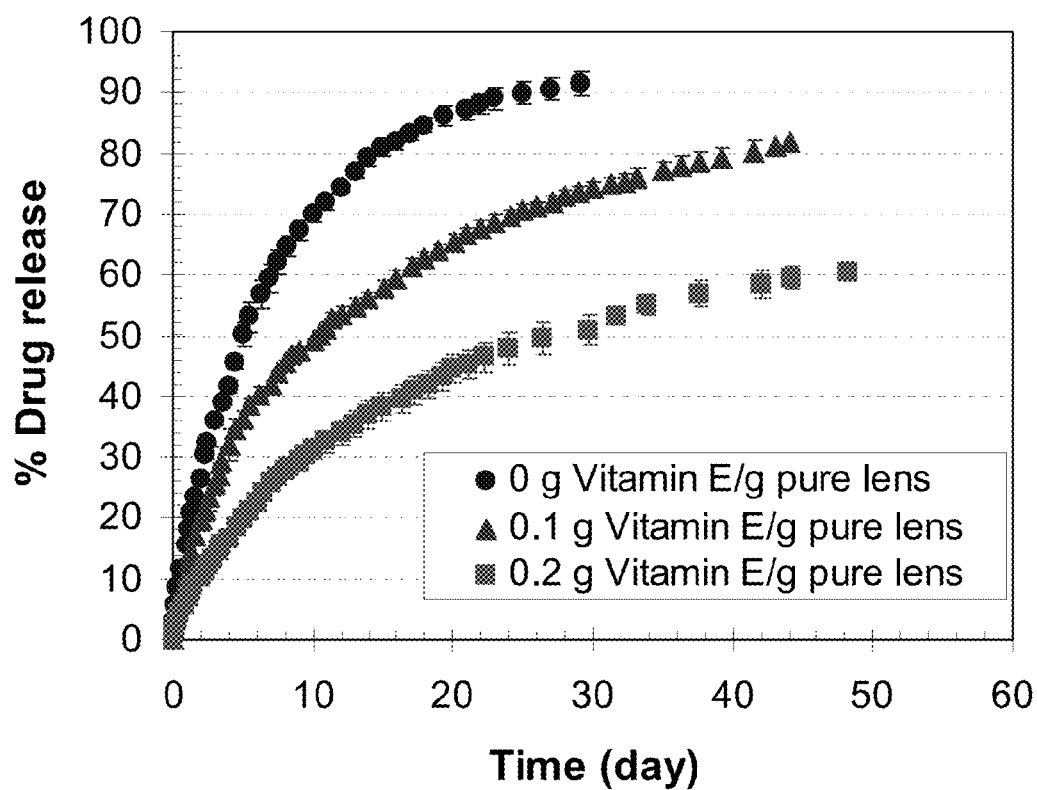

FIGS. 30A-30B shows CyA release profiles by Vitamin E loaded ACUVUE® OASYS™. Lenses were soaked in 10 ml of 17 µg/ml CyA/PBS solution for 30 to 60 days, and subsequently removed to 1.75 ml fresh PBS. Data were plotted as mean±SD (n=3).

FIGS. 31A-1 to 31D-3 shows plots of the % drug release by Vitamin E loaded lenses versus square root of time where lines are drawn for the best fit for short time data for the drugs A) DX, B) timolol, C) DXP, and D) fluconazole from 1) ACUVUE® OASYS™, 2) NIGHT&DAY™, 3) $O_2$OPTIX™ and 4) PureVision™ (where, for example, the plot A-1) is for the release of DX from ACUVUE® OASYS™) with $R^2$'s larger than 0.98 and where Vitamin E loadings are given in the legends.

FIGS. 32A-32D shows plots of the slopes of best fit straight line to the plot of A) % DX, B) % timolol, C) % DXP, and D) % fluconazole release versus square root of time for short periods of time by Vitamin E loaded lenses with $R^2$'s larger than 0.98 and the identity of the lens given in the legend.

Figure 33A:
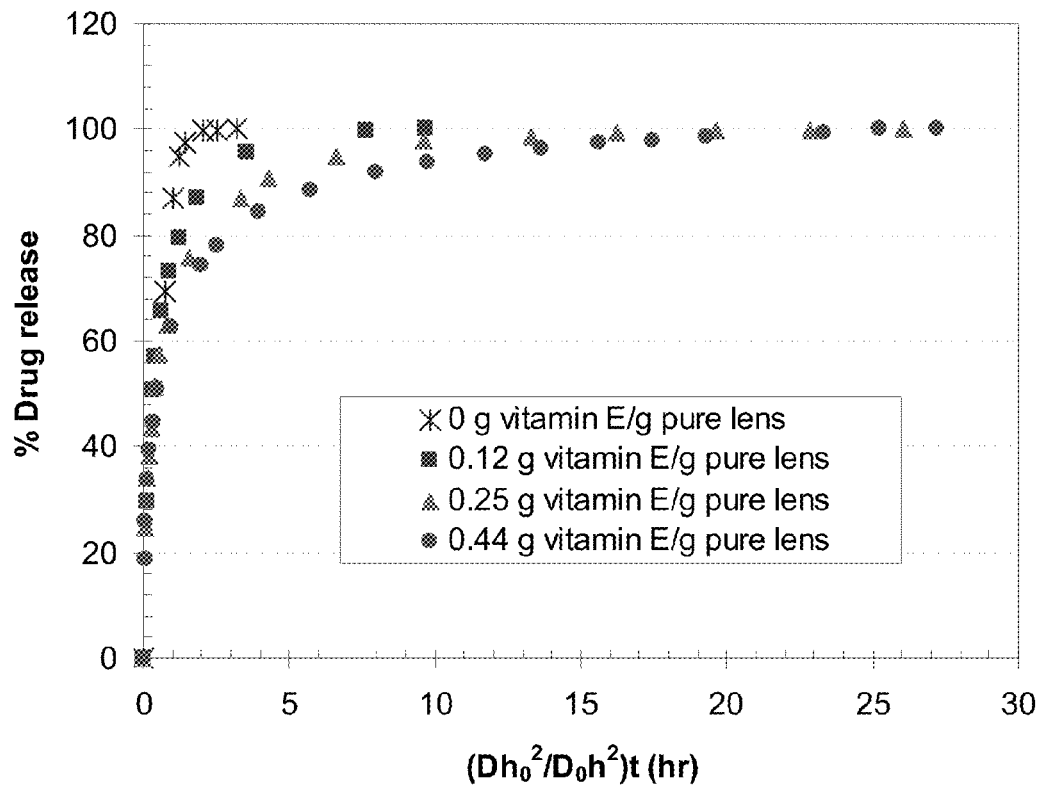
Figure 33B:
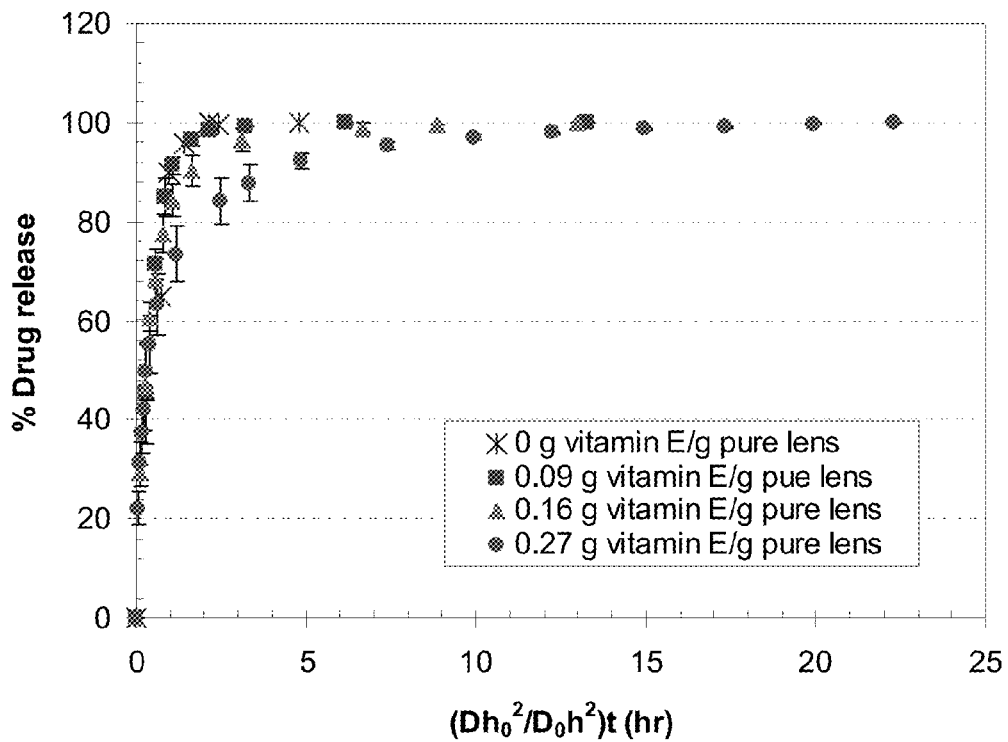

FIGS. 33A-33B shows plots of % drug release by vitamin loaded lenses versus $(Dh_0^2/D_0h^2)t$ for A) ACUVUE® OASYS™ and B) NIGHT&DAY™ contact lenses where the Vitamin E loadings are given in the legend.

Figure 34:
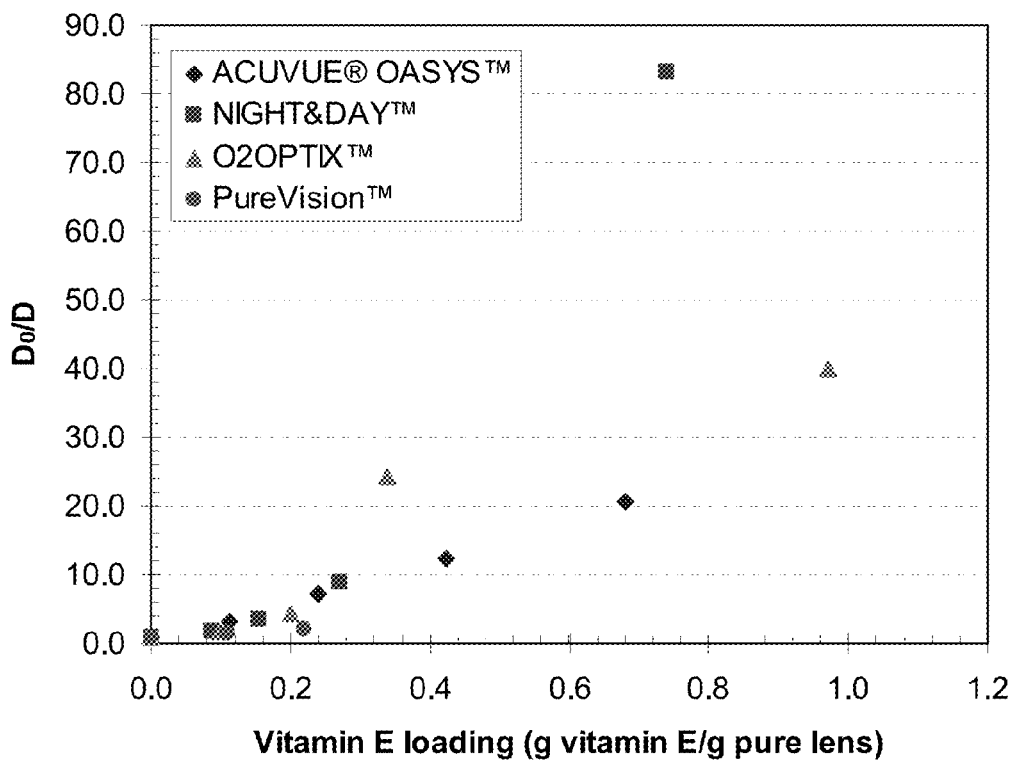

FIG. 34 shows a plot of $D_0/D$ versus Vitamin E loading for timolol release for the lenses given in the legend.

Figure 35:
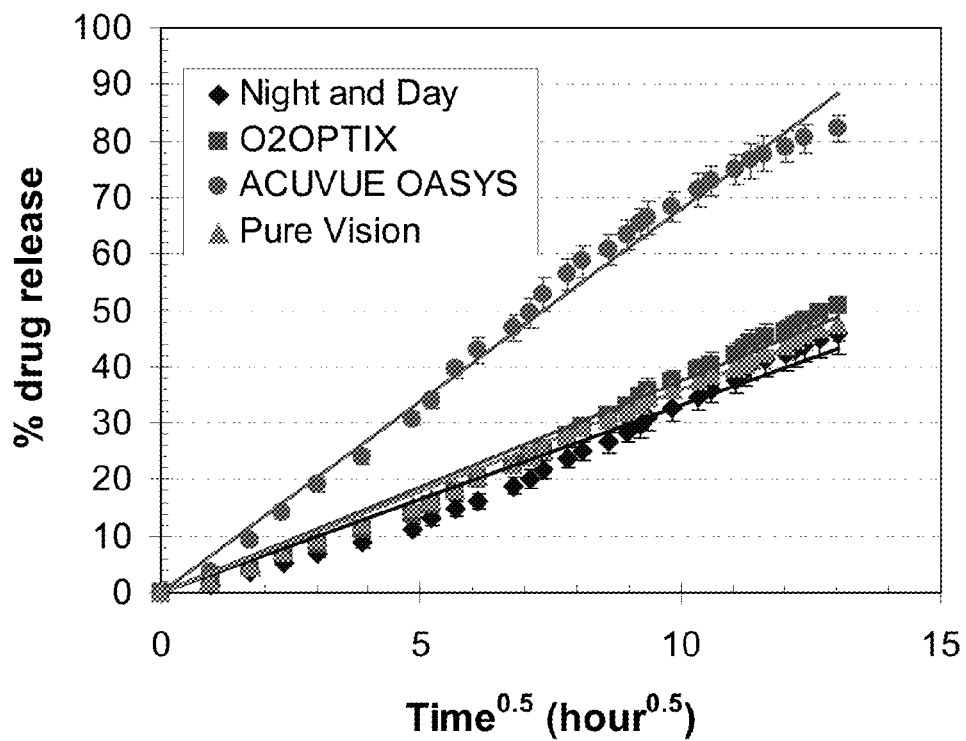

FIG. 35 shows a plot of % CyA release by silicone contact lenses versus square root of time. The lines are the best fit straight line. The fitted slope and $R^2$ are 6.7967 and 0.9908 for ACUVUE® OASYS™, 3.7416 and 0.9823 for $O_2$OPTIX™, 3.6036 and 0.9940 for PureVision™ and 3.3205 and 0.9660 for NIGHT&DAY™, respectively. Data are presented as mean±SD (n=3).

Figure 36:
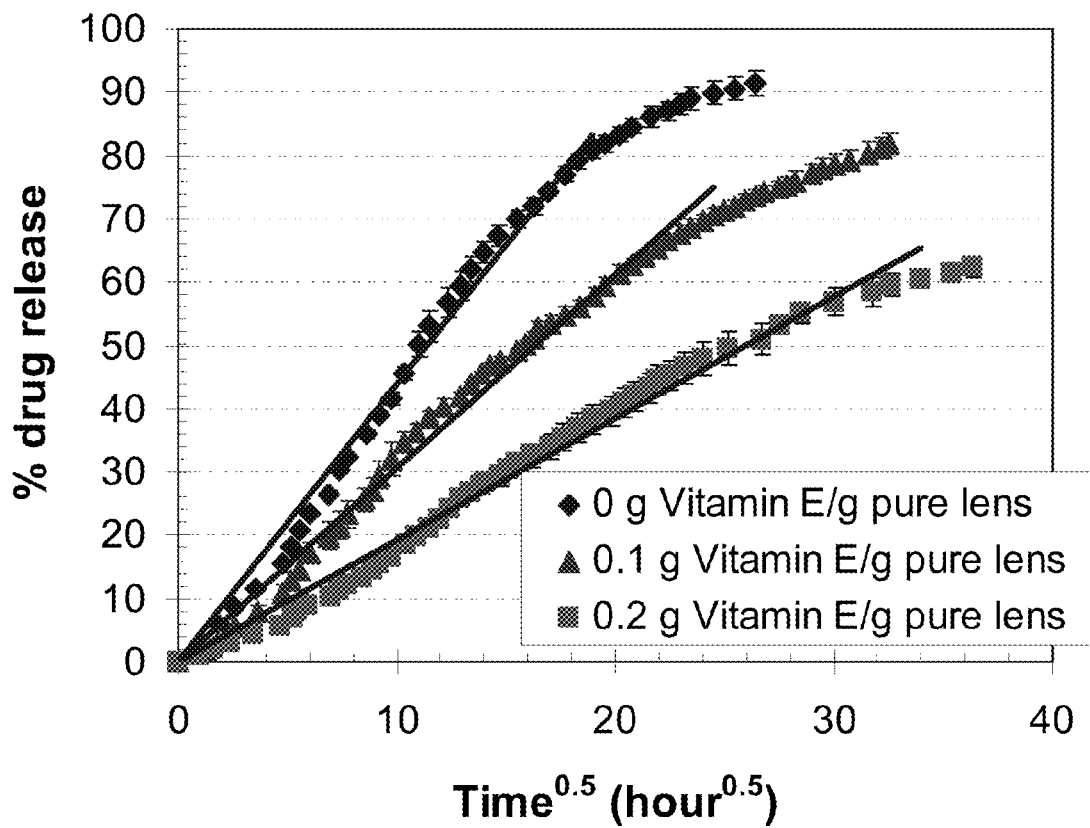

FIG. 36 shows a plot of CyA release by Vitamin E loaded ACUVUE® OASYS™ versus square root of time. The lines are the best fit straight line. The fitted slope and $R^2$ are 4.3901 and 0.9894, 3.0685 and 0.9891, 1.9404 and 0.9882 for lens with 0%, 10% and 20% of Vitamin E loading, respectively. Data are presented as mean±SD (n=3).

Figure 37:
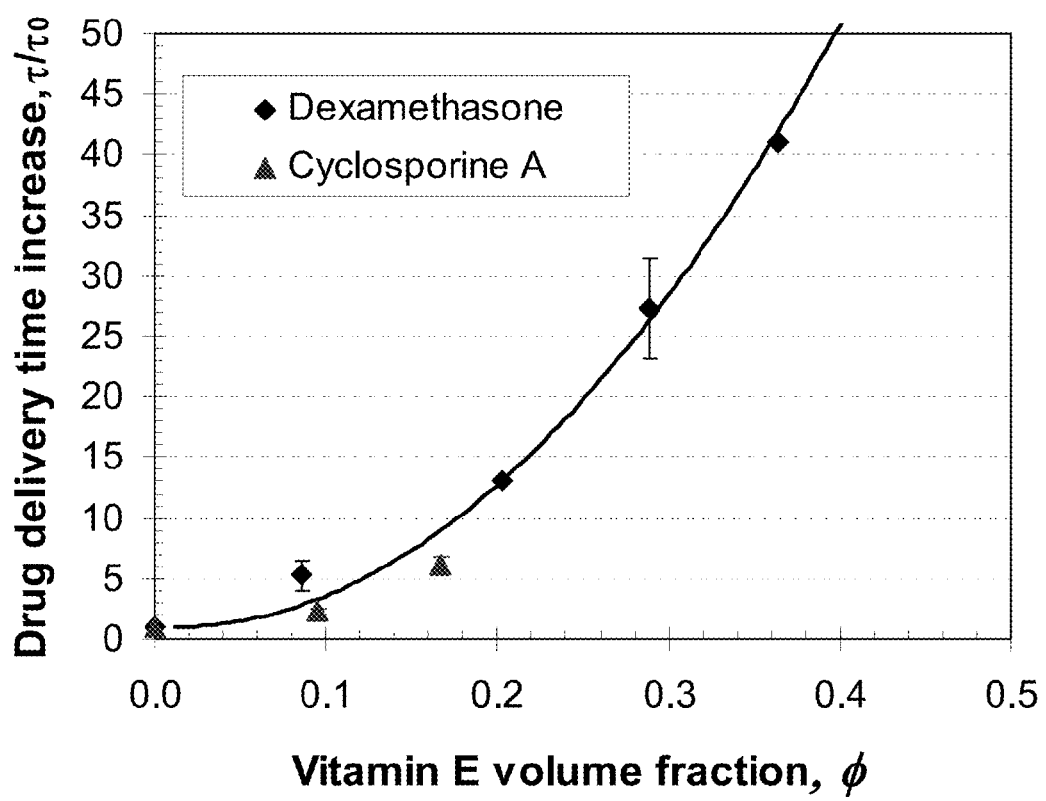

FIG. 37 shows the comparison of CyA and dexamethasone delivery by Vitamin E loaded ACUVUE® OASYS™.

DETAILED DESCRIPTION OF THE INVENTION

Embodiments of the invention are directed toward a method of controlling the diffusion of a bioactive agent in a contact lens matrix by the inclusion of a diffusion attenuator. In one embodiment the diffusion attenuator is included homogeneously or inhomogeneously through out the contact lens phase through which the bioactive agent diffuses to change the molecular diffusivity, D, of the bioactive agent in one or more phases in the contact lens. In another embodiment diffusion attenuators are diffusion barriers that are constructed or placed within the lens, such that an included bioactive agent is obliged to take a long tortuous path for diffusion from the lens. The diffusion attenuator effectively increases the path length, l, for diffusion of a bioactive agent through the lens from the path length absent the diffusion barriers. A conceptual illustration of the employment of diffusion barriers is shown in FIG. 1. FIG. 1A illustrates diffusion of a bioactive agent 1 in a lens 2 that is free of any diffusion barriers 3 as indicated by a dashed arrow. The bioactive agent can travel essentially in the transverse direction to diffuse from the lens. The average path length for a mobile bioactive agent can be as little as approximately half of the lens thickness when no diffusion barrier is present. In contrast, FIG. 1B illustrates the path of a bioactive agent 1 within a lens 2 which includes diffusion barriers 3. The bioactive agent 1 must diffuse around the diffusion barriers 3 in a tortuous manner, resulting in an increase in the path length and, therefore, a decrease in the transport rate of the bioactive agent 1, which increases the duration of drug release from the lens 2 relative to that of a lens that is free of the diffusion barriers 3.

The contact lens material can be a silicone hydrogel as described in International Application No. PCT/US2008/065325; filed May 30, 2008, published on Dec. 11, 2008 as WO 2008/151019 and hereby incorporated by reference herein in its entirety, including any figures, tables, or drawings. The contact lens material can also be any material used in soft contact lenses; such a hydroxyethylmethacrylate (HEMA) based lenses. The contact lens material can be a single phase, as in a homopolymer or random copolymer, or can consist of a plurality of discontinuous phases as is common of many block copolymers, such as silicone hydrogels. Commercially available silicone hydrogel contact lenses can be employed in embodiments of the invention. Silicone hydrogel contact lenses that are available commercially including: ACUVUE® ADVANCE™ (Johnson & Johnson Vision Care, Inc., Jacksonville, Fla.); ACUVUE® OASYS™ (Johnson & Johnson Vision Care, Inc., Jacksonville, Fla.); NIGHT&DAY™ (Ciba Vision Corp., Duluth, Ga.); $O_2$OPTIX™ (Ciba Vision Corp., Duluth, Ga.); and PureVision™ (Bausch & Lomb, Inc., Rochester, N.Y.). The commercially available lenses can be modified by incorporating the diffusion attenuator and the bioactive agent.

Silicone hydrogels can be prepared in a manner similar to that common to preparation of such networks, where hydrophobic silicon containing monomers are included into the formulation and the silicone monomer is copolymerized with monomers to provide hydrophilic character to the resulting network. Usually a silicone monomer that can undergo addition into the growing polymer at two sites or more is included. Such silicone hydrogels are non-homogeneous structures, often displaying discernable phase separation between a silicone rich phase and a hydrophilic monomer derived phase. Depending upon the nature of these hydrogels, surface treatment is sometimes necessary to assure the surface is sufficiently hydrophilic even though these hydrogels are designed to incorporate 20 to more than 80 percent by weight water. Surface treatment can include coating with a hydrophilic coating or plasma etching to convert the silicon surface into a hydroxy group rich silicate type surface.

Suitable silicone hydrogel materials include, without limitation, silicone hydrogels made from silicone macromers such as the polydimethylsiloxane methacrylated with pendant hydrophilic groups described in U.S. Pat. Nos. 4,259,467; 4,260,725 and 4,261,875; or the polydimethylsiloxane macromers with polymerizable functional described in U.S. Pat. Nos. 4,136,250; 4,153,641; 4,189,546; 4,182,822; 4,343,927; 4,254,248; 4,355,147; 4,276,402; 4,327,203; 4,341,889; 4,486,577; 4,605,712; 4,543,398; 4,661,575; 4,703,097; 4,740,533; 4,837,289; 4,954,586; 4,954,587; 5,034,461; 5,070,215; 5,260,000; 5,310,779; 5,346,946; 5,352,714; 5,358,995; 5,387,632; 5,451,617; 5,486,579; 5,962,548; 5,981,615; 5,981,675; and 6,039,913. The silicone hydrogels can also be made using polysiloxane macromers incorporating hydrophilic monomers such as those described in U.S. Pat. Nos. 5,010,141; 5,057,578; 5,314,960; 5,371,147 and 5,336,797; or macromers comprising polydimethylsiloxane blocks and polyether blocks such as those described in U.S. Pat. Nos. 4,871,785 and 5,034,461. All of the cited patents are hereby incorporated in their entireties by reference.

Among the silicone containing monomers which may be in the formulation of a silicone hydrogel of the present invention include oligosiloxanylsilylalkyl acrylates and methacrylates containing from 2-10 Si-atoms. Typical representatives include: tris(trimethylsiloxysilyl)propylmethacrylate, triphenyldimethyldisiloxanylmethylmethacrylate, pentamethyldisiloxanylmethylmethacrylate, tert-butyltetramethyldisiloxanyl-ethylmethacrylate, methyldi(trimethylsiloxy) silylpropylglycerylmethacrylate; pentamethyldisiloxanylmethylmethacrylate; heptamethylcyclotetrasiloxanylmethylmeth-acrylate; heptamethylcyclotetrasiloxanylpropylmethacrylate; (trimethylsilyl)decamethylpentasiloxanylpropylmethacrylate; undecamethylpentasiloxanylpropylmethacrylate; and the acrylate equivalents of these methacrylates.

Other representative silicon-containing monomers which may be used for silicone hydrogels of the present invention includes silicone-containing vinyl carbonate or vinyl carbamate monomers such as: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl[tris-(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxethyl vinyl carbonate; trimethylsilylethyl vinyl carbonate; and trimethylsilylmethyl vinyl carbonate. Polyurethane-polysiloxane macromonomers (also sometimes referred to as prepolymers), which have hard-soft-hard blocks like traditional urethane elastomers, may be used. Examples of such silicone urethanes which may be included in the formulations of the present invention are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996).

Suitable hydrophilic monomers that may be used separately or in combination for the silicone hydrogels of the present invention non-exclusively include, for example: unsaturated carboxylic acids, such as methacrylic and acrylic acids; acrylic substituted alcohols, such as 2-hydroxyethylmethacrylate, 2-hydroxyethylacrylate (HEMA), and tetraethyleneglycol dimethacrylate (TEGDMA); vinyl lactams, such as N-vinyl pyrrolidone; vinyl oxazolones, such as 2-vinyl-4,4'-dimethyl-2-oxazolin-5-one; and acrylamides, such as methacrylamide; and N,N-dimethylacrylamide (DMA). Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Hydrophilic monomers may be incorporated into such copolymers, including, methacrylic acid, 2-hydroxyethylmethacrylamide.

The proportions of the monomers can vary over a large range. The polymerization mixtures can also include effective amounts of additives, initiators, photoinitiators, and/or catalysts and that the reaction can be conducted in the presence of a diluent. Activation of the initiator for polymerization can be by thermal or photochemical means. The polymerization can occur via any ionic, radical or group transfer mechanism.

In embodiments of the invention, the contact lenses containing the diffusion attenuators can be used as a dosage form for delivering bioactive agents. Bioactive agents can include ocular drugs and nutraceuticals. Suitable drugs or mixtures of drugs for delivery by the contact lenses can be selected from, but are not limited to: glaucoma drugs such as timolol, pilocarpine, latanoprost; steroids such as dexamethasone and prednisilone; immunosuppressant such as cyclosporine; antibiotics such as ciprofloxacin, ciloxan and gentamycin; antiallergy drugs such ketotifen; and antiparisitic and antiprotzoal drugs such as ivermectin, and pyrimethamine. Nutraceutical or mixtures of nutraceuticals for delivery by the contact lenses can be selected from, but are not limited to: Vitamin B-1; Vitamin B-2; Vitamin B-3; Vitamin B-5; panthenol; pantothenic acid; Vitamin B-6; Vitamin B-8; Vitamin B-9; Vitamin B-12; Cobalamin; Pantothenic Acid; Folic Acid; Biotin; Choline Inositol; Para Amino Benzoic Acid; Ascorbic Acid; Vitamin C; Beta Carotene; Vitamin D; Vitamin E; Calcium; and salts that provide ionic Copper, Chromium, Iodine, Iron, Manganese, Magnesium, Molybdenum, Phosphorous, Potassium, Sodium, Selenium, and Zinc; colloidal minerals; chelated minerals; and RDA minerals. Mixtures of drugs and nutraceuticals can be delivered by the contact lens dosage form. Nutraceuticals are any non-drug compound that has a physiologically beneficial effect on the eye by improving the health of the eye or specifically preventing an ocular disease. In addition, some nutraceuticals, such as vitamin E, can impart a lubricating effect to reduce friction between the lens and the eye.

It was discovered that it was difficult to load Vitamin E into HEMA and silicone hydrogels in aqueous solutions because of the extremely low solubility of Vitamin E in water. It has been discovered that Vitamin E and other hydrophobic nutritious compounds can be loaded by soaking the lenses in solutions of the compounds in organic solvents such as ethanol. Non-limiting examples of such organic solvents include ethanol, ethyl acetate, butyl acetate isopropanol, n-propanol, DMSO, methanol, toluene, methylene chloride, and tetrahydrofuran. In general, the solvent should be one that has a low toxicity, is non-carcinogenic, and is non-mutanogenic or can be removed essentially in total from the silicone hydrogel by means commonly employed by those skilled in the art. Many hydrophobic compounds have some solubility in ethanol and so this solvent is most convenient. The solvents are generally, but not necessarily, removed prior to placement of the hydrogel into the ocular environment or other tissue to be treated. The solvent can be removed as a volatile off-gassing from the hydrogel and can be assisted separately or by any combination of vacuum, heating, and a gas stream.

In another embodiment of the invention, the hydrophilic nutraceutical, such as vitamin B, can be loaded into the hydrophilic segment of the lens derived from, for example, HEMA by soaking the lens in aqueous solutions. In these cases it is generally necessary to perform the loading over an extended period of time, varying from weeks to months, depending on effective rate of diffusion of the compounds in the hydrogels. The loading is slower in silicone hydrogels because they do not swell appreciably in water leading to small diffusivities. Loading in this fashion can be carried out where the silicon hydrogel article is sealed in a container that is used for distribution to a patient. The absorption of the bioactive agent into the article can occur over a long period of time, which includes the time of distribution of the appliance to patients. Typically, a use date indicated on such a package with this container would include an initial use date as well as an expiration date such that a sufficient, near equilibrium or equilibrium level of the bioactive agent in the appliance is achieved.

An alternative embodiment for the loading of the nutraceutical into the silicone hydrogels, according to the invention, is the inclusion of the compounds during the polymerization of monomers and macromers to prepare the silicone hydrogel appliance. For compounds that display little or no solubility in the monomer mixture, the addition of a solvent, such as those used for swelling of silicone hydrogels, can be included during a solution polymerization where all monomers and the nutraceutical are miscible.

In one embodiment of the invention, the bioactive agent is a hydrophobic drug. The drug can be loaded from a non-aqueous solution that also contains the nutraceutical. The relative concentrations of the drug and the nutraceutical delivered to the lens can be controlled by their relative concentrations in the solution. The relative concentration of the drug and nutraceutical in solution can be determined by considering the differences in the partitioning of the nutraceutical and drug between the non-aqueous solution and the lens. Partitioning coefficients for the nutraceutical and drug can be determined empirically.

Additional components, such as surface active agents including lipids and surfactants, can be incorporated to modify the loading and the release of any bioactive agent included in the lens. It was discovered that Vitamin E loaded into some lenses did not effectively diffuse from the lens into tear mimics due to Vitamin E's very small solubility in aqueous solution. In another embodiment of the invention one or more surface active agents, such as lipids and surfactants, are added to the contact lenses to facilitate dissolution of the compounds of interest into the tear film, and subsequent uptake by the eyes. Suitable surfactants include any ophthalmic compatible surfactants and lipids capable of providing the necessary attenuation in release rates without affecting the optical transparency of the resulting contact lens. Although some embodiments of the invention incorporate nonionic surfactants, as illustrated below, it should be understood that cationic, anionic, and zwitterionic surfactants can be used in embodiments of the invention. Linear and branched surfactants may be used. Of the non-ionic surfactants ethylene oxide alkyl ethers, for example eicosaethylene glycol octadecyl ether and polyethylene oxide—block—polypropylene oxide can be used.

Suitable surfactants include block copolymers which are generally classified by the ratio of the hydrophilic and lipophilic (hydrophobic) segments in the molecule. A large number of commercial emulsifying agents, such as surfactants, have been assigned a hydrophilic/lipophilic balance (HLB) number. The water soluble (hydrophilic) portions of the block copolymer can comprise or be derived from polyethylene glycol, polyethylene oxide, polyvinyl alcohol, polyacrylamide, polymethacrylamide, poly(vinylpyrrolidone), or other water soluble non-toxic polymers. The hydrophobic polymer segments are attached to hydrophilic polymer segments by non-hydrolyzable covalent chemical bonds, which non-exclusively include carbon-carbon bonds, amide linkages, ether linkages, ester linkages, thio linkages, and amino linkages. The hydrophobic polymer segments can have linear and/or branched saturated or partially unsaturated carbon chains and can have heteroatoms such as O, N, and S in the chain. Hydrophobic polymers that can be used include polypropylene oxide, poly(hydroxy butyrate), polystyrene, or any hydrophobic non-toxic polymers. The hydrophobic polymer segments can be: poly($\alpha$-hydroxycarboxylic acids), which are derived from either glycolide or lactide; poly($\omega$-hydroxycarboxylic acids), which are derived from either $\omega$-lactones, $\delta$-lactones, or $\epsilon$-lactones; and copolymers of $\alpha$-hydroxycarboxylic acids and $\omega$-hydroxycarboxylic acids.

In one embodiment of the invention, the block copolymer is a diblock copolymer composed of a hydrophilic polymer segment comprising ethylene oxide units and a hydrophobic polymer segment. In addition to polyethylene oxide units, some propylene oxide units, or other units that are a hydrophobic polymer when homopolymerized, may be present in the hydrophilic polymer segment. The hydrophobic units can be dispersed within the ethylene oxide units or be segregated to the portion of the hydrophilic segment adjacent to the hydrophobic polymer segment. In some embodiments the hydrophilic segments consist of ethylene oxide units.

The addition of a hydrophobic nutraceutical, such as Vitamin E, when partitioned to the surface of the lens, can render the lens hydrophobic. The hydrophobic nutraceutical can create an emulsion at the lens surface of some lens compositions, and can result in haziness and a loss of optical clarity of the lens. The inclusion of a surfactant reduces or removes the haze and loss of clarity. In another embodiment of the invention, surface treatment of the lenses is carried out to assure that the surface is hydrophilic. The surface treatment can be by any conventional means, such as plasma treatment or by chemically attaching hydrophilic polymer brushes to the surface.

In another embodiment of the invention, one or more ophthalmic drugs are included in the lens as the bioactive agent with a nutraceutical acting as a diffusion attenuator. The lens loaded with a hydrophobic nutraceutical, such as Vitamin E, and the drug is capable of sustaining release of some ophthalmic drugs for extended periods of time in contrast to a rapid "burst" release of the drug from a lens free of Vitamin E. Again, a surfactant can also be included to modify the absorption and release of the drug and/or the nutraceutical from the lens. The use of a nutraceutical as the diffusion attenuator advantageously allows the construction of a diffusion attenuator that is not harmful but can be beneficial if it diffuses from the contact lens to the eye. Having a diffusion barrier that is removed from the contact lens in an appropriate proportion can allow bioactive agent to diffuse from the lens at a greater rate at longer times when its concentration is low, than it would if the concentration of the diffusion attenuator is fixed over time.

In embodiments of the invention, as illustrated in FIG. 1, diffusion barriers can be any material that has a low affinity for the drug relative to the lens material. The partition coefficient for the bioactive agent in the lens over the barrier material is large, such that diffusion through the barrier material is negligible. In alternate embodiments, a diffusion attenuator material can have some affinity for the bioactive agent as does the lens material, but there is a lower diffusivity, D, of the bioactive agent through the diffusion attenuator than through the lens material such that some attenuation is due to a difference of diffusivity, D, and some attenuation is due to a barrier effect where the effective path length, l, is increased. Hence, the diffusion attenuator can occur via a mixed mechanism rather than simply acting to change the effective diffusivity or acting as a barrier to diffusion.

In some embodiments where the diffusion attenuator can be any material where the bioactive agent has a sufficiently smaller diffusivity than its diffusivity in the contact lens material can be employed. The diffusion attenuator material can be similar to the lens material, only differing, for example, by the repeating unit composition of a copolymer or by the cross-linking density, for example, a higher cross-link density, from that of the polymeric material used as the contact lens material.

Diffusion attenuators can be diffusion barriers that can have many different shapes. In one embodiment, the diffusion barriers can have large aspect ratios, such as that for a disc, plates, or an irregular flake. In other embodiments of the invention, the diffusion barriers can have shapes, such as spheroids, needles, rods, and spheres. The size of the diffusion barrier can vary considerably depending upon its properties, such as the index of refraction relative to that of the lens material. In one embodiment of the invention, when the diffusion barrier's size is large relative to the wavelength of light, a close match of the index of refraction between the barrier and lens material is required. In another embodiment of the invention, the barrier materials can have dimensions in the nanometer range, for example, the barrier can be a nanoparticle that has a maximum cross-section that is less than 400 nm. A diffusion barrier disc can be 1 to 50 nm thick and have a diameter that is 4 to 400 times its thickness. For example, a barrier disc can be about 1 micron thick and 30 microns in diameter. Standard techniques such as blow molding or spin coating of a resin followed by polymerization can be used to prepare a thin film, which can subsequently be crushed to create diffusion barrier flakes with a high aspect ratio. Many known microfabrication techniques can be used to prepare various shaped diffusion barriers.

The diffusion barrier can be any solid or any liquid material that can be dispersed within the lens material. In embodiments where the barrier is a liquid material, it must effectively phase separate from the material or materials of the lens. In one embodiment of the invention, the barrier is a liquid that forms a discontinuous sheet at the interface between phase separated components of a lens material. In another embodiment, the barrier material can phase separate into discontinuous particles within one or more separate phases of the lens material. When the diffusion attenuator material has little or no affinity for the bioactive agent, the barrier is effectively a diffusion barrier; otherwise the diffusion attenuator material can impart a mixed mode of attenuation by changing the effective diffusivity of the contact lens and acting as a barrier. Hence the scope encompassed by embodiments of the invention range from diffusion attenuators that solely change the diffusivity to attenuators that exclusively act as diffusion barriers and all combinations of these two extremes.

In some embodiments of the invention, the diffusion attenuators can be polymeric materials. For example, in one embodiment of the invention, highly cross-linked polymers such as an ethyleneglycoldimethacrylate (EGDMA) polymer or copolymer of EGDMA and other monomers such as HEMA, methyl acrylate (MA), or methylmethacrylate (MMA) are used. Other suitable cross-linked polymers include polymers and copolymers from: ethoxylated n-mers of trimethylolpropane triacrylate (wherein n=3, 6, 9, 15 or 200); trimethylolpropane triacrylate; tris-(2-hydroxy ethyl) isocyanurate triacrylate; 1,3-butylene glycol dimethacrylate; diethylene glycol dimethacrylate; alkoxylated hexanediol diacrylate; ditrimethylolpropane tetraacrylate; dipentaerythritol pentaacrylate; ethoxylated pentaerythritol tetraacrylate; dipentaerythritol pentaacrylate; or pentaacrylate ester.

In another embodiment of the invention, the diffusion attenuator can be inorganic materials include silica, glass, and inorganic crystals. Again, the diffusion attenuators can be particles where there is either a sufficient match of the refractive index with the contact lens material or the particles can be nanoparticles where their size is small relative to the wavelengths of light.

In one embodiment, a diffusion attenuator can be created inside the contact lens by dispersing diffusion barriers as preformed particles into a monomer mixture followed by polymerization to form the contact lens. The dispersion can be accomplished by mixing, sonicating or any other method of dispersion known to those skilled in the art. In one embodiment the polymerized hydrogel contains randomly oriented diffusion barriers with either symmetric or asymmetric particles. In another embodiment of the invention, asymmetric particles can have a specific orientation, for example where plates are predominately parallel to the surface of the lens by the employment of particles that can be oriented using an external field, such as electric or magnetic fields, or be oriented by flow during the molding of the contact lens.

In other embodiments of the invention, diffusion attenuators can be created loading preformed lenses with liquids that will act as diffusion barriers when loaded at a concentration above its solubility limit in the contact lens material. The barrier forming liquid can be dissolved in a solvent that swells the contact lens and the lens can be placed in the barrier liquid loaded solvent. Swelling of the lens is accompanied by uptake of the barrier forming liquid. Subsequent evaporation of the carrier solvent leads to the lens returning to nearly its original size and/or shape but where the barrier forming liquid has phase separated to form the diffusion barriers. Non-limiting examples of organic solvents suitable for loading the barrier-forming liquids into the lenses include ethanol, ethyl acetate, butyl acetate isopropanol, n-propanol, DMSO, methanol, toluene, methylene chloride, and tetrahydrofuran. In general, the solvent should be one that has a low toxicity, is non-carcinogenic, and is non-mutanogenic, or can be removed essentially in total from the contact lenses by means known by those skilled in the art.

The diffusion attenuator can be incorporated with the aid of a dispersing agent. The dispersing agent can be a surfactant. For example, a block copolymer where one block has an affinity for the diffusion attenuator and the other block has an affinity for a material of the contact lens can be employed to prepare or to stabilize the dispersion of the diffusion barriers.

In an embodiment of the invention, the diffusion attenuator can be viscous liquids such as Vitamin E, Vitamin A, silicone oils, or hydrocarbon oils that can separate into a discontinuous phase forming the diffusion barriers. In one embodiment of the invention, the liquid is a hydrophobic material that forms diffusion barriers for hydrophilic drugs, such as ionizable drugs, including timolol and dexamethasone phosphate.

Materials and Methods

Example 1

Loading of Vitamin E in an Experimental Silicone-Hydrogel as a Function of Loading Concentration Silicon-hydrogel contact lenses were prepared by the polymerization of a mixture of methacryloxypropyltris(trimethylsiloxy)silane (TRIS) (1 ml), bis-alph,omega-(methacryloxypropyl)polydimethylsiloxane (1 ml), N,N-dimethylacrylamide (DMA) (0.6 ml), Methacrylic Acid (0.6 ml), 1-vinyl-2-pyrrolidone (0.15 ml) and ethylene glycol dimethacrylate (EGDMA) (0.125 ml). The lenses were soaked in various concentrations of Vitamin E in ethanol until partitioning was complete between the solution and the lens. The uptake of Vitamin E per weight of lens is plotted in FIG. 2 as a function of the concentration of Vitamin E in ethanol. As can be seen in FIG. 2, the equilibrium loading of the lenses was proportional to the concentration of the Vitamin E in solution. A Vitamin E loading of up to 18 wt % of the pure silicone hydrogel was possible without any changes in the optical properties of the lenses.

Example 2

Loading of Vitamin E in Commercial Silicone-Hydrogel Contact Lens as a Function of Loading Concentration Five commercial silicone contact lenses (diopter −6.50) as indicated and characterized in Table 1, below, were used. Loading of Vitamin E in a variety of commercial silicone-hydrogel contact lenses was carried out by dissolving Vitamin E in ethanol at various concentrations and soaking the lenses for a period of time for complete partitioning between the solution and the lens to achieve various loadings in the lens. The solvent was allowed to evaporate and the weight increase and diameter increase of the lens was measured as recorded in Table 2, below. As can be seen in Table 2, the lens absorbed Vitamin E up to about the mass of the lens. The lens diameter also increased with the Vitamin E loading.

Example 3

Vitamin E Loading into Commercial Lenses

Vitamin E was loaded into lenses by soaking the lens in 3 ml of a Vitamin E-ethanol solution for 24 hours. Vitamin E-ethanol solutions of various concentrations were prepared by simply mixing Vitamin E and ethanol with vortex mixing for a few seconds followed by moderate magnetic stirring for several minutes. After the loading step, the lens was taken out and excess Vitamin E-ethanol solution on the lens surface was blotted with wipes and dried in air overnight.

Figure 3:
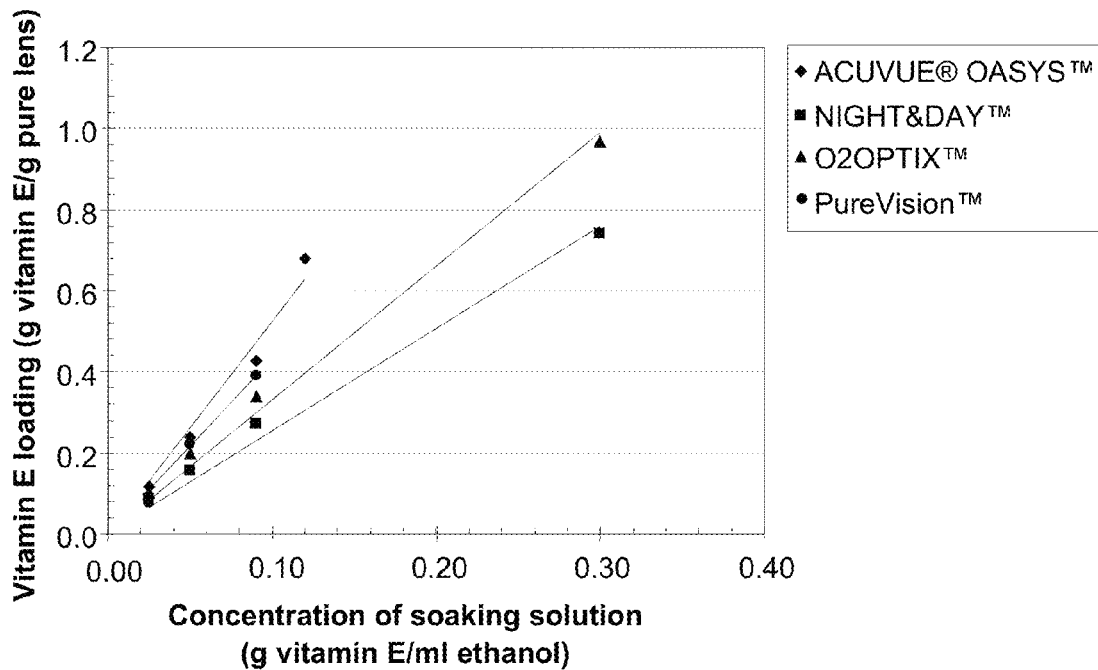
FIG. 3 shows plots of Vitamin E loading as a function versus the Vitamin E concentration of solution as best fit straight line with slopes and $R^2$s of 5.26, 0.9692 (ACUVUE® OASYS™), 2.53, 0.9860 (NIGHT&DAY™), 3.30, 0.9918 ($O_2$OPTIX™), 4.35, 0.9997 (PureVision™), respectively as indicated in the legend.

Vitamin E loadings in lens of different initial concentration of Vitamin E loading solutions are shown in FIG. 3. Vitamin E loading has a linear dependency on the concentration of Vitamin E loading solutions. ACUVUE® OASYS™ and NIGHT&DAY™ have the highest and the lowest affinity for Vitamin E, respectively. The Vitamin E loaded lenses were transparent at all loadings.

TABLE 1

Silicone containing commercial contact lens (dipoter −6.50) used in this study. (n = 6)

| Commercial name[a] (manufacturer) | Material[a] | Dry weight measured [mg] | Water content, Q measured (listed[a]) [%] | EW measured [%] | Diameter [mm] Wet measured (listed[a]) | Dry measured |
|---|---|---|---|---|---|---|
| ACUVUE® ADVANCE™ (Johnson&Johnson Vision Care, Inc., Jacksonville, FL) | Galyfilcon A | 19.7 ± 0.3 | 46.2 ± 0.7 (47) | 86.1 ± 2.3 | 14.40 ± 0.31 (14.0) | 11.46 ± 0.34 |
| ACUVUE® OASYS™ (Johnson&Johnson Vision Care, Inc., Jacksonville, FL) | Senofilcon A | 21.7 ± 0.1 | 36.9 ± 0.9 (38) | 58.4 ± 1.5 | 14.12 ± 0.26 (14.0) | 12.18 ± 0.29 |
| NIGHT&DAY™ (Ciba Vision Corp., Duluth, GA) | Lotrafilcon A | 22.2 ± 0.3 | 23.6 ± 0.3 (24) | 27.3 ± 0.6 | 13.92 ± 0.07 (13.8) | 12.85 ± 0.15 |
| O₂OPTIX™ (Ciba Vision Corp., Duluth, GA) | Lotrafilcon B | 25.9 ± 0.2 | 31.5 ± 1.3 (33) | 46.0 ± 2.7 | 14.43 ± 0.23 (14.2) | 12.78 ± 0.12 |
| PureVision™ (Bausch & Lomb, Inc., Rochester, NY) | Balafilcon A | 21.0 ± 0.2 | 35.0 ± 0.7 (36) | 53.9 ± 1.7 | 14.18 ± 0.15 (14.0) | 12.49 ± 0.17 |

[a]Referred from product packages

TABLE 2

Change in weight and diameter of Vitamin E laden contact lenses

| Contact Lens | Loading Solution (g Vitamin E/ml ethanol) | Loading (g Vitamin E/g lens) | % dry diameter increase | % wet diameter increase |
|---|---|---|---|---|
| NIGHT&DAY™ | 0.025 | 0.08 | 1.5 | 0.0 |
|  | 0.030 | 0.10 | — | — |

TABLE 2-continued

Change in weight and diameter of Vitamin E laden contact lenses

| Contact Lens | Loading Solution (g Vitamin E/ml ethanol) | Loading (g Vitamin E/g lens) | % dry diameter increase | % wet diameter increase |
|---|---|---|---|---|
| | 0.050 | 0.16 | 6.8 | 0.6 |
| | 0.090 | 0.30 | 7.8 | 5.7 |
| O$_2$OPTIX ™ | 0.010 | 0.01 | 2.5 | 0.0 |
| | 0.025 | 0.08 | 4.3 | 1.0 |
| | 0.030 | 0.14 | — | — |
| | 0.050 | 0.18 | 10.5 | 1.3 |
| | 0.090 | 0.35 | 13.7 | 7.7 |
| | 0.300 | 0.95 | 41.2 | 17.0 |
| PureVision ™ | 0.025 | 0.11 | 0.1 | 0.3 |
| | 0.030 | 0.13 | — | — |
| | 0.050 | 0.22 | 3.6 | 1.2 |
| | 0.090 | 0.39 | 8.9 | 4.4 |

Example 4

Water Content of Vitamin E Loaded Lenses

Water contents (Q) of lenses are listed on each lens package and were measured. Water content is determined as follows.

$$\text{Water content } (Q) = \frac{W_{eq} - W_l - W_{ve}}{W_{eq}} \times 100 \quad (1)$$

where $W_{eq}$, $W_l$, and $W_{ve}$ are mass of hydrated lens at equilibrium, mass of dry pure lens, and mass of Vitamin E loaded in the lens, respectively. The listed and measured Q's are given in Table 1. Water content of lens can also be expressed as the equilibrium water content (EW), defined as the mass of water absorbed per unit mass of pure lens and expressed as:

$$\text{Equilibrium water content } (EW) = \frac{W_{eq} - W_l - W_{ve}}{W_l} \times 100 \quad (2)$$

Figure 4A:
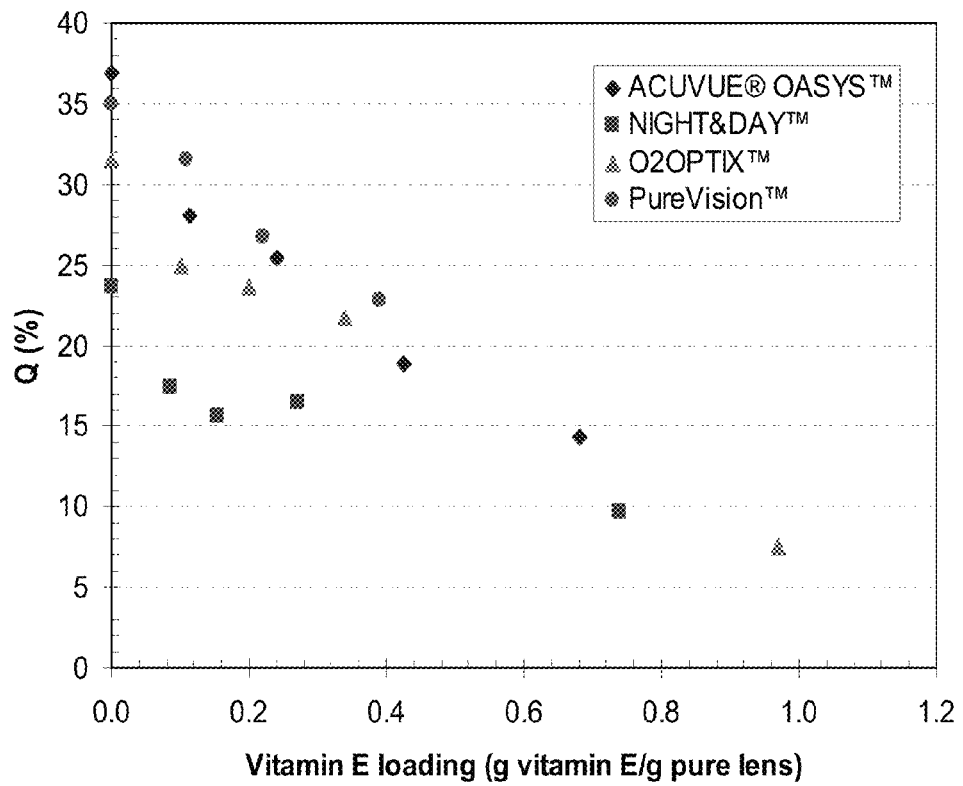
FIGS. 4A-4B shows plots of A) water content (Q) and B) EW of Vitamin E loaded lenses versus Vitamin E loading for lenses indicated in the legend.
Figure 4B:
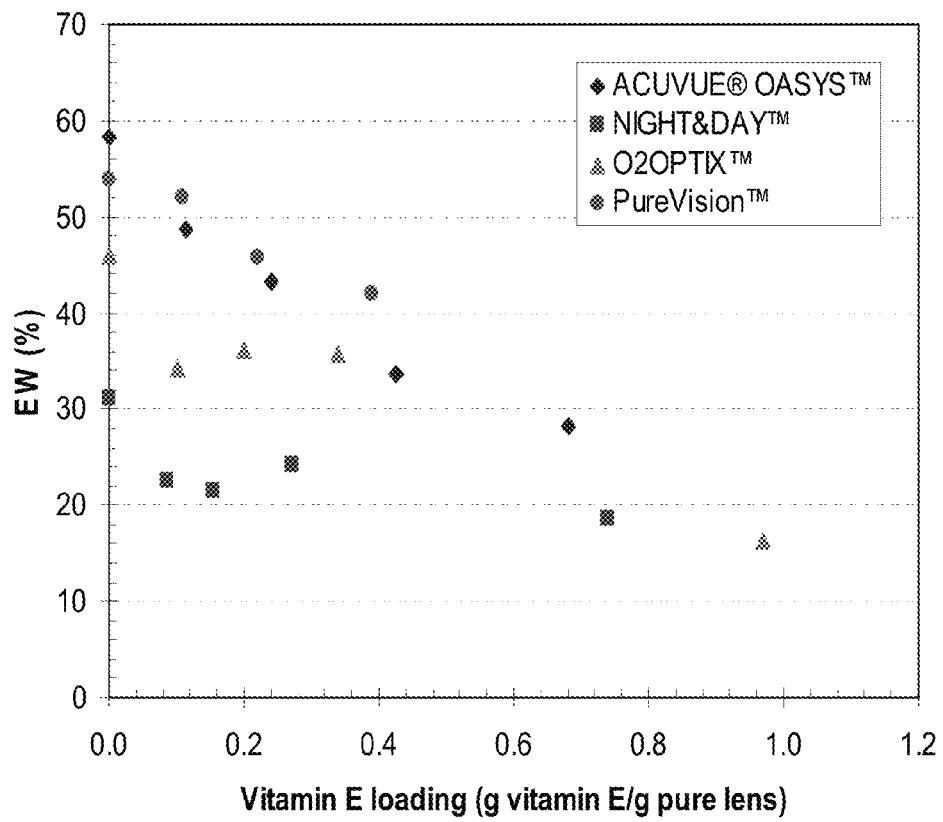

EW's are also listed in Table 1 where ACUVUE® ADVANCE™ lenses show a high EW (86.1±2.3) and NIGHT&DAY™ a relatively low EW (27.3±0.6). Q and EW were measured also for Vitamin E loaded lenses and shown in Table 3. The effect of Vitamin E loading on Q and EW are given in FIG. 4. In FIG. 4A, water content of Vitamin E loaded lenses tends to decrease relatively linearly as Vitamin E loading increases. However, $W_{eq}$ of Vitamin E loaded lenses increases with Vitamin E loading, resulting in a decrease in Q values. To observe the effect of Vitamin E loading on water amount absorbed in the lens material, EW was plotted versus Vitamin E loading in FIG. 4B. The EW for Vitamin E loaded lenses is less than that for the pure lenses for each type of lens, which display different trends. The EW's of ACUVUE® OASYS™ and PureVision™ lenses linearly decrease and the values of EW are 46% and 44% respectively for about 20% vitamin loading. The EW's of NIGHT&DAY™ and O$_2$OPTIX™ lenses decrease by about 10% for Vitamin E loadings of about 10% but there is negligible decrease in EW's with further increase in Vitamin E loadings. The latter behavior for the NIGHT&DAY™ and O$_2$OPTIX™ lenses suggests that at low loadings, the Vitamin E is solubilized in the lens and so it reduces the water content of the gel because of its hydrophobicity, but that beyond a critical weight fraction, the extra Vitamin E simply phase separates, and has no further effect on the EW. The critical Vitamin E loading that can be solubilized by the NIGHT&DAY™ and O$_2$OPTIX™ appears to be less than 10%, which is consistent with the values obtained for drug transport data (6.2% for NIGHT&DAY™ and 9.7% for O$_2$OPTIX™), which is addressed below. The continuous linear decrease in EW for ACUVUE® OASYS™ and PureVision™ lenses suggests that these lenses can either solubilize large amounts of Vitamin E or the Vitamin E that phase separates coats the polymer and thus continues to reduce the EW.

TABLE 3

Changes in lens properties before and after loading Vitamin E.

| Contact lenses | Loading [g Vitamin E/ g pure lens] | Vitamin E-ethanol solution [g Vitamin E/ ml ethanol] | Diameter increase [%] dry | Diameter increase [%] wet | Water content Q [%] | EW [%] |
|---|---|---|---|---|---|---|
| ACUVUE® OASYS ™ | 0.00 | 0.000 | — | — | 36.9 | 58.4 |
| | 0.11 | 0.025 | 7.0 | 2.2 | 28.1 | 48.6 |
| | 0.24 | 0.050 | 8.3 | 2.4 | 25.4 | 43.3 |
| | 0.42 | 0.090 | 14.0 | 5.8 | 18.8 | 33.6 |
| | 0.68 | 0.120 | 20.1 | 11.2 | 14.3 | 16.7 |
| NIGHT & DAY ™ | 0.00 | 0.000 | — | — | 23.6 | 31.1 |
| | 0.09 | 0.025 | 4.1 | 1.0 | 17.4 | 22.5 |
| | 0.16 | 0.050 | 6.8 | 3.2 | 15.7 | 21.6 |
| | 0.27 | 0.090 | 11.1 | 5.0 | 16.5 | 24.3 |
| | 0.74 | 0.300 | 24.3 | 18.3 | 9.7 | 18.5 |
| O$_2$OPTIX ™ | 0.00 | 0.000 | — | — | 31.5 | 46.0 |
| | 0.10 | 0.025 | 3.1 | 2.2 | 24.9 | 34.3 |
| | 0.20 | 0.050 | 6.6 | 5.5 | 23.6 | 36.2 |
| | 0.34 | 0.090 | 15.6 | 7.8 | 21.7 | 35.8 |
| | 0.97 | 0.300 | 25.0 | 18.2 | 7.5 | 16.3 |
| PureVision ™ | 0.00 | 0.000 | — | — | 35.0 | 53.9 |
| | 0.11 | 0.025 | 6.4 | 1.4 | 31.5 | 52.0 |
| | 0.22 | 0.050 | 9.7 | 3.7 | 26.8 | 45.8 |
| | 0.39 | 0.090 | 12.8 | 6.7 | 22.8 | 42.0 |

Example 5

Size Change Due to Vitamin E Loading

Figure 5A:
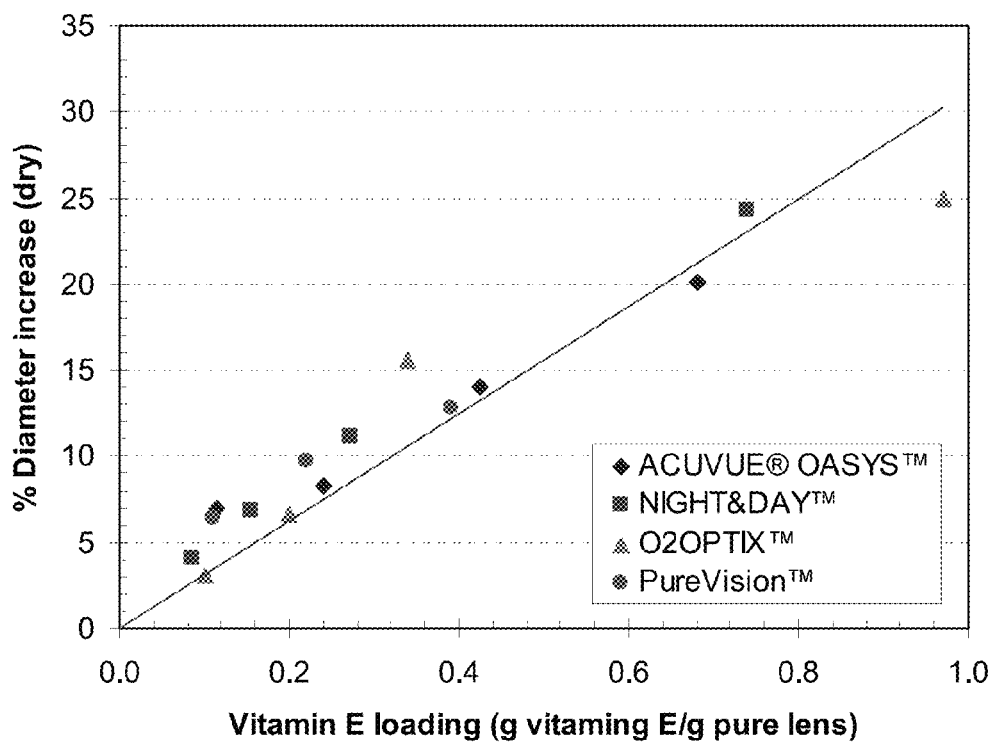
FIG. 5A-5B shows plots of the percent increase in diameter of A) dry lenses B) wet lenses before and after loading Vitamin E for various lenses as indicated in the legend where the lines are best fit straight lines passing through zero.
Figure 5B:
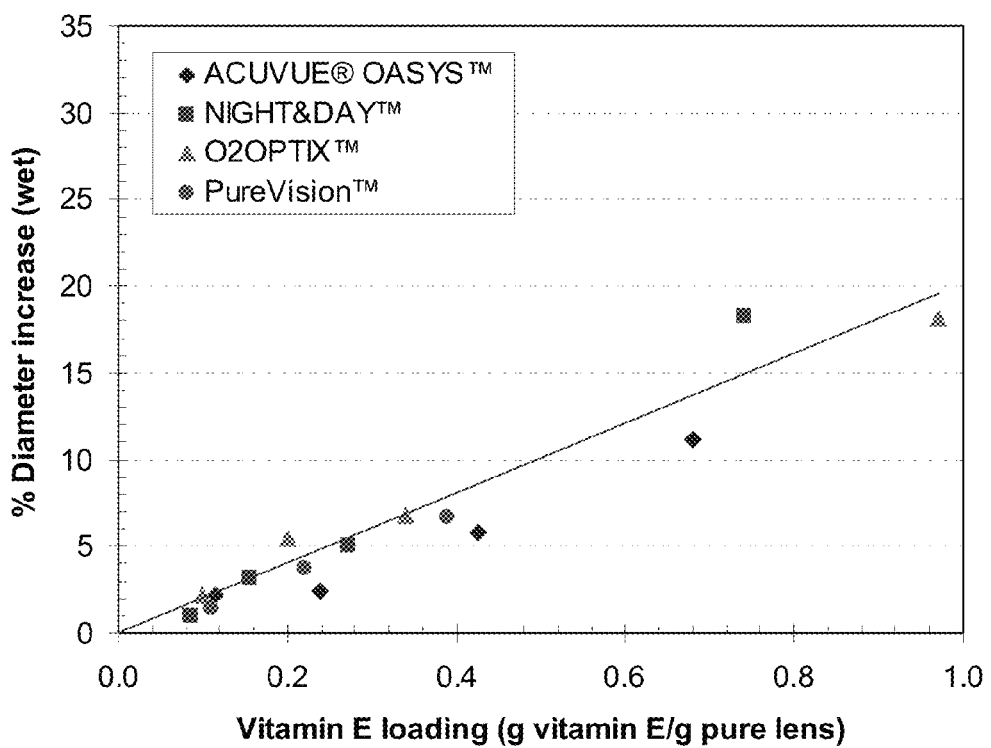
Figure 6A:
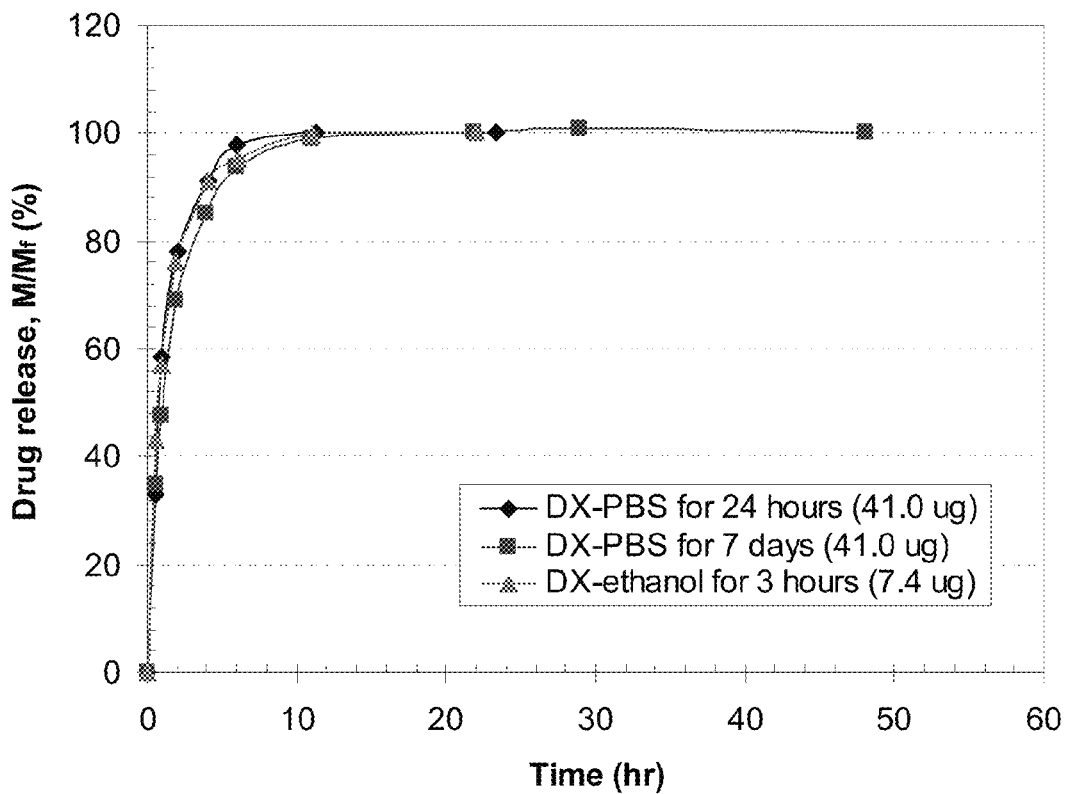
FIGS. 6A-6E shows plots of DX release from A) ACUVUE® ADVANCE™, B) ACUVUE® OASYS™, C) NIGHT&DAY™, D) $O_2$OPTIX™, and E) PureVision™ contact lenses as the mass of drug release (M) divided by total mass released ($M_f$) versus time for lenses where DX was loaded by soaking the lens in 0.08 mg/ml of the solution for the duration of time indicated in the legend with the total amount of drug released for each lens in parentheses.
Figure 6B:
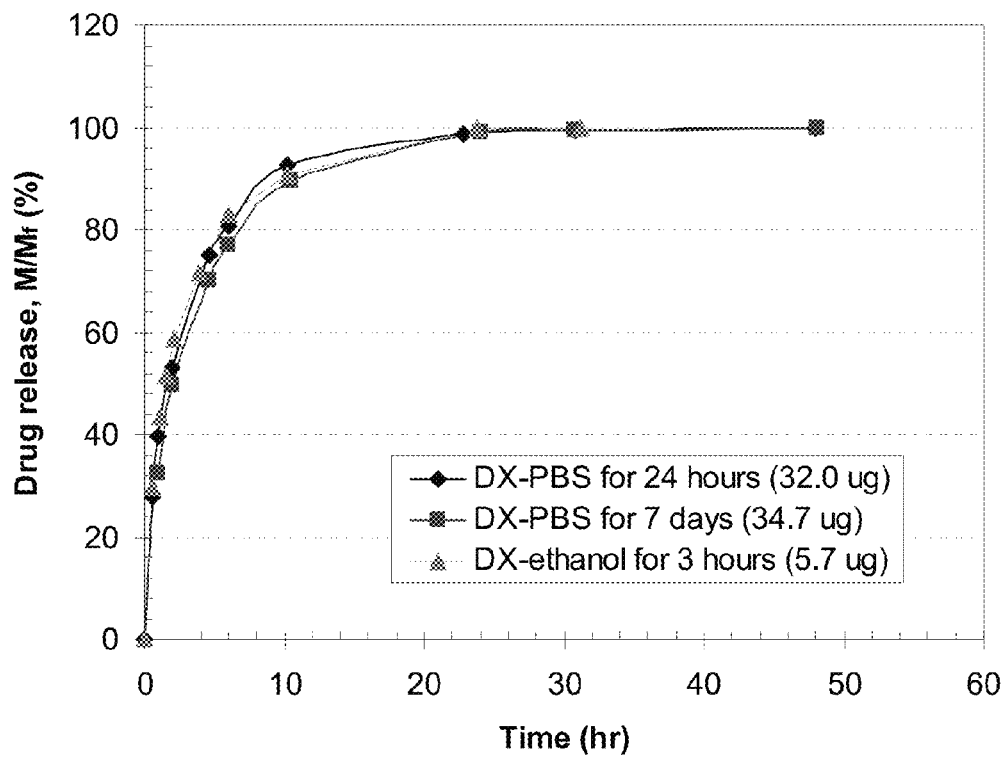
Figure 6C:
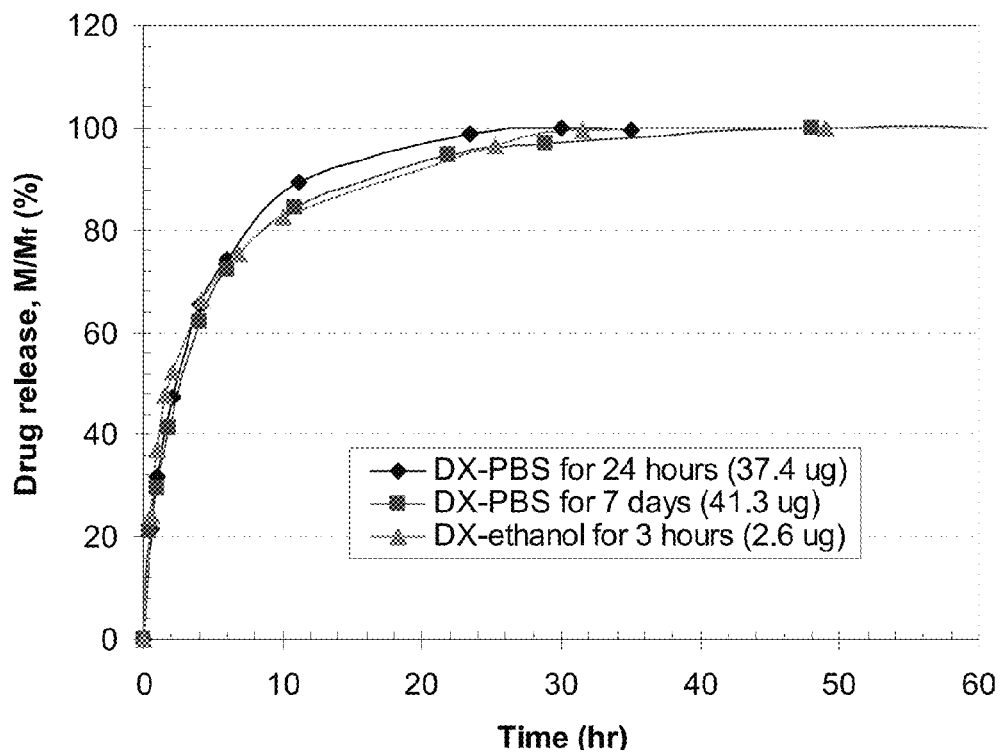
Figure 6D:
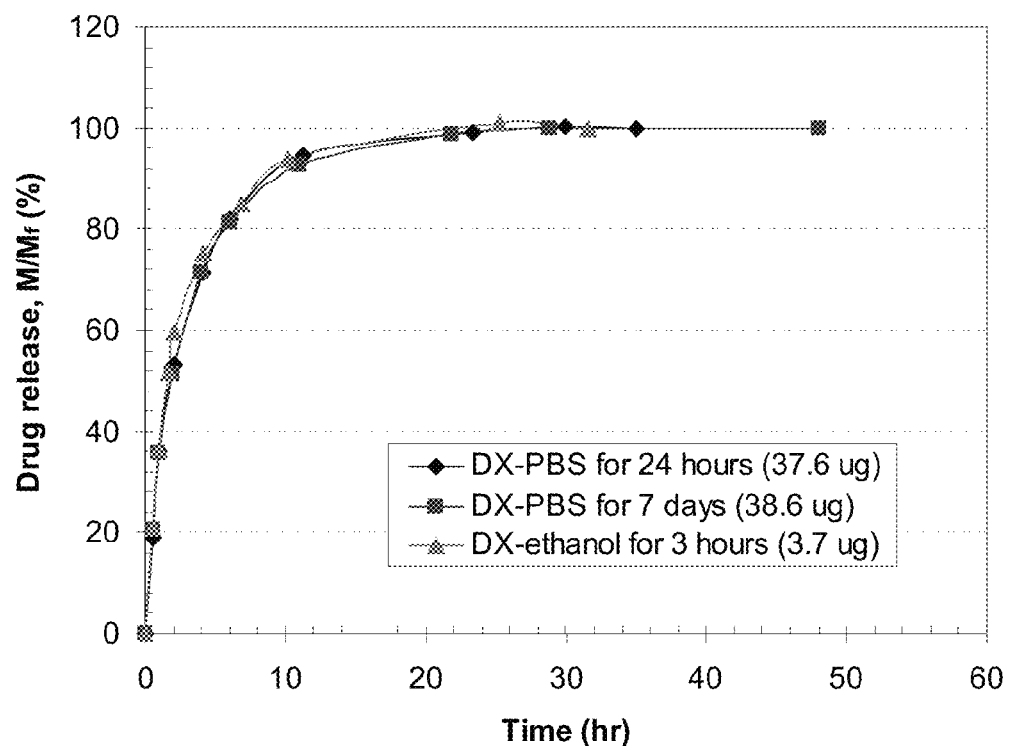
Figure 6E:
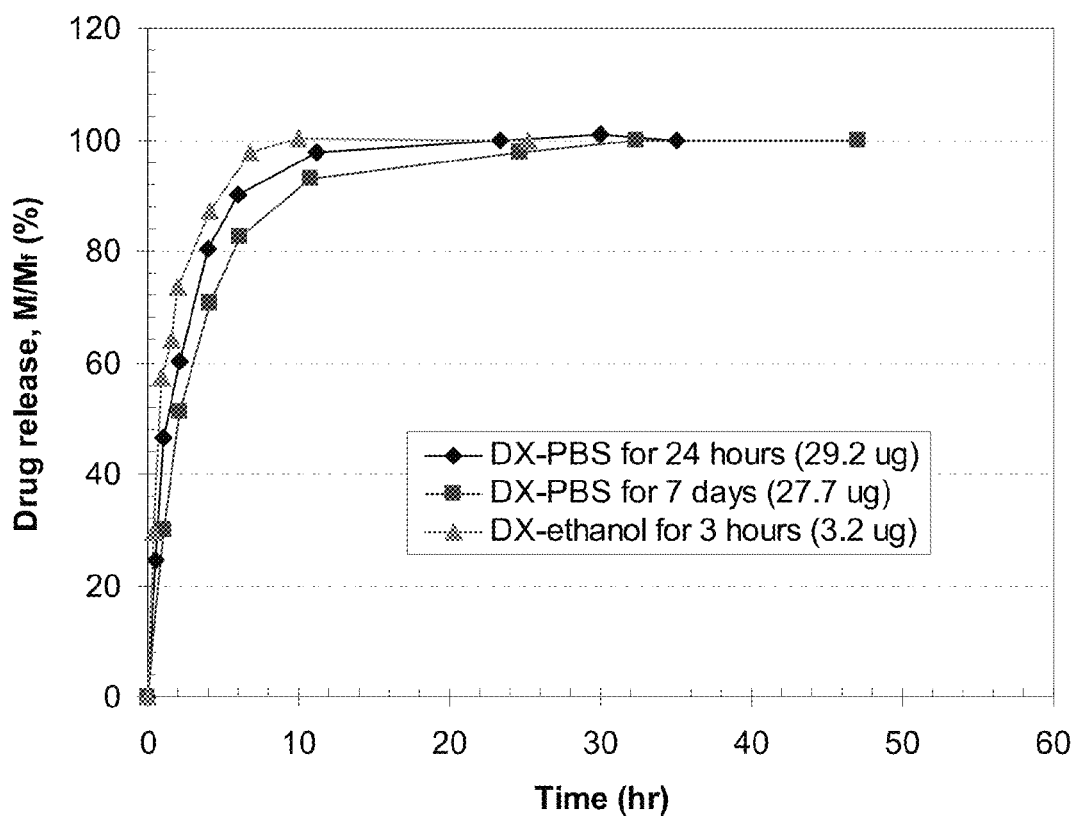

The sizes of the contact lenses increase due to Vitamin E uptake. The diameters of the lenses with and without Vitamin E were measured in dry and hydrated states, and the size changes of lenses after loading the Vitamin E are shown in FIG. 5. The % dry and hydrated diameter increase are the increase in the dry and hydrated diameter divided by the dry and hydrated diameter of the lens without Vitamin E, respectively. The solid lines in the figure are the best fit straight lines. FIG. 5A shows that the dry diameter change of lenses is about 30% of the Vitamin E loading. For example, about 30% Vitamin E loaded lens shows increase of about 10% in diameter in dry state, which suggests that the expansion of lens by Vitamin E loading is isotropic. In FIG. 5B, wet diameter change is less than dry diameter change, as Vitamin E does not absorb water. For example, lenses with about 30% Vitamin E loaded lens expand about only 6.5% in diameter. From application perspective, changes in wet diameter should be small to preserve the power of the contact lens, and all the lenses show less than 8% increase in wet diameter for about 40% of Vitamin E, levels which the eye should be able to tolerate. There may be changes to the corrective power due to refractive index changes in the lens.

Example 6

Drug Loading into Vitamin E Free (Pure) Lenses

The commercial silicone contact lenses were rinsed with deionized (DI) water and then dried in air before further use. The drug timolol maleate was converted to timolol base for further use by increasing the pH of timolol maleate solution, and then separating out the precipitated timolol base. All other drugs were used as supplied. The drug (timolol, DX, DXP, fluconazole) was loaded into the lenses by soaking the lens either in 2 ml of a drug-PBS solution for 1 or 7 days or in the same volume of a drug-ethanol solution for 3 hours. For drug Cyclosporine A (CyA), the CyA-PBS solution was prepared by dissolving 2.5 mg CyA in 100 ml PBS with moderate stirring in refrigerator for 24 hours, and then diluting it with PBS to desired drug concentration. CyA was loaded into the lens by soaking the lens in 10 ml of a 15 µg/ml CyA-PBS solution for 7 days. After loading, the lens was taken out and excess drug solution was blotted from the surface. The lens was then dried in air overnight, and used for later release experiments.

Example 7

Dynamics of DX Loading and Release Using Vitamin E Free Contact Lenses

Figure 7:
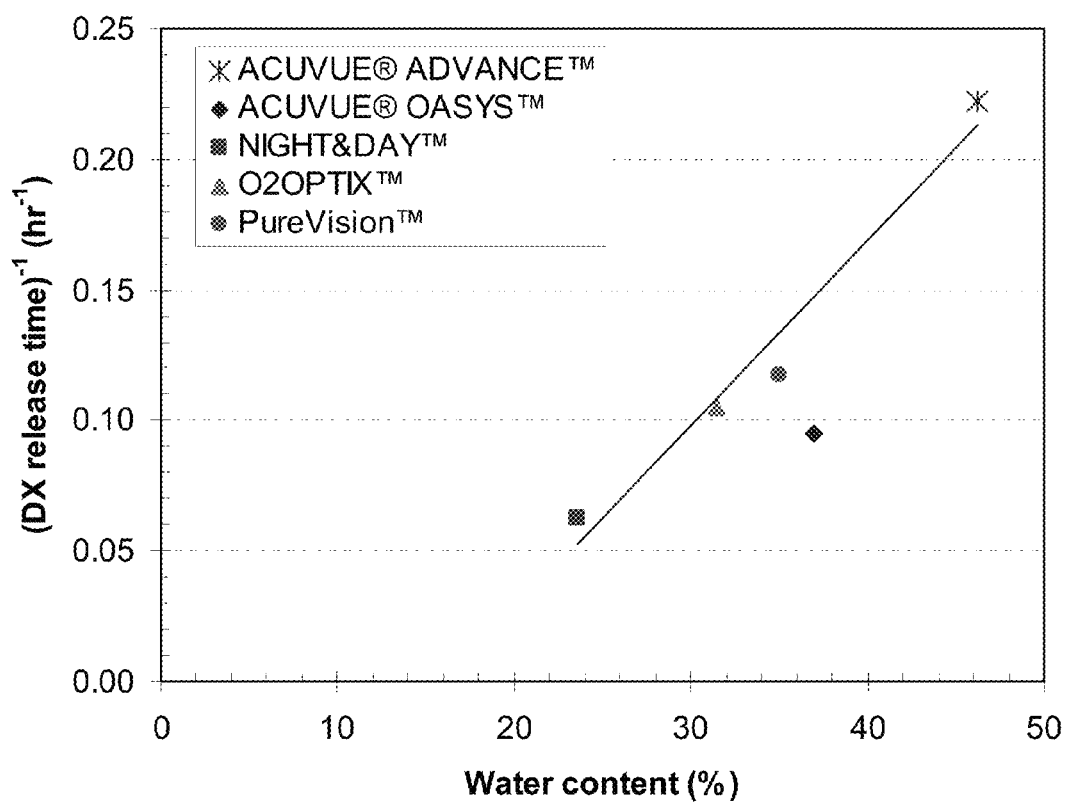
FIG. 7 shows a plot of (DX release time)$^{-1}$ versus water content of contact lenses.

DX releases from five different contact lenses for three different loading methods are shown in FIG. 6. For various drug loading methods, the mass of drug released at various time increments was divided by the total drug released at long time and plotted as a function of time. Since DX is a hydrophobic drug and has limited solubility in PBS, a nearly saturated DX-PBS solution of 0.08 mg/ml at room temperature was used for DX loading into lenses. A DX-ethanol solution of equivalent concentration as the DX-PBS, 0.08 mg/ml as that of DX-PBS solution was used to allow direct comparison of the two loading modes, although a saturated DX in ethanol is about 1 mg/ml. As seen in FIG. 6, for ACUVUE® ADVANCE™, ACUVUE® OASYS™ and O₂OPTIX™, the DX release profiles of three different loading methods are identical. However, the DX release behaviors by NIGHT&DAY™ and PureVision™ lenses exhibit a slight dependency on loading methods. For these lenses, there is not much difference in the total release amount of DX from the lenses soaked in DX-PBS solution for two different soaking times, but slower DX release is observed from lenses that were soaked for 7 days than that for 24 hours. This suggests that equilibrium time for DX loading for these two lenses could be longer than 24 hours. Among five lenses, NIGHT&DAY™ lens shows the longest release time (16 hours for 90% of total release) followed by ACUVUE® OASYS™ (10.5 hours), O₂OPTIX™ (9.5 hours), and PureVision™ (8.5 hours), with ACUVUE® ADVANCE™ having the shortest release time (4.5 hours) by loading the drug with DX-PBS solution for 7 days. There is a good correlation between the water content of the lenses reported by the manufacturers and the duration of release as shown in FIG. 7, with increasing water content resulting in shorter release durations. For total release amount of DX, PureVision™ and ACUVUE® OASYS™ lenses release relatively smaller amounts (about 28 µg and 35 µg, respectively) compared to the other three lenses (about 38-41 µg). There is no correlation between amount of drugs released and the water content, which is likely because the hydrophobic drugs are expected to partition in the silicone rich phases, and so the partition coefficients in the gels will be mainly influenced by the silicone composition of the lenses. All the lenses soaked in DX-ethanol solution release substantially low amount of DX (2-8 µg). The solubility of DX in ethanol is very high and the partition coefficient of DX between lens and ethanol is very low in the drug loading step, resulting in low loading of DX.

Example 8

Timolol Loading and Release Using Vitamin E Free Contact Lenses

Figure 8:
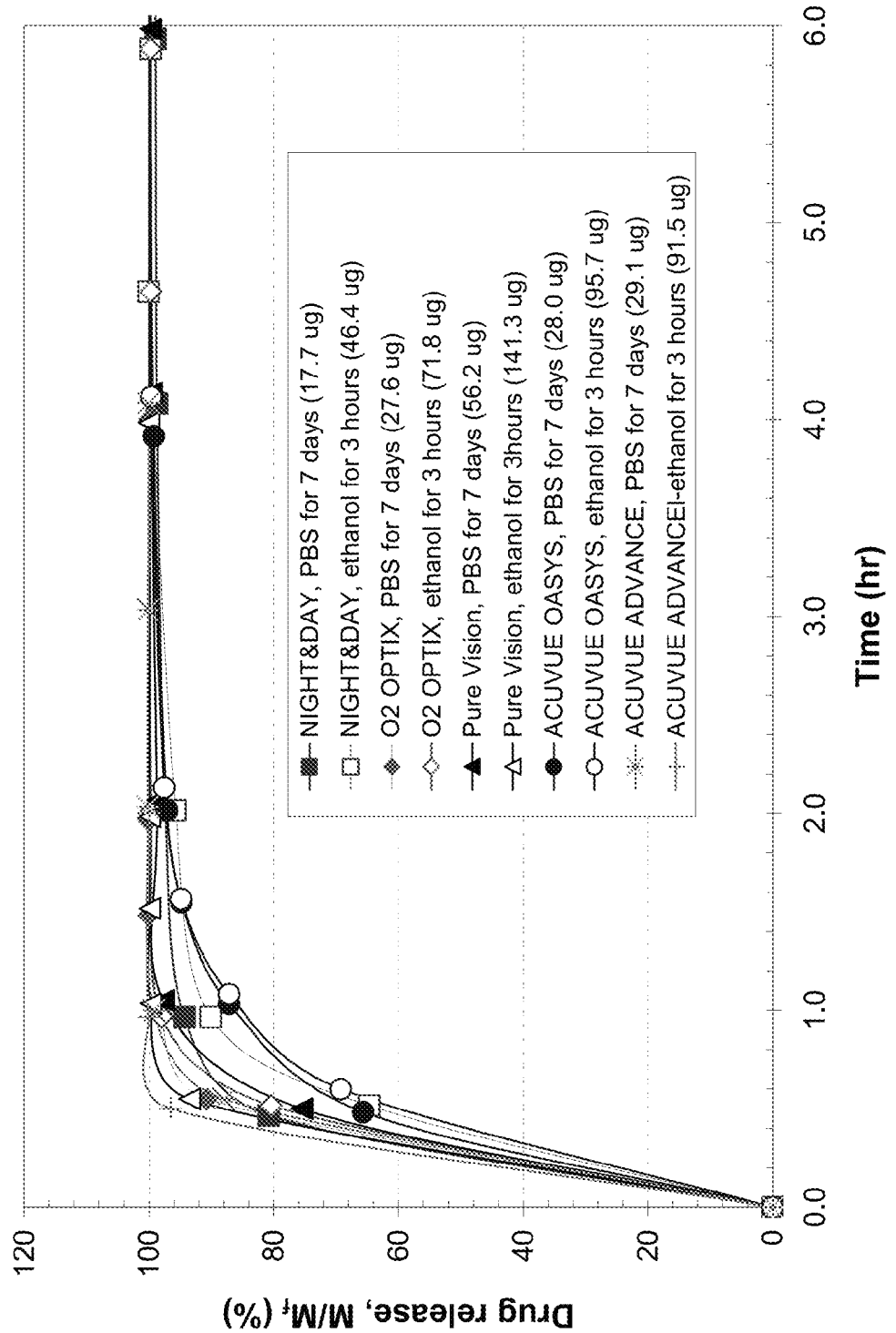
FIG. 8 shows plots of timolol release by ACUVUE® ADVANCE™, ACUVUE® OASYS™, NIGHT&DAY™, $O_2$OPTIX™, and PureVision™ contact lenses as the mass of drug release (M) divided by total mass released ($M_4$) versus time for lenses where timolol was loaded by soaking the lens in 0.8 mg/ml of the solution for the duration of time indicated in the legend with the total amount of drug released for each lens in parentheses.

FIG. 8 shows the dynamics of timolol release from the five different contact lenses soaked in 0.8 mg/ml of timolol-PBS solution or timolol-ethanol solution. Timolol-PBS solutions were used to soak lenses for either 24 hours or 7 days and timolol-ethanol solution were used to soak lenses for 3 hours. The release profiles for 24 hours in PBS are not shown in FIG. 8 as they were identical to those for 7 days soaking in PBS. To observe the effect of different loading methods on timolol release dynamics, mass of drug released divided by total drug released is plotted as a function of time. All the lenses release 90% of timolol in less than 1.5 hours. In addition, the timolol release profiles for like lenses using different loading methods were similar for each like lens, with the exception of that for PureVision™ lens which showed a slightly faster release from the lens soaked in timolol-ethanol solution than those soaked in PBS medium. ACUVUE® OASYS™ lenses release 90% of the timolol relatively slowly for the initial 1.2 hours relative to the initial release for the other lenses. ACUVUE® ADVANCE™ lens exhibits rapid timolol release, requiring less than 0.5 hour and the other three lenses showed similar release durations. The release durations of timolol did not appear to correlate with the water content of the lenses. The total amount of drug released from the lens was the highest by PureVision™ (about 57 µg), the lowest by NIGHT&DAY™ (about 18 µg), and those of the other lenses were similar and ranged from 26-30 µg based on the PBS medium soaking method. The amounts of timolol uptake and release are also uncorrelated to the water content likely due to differences in the hydrophilic components of the lenses, which leads to differences in drug binding to the hydrophilic component rich phases in the lenses. All the lenses soaked in ethanol solution for 3 hours release high total amounts of timolol, being 2.5-3 times higher than those soaked in PBS solution. For example, ACUVUE® OASYS™ lens soaked in PBS solution for 7 days releases 28 µg of timolol, but lenses soaked in ethanol solution for 3 hours release about 95.7 µg during the same period. The increased uptake of timolol from ethanol soaking is likely due to the fact that timolol does not ionize in ethanol and so it preferentially binds to the polymer. In PBS, the drug in almost entirely ionized, which leads to a very large solubility in water, and consequently to small binding to the lens. Therefore, the 3 hour ethanol soaking method is efficient for higher timolol loading using any of the five lenses using soaking solution of equivalent concentration, while durations of timolol release are equivalent.

Example 9

DXP and Fluconazole Loading and Release Using Vitamin E Free Contact Lenses

The drug release from control lenses, without Vitamin E, were conducted with DXP and fluconazole displayed trends and features as those for timolol mentioned above. The % release profiles were independent of the method of loading and the total release durations were all about 1-10 hours.

Example 10

Uptake and Release of CyA Using Vitamin E Free (Pure) Contact Lenses

Figure 9A:
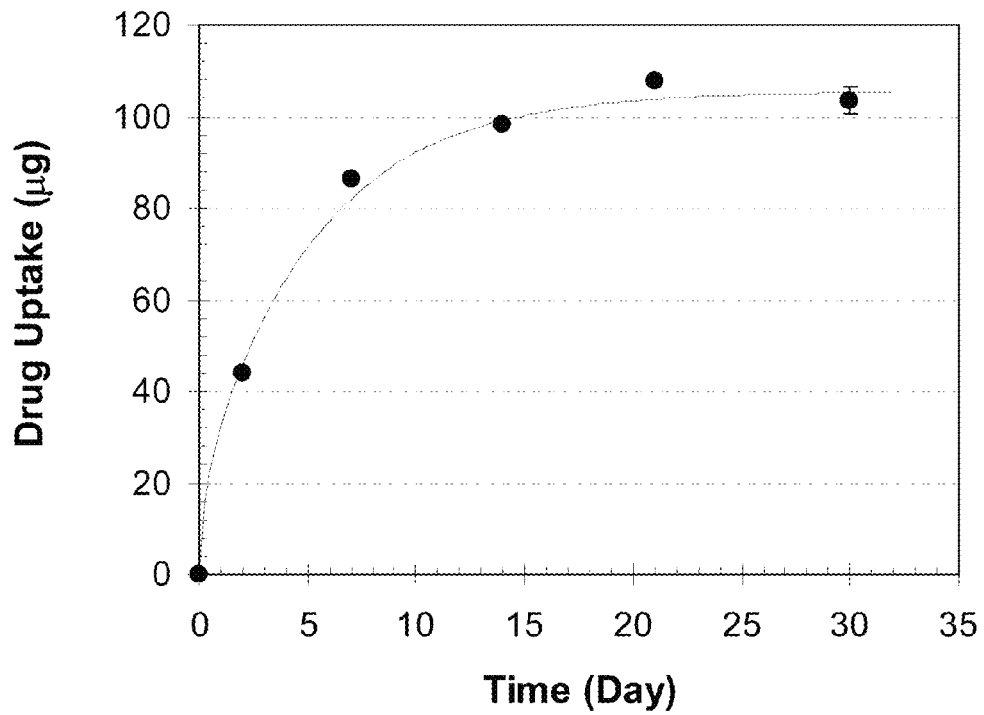
FIGS. 9A-9B show A) equilibrium plot and B) correlation of absorbance versus wavelength for CyA uptake by ACUVUE® OASYS™ for lenses soaked in 17 mg/ml of CyA/PBS solutions.
Figure 9B:
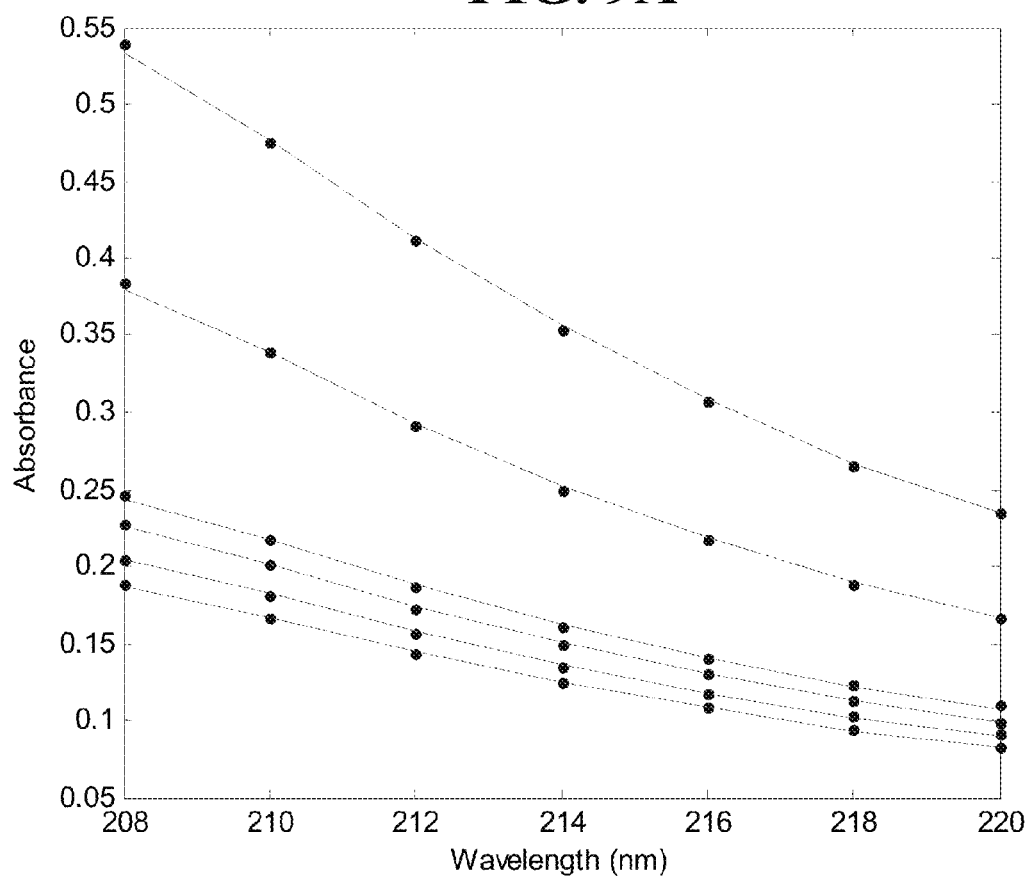

By measuring the initial and final CyA concentration of the loading experiments, the partition coefficient of CyA in the lens (K) can be obtained through the following equation $$K = \frac{C_{pl,f}}{C_{w,f}} = \frac{V_w(C_{w,i} - C_{w,f})}{V_{pl}C_{w,f}} \quad (3)$$

where $V_w$ and $V_{pl}$ are the volumes of the drug-PBS solution and the dry pure lens, respectively, and $C_{pl,f}$, $C_{w,i}$ and $C_{w,f}$ are the final concentrations of the drug in the lens phase, and the initial and final concentrations in the aqueous phase, respectively, in the loading experiment. The calculated partition coefficients for different commercial contact lenses after 7-days loading process are listed in Table 4. The drug partition coefficients are high for each lens and are highest for PureVision™, followed by NIGHT&DAY™, O₂OPTIX™ and ACUVUE® OASYS™, while 1-Day ACUVUE® has the lowest partition coefficient which is one order less than the others. Since CyA is a highly hydrophobic drug with very limited solubility in PBS, it is expected to observe high partition coefficient value for hydrogel contact lenses. 1-Day ACUVUE® is a daily disposable soft contact lens based on hydrophilic pHEMA hydrogel, while the other four contact lenses used in this study are silicone hydrogel lenses that contain hydrophobic silicone-rich region in the contact lens matrix. Therefore, it is expected to observe higher CyA partition coefficient for these extended-wear silicone contact lenses. The total amount of drug uptake for each lens is listed in Table 4. For 1-Day ACUVUE®, about 94% of CyA in the initial drug solution remained in PBS medium after soaking for 7 days, while silicone hydrogel lenses took the majority of CyA (51.6% to 75.6%) from the PBS solution into the gel matrix, leading to less drug waste after the loading process. The results suggest that the approach of loading CyA by soaking contact lens in drug solution is more efficient for silicone hydrogel lenses than hydrophilic pHEMA lenses. The partition coefficients obtained here are possibly less than the true equilibrium partition coefficients because the equilibrium was not established within 7 days. To address this issue, equilibrium studies were conducted by soaking 7 pure ACUVUE® OASYS™ lenses (dry weight=22.3±0.3 mg) into 10 ml of 17 µg/ml CyA/PBS solutions for different period of time, then measured the drug uptake by estimating the remaining CyA concentration of soaking solution with UV-VIS spectrophotometer. For each sample, no replacement of fresh PBS was conducted during the soaking process and the results are shown in FIG. 9. FIG. 9A indicates that CyA concentrations between PBS medium and ACUVUE® OASYS™ reaches equilibrium after about 10 days, and the final equilibrium partition coefficient is 677.5±48.9 after soaking the lens into drug solution for 30 days. During the drug loading process, the measured UV absorbance spectrums at different time are linearly dependent to the pre-established correlation within the wavelength range of interest, which is shown in FIG. 9B. The good fitting indicates that no spectrum deformation occurs, which implies that there is no drug degradation during the entire drug loading experiments.

Figure 10:
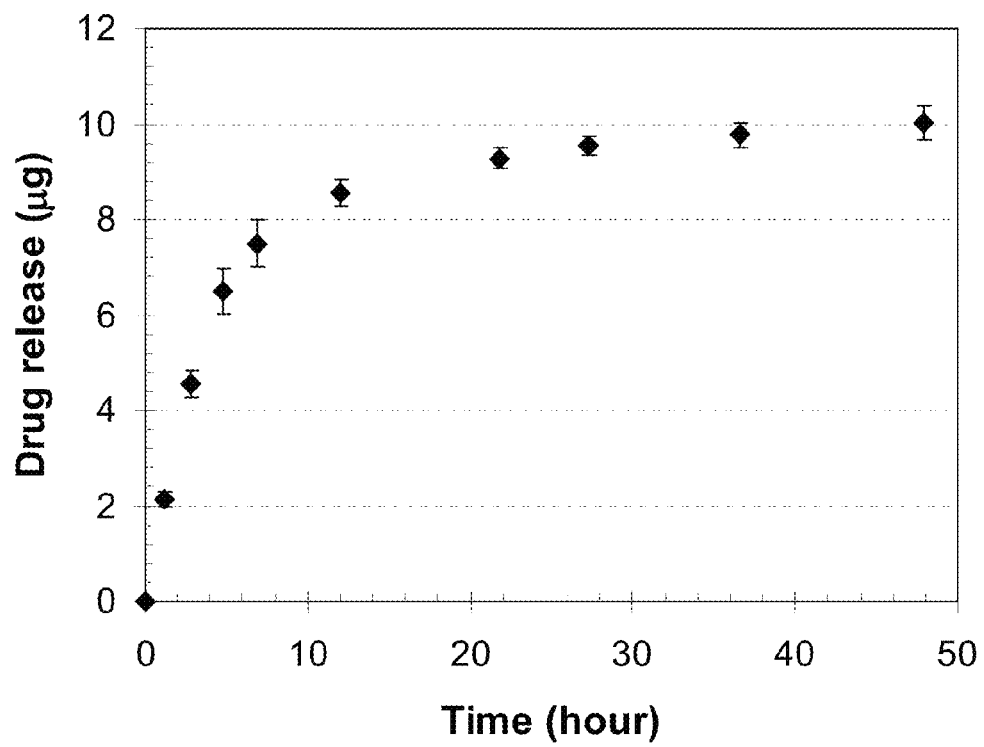
FIG. 10 shows the CyA release profile by 1-Day ACUVUE® with data plotted as mean±SD (n=3).

FIG. 10 shows the results of CyA release by 1-Day ACUVUE® at perfect sink condition. After around 24 hours, the included CyA in the lens was completely released into PBS medium, and the results suggested that 7 days is long enough for 1-Day ACUVUE® to reach drug equilibrium between lens and PBS medium. Since these hydrophilic pHEMA hydrogel contact lenses are designed for daily wear, the CyA release duration by 1-Day ACUVUE® should be sufficient.

Figure 11A:
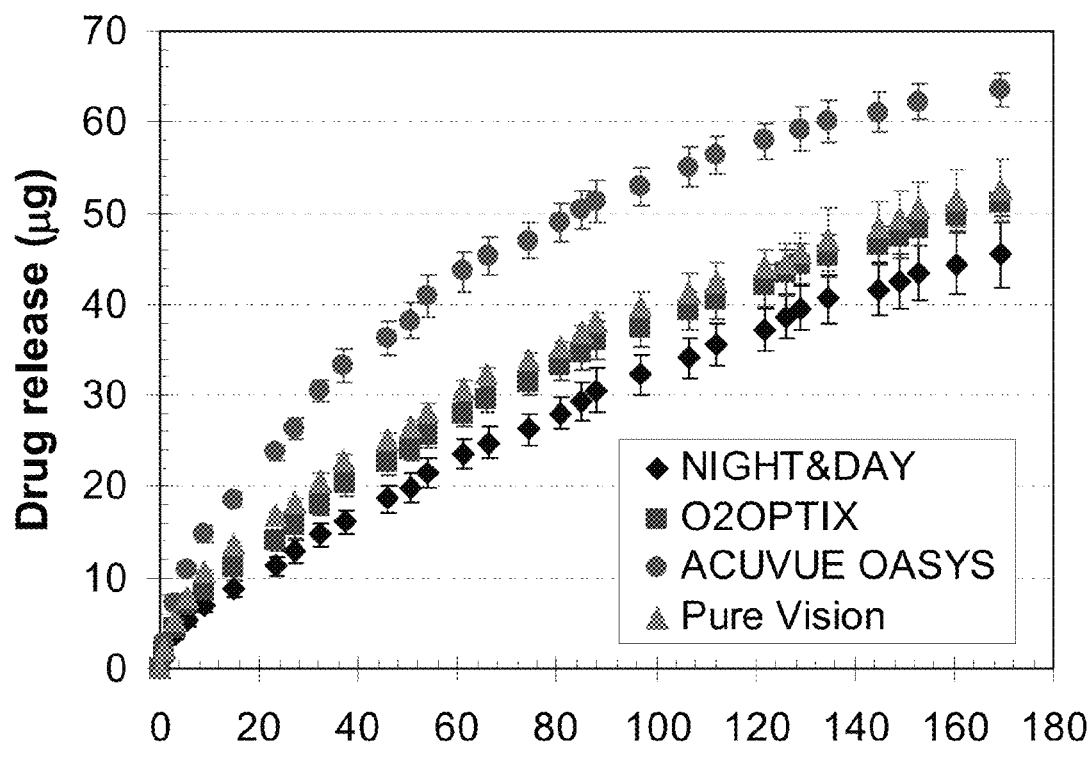
FIGS. 11A-11B shows the CyA release profile by silicone contact lens for samples soaked in 10 mg of 15 µg/ml CyA/PBS solution for 7 days with data plotted as mean±SD (n=3).
Figure 11B:
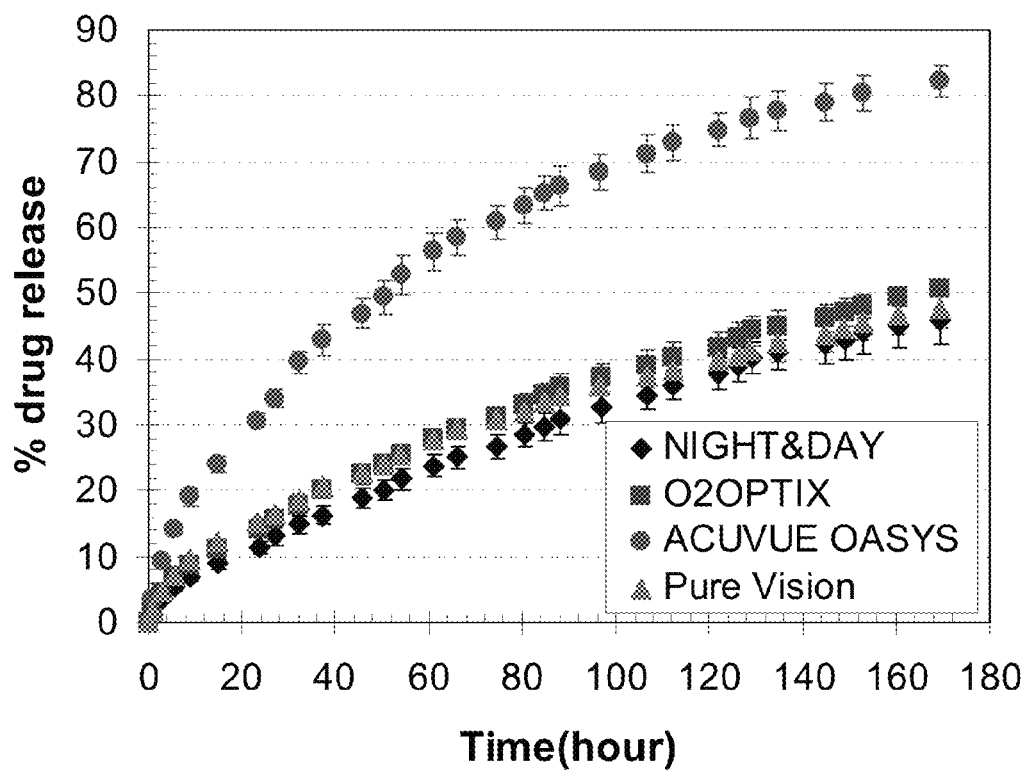

The cumulative mass of drug released under perfect sink conditions is plotted as a function of time for silicone contact lenses in FIG. 11A. It is clear that all these four commercial silicone contact lens release CyA for extended period lasting more than 7 days, which is significantly longer than the release duration by p-HEMA hydrogel lenses. The % release profiles are plotted in FIG. 11B, and the data shows that after 7 days, ACUVUE® OASYS™ lens releases about 82% of the loaded CyA, and the other three types of lenses release about 50% of the loaded drug. These results show that the time required for achieving equilibrium during the loading phase is longer than 7 days and thus the partition coefficients in Table 4 are underestimated and the difference between the true equilibrium K values and those reported in Table 4 should be smallest for ACUVUE® OASYS™ as its equilibration time is only slightly larger than 7 days as evident from the 82% release in 7 days. The ACUVUE® OASYS™ lens releases about 15 µg of drug each day and the other three types of lenses release about 10 µg CyA each day. Currently, CyA is delivered through 2-drops per day of oil-in-water emulsion (Restasis®, Allergan) that deliver about 28 µg (assuming a drop volume of 28 µl) of drug to the eye. It was recently determined that the bioavailability of CyA delivered through Restasis® to be 2.8%, indicating that about 0.78 µg/day of CyA is delivered to cornea and conjuntiva through this treatment route. On the other hand, the residence time and bioavailability of drugs delivered through contact lenses are much higher than those for eye drops, as the bioavailability can be as high as around 50%, 10 µg/day of CyA should be sufficient for therapeutic effects. If higher release rates are desired, the amount loaded into the lenses can be increased by increasing the concentration of drug in the loading solution and increasing the total loading time to allow the system to reach equilibrium. Also alternate approaches such as loading in solutions with high solubility of CyA could be used.

TABLE 4

Results of CyA uptake by silicone contact lens. Each lens was soaked in 10 ml of 15 µg/ml CyA-PBS solution for 7 days. Data are shown as mean ± SD (n = 3).

|  | $V_{pl}$ (ml) | CyA Uptake (µg) | Partition Coefficient, K |
|---|---|---|---|
| 1-Day ACUVUE ® | 0.0224 ± 0.0004 | 9.0 ± 2.7 | 31.6 ± 10.3 |
| NIGHT&DAY ™ | 0.0224 ± 0.0005 | 98.7 ± 4.9 | 909.8 ± 118.1 |
| O₂OPTIX ™ | 0.0249 ± 0.0003 | 100.4 ± 2.3 | 858.4 ± 58.8 |
| ACUVUE ® OASYS ™ | 0.0227 ± 0.0002 | 77.4 ± 2.4 | 485.6 ± 30.2 |
| Pure Vision ™ | 0.0224 ± 0.0003 | 110.4 ± 2.5 | 1331.1 ± 103.8 |

Example 11

Drug Loading into Vitamin E Loaded Commercial Contact Lenses

Drug containing Vitamin E loaded lenses were prepared by directly adding drug to a Vitamin E-ethanol solution before soaking the pure lens in the solution, or by soaking a Vitamin E loaded lens in a drug-PBS solution. Drug containing Vitamin E-ethanol solutions were prepared by dissolving the drug in 3 ml of a Vitamin E-ethanol solution and then pure lens were soaked in this drug/Vitamin E-ethanol for 24 hours. The drug containing Vitamin E-ethanol lenses were taken from the solution blotted with wipes and dried overnight before subsequent release experiments. For the lenses loaded by soaking in a drug-PBS solution, Vitamin E loaded lenses were soaked in 2 ml of a drug-PBS solution until equilibrium was established. The total amount of drug loaded into the lens was determined by difference, being the total amount of drug lost from the aqueous solution as measured the absorbance spectra of the final solution after loading by monitoring the wavelength of 241 nm for DX and DXP, 294 nm for timolol, 300 nm for KF, and 208-220 nm for CyA using a UV-VIS spectrophotometer (Thermospectronic Genesys 10 UV).

Example 12

Drug Release from Commercial Contact Lenses

The drug release experiments were carried out by soaking a drug loaded lens in 2 ml of PBS, except for CyA loaded lens that were soaked in 1.75 ml of PBS. During the release experiments, the dynamic drug concentration in the PBS was analyzed by measuring the absorbance of solution with a UV-VIS spectrophotometer (Thermospectronic Genesys 10 UV). The absorbance of solution was measured at wavelength of 241 nm for DX and DXP, 294 nm for timolol, 210 nm for fluconazole, 300 nm for KF and 208-220 nm for CyA. Control experiments were conducted to ensure that diffusion of Vitamin E from the lenses was negligible and so it did not interfere with the drug detection.

Example 13

Effect of Vitamin E Loading on Timolol Uptake by Silicone-Hydrogel Lenses

Figure 12:
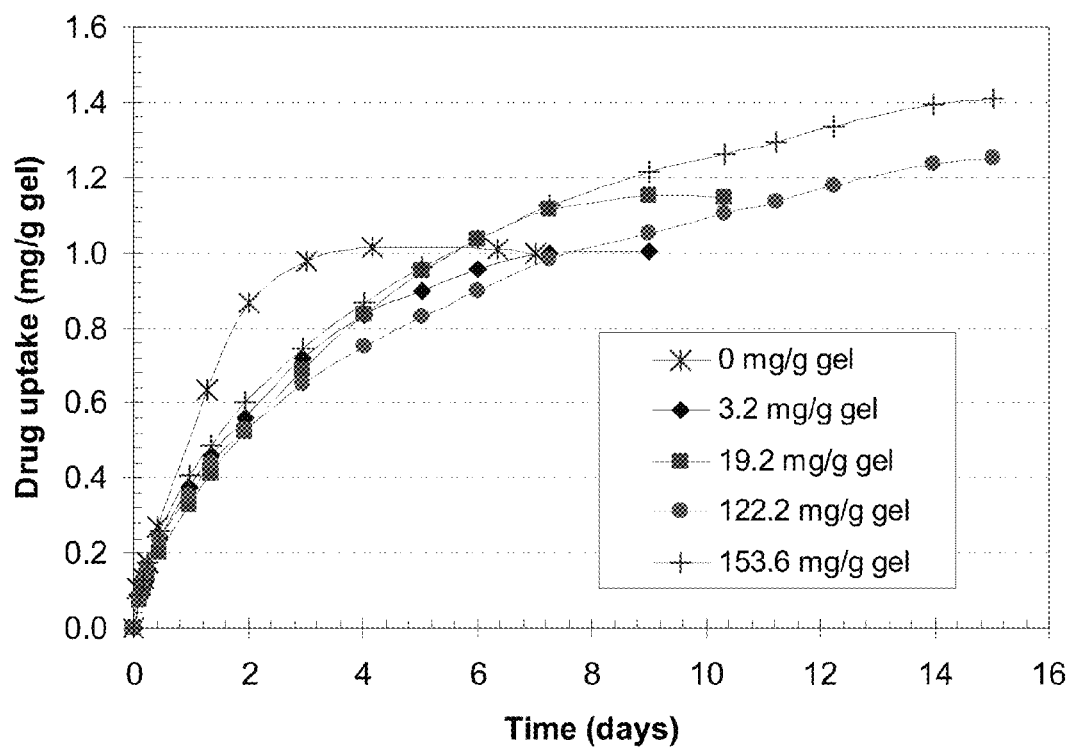
FIG. 12 shows a plot of timolol uptake into a contact lens as a function of the concentration of Vitamin E in the lens.

FIG. 12, displays a plot of timolol uptake for silicone-hydrogel contact lenses described in Example 1 of thickness of about 150 microns that contain Vitamin E at 5 different loadings, where the Vitamin E loadings are indicated as milligrams of Vitamin E per gram of lens, where the total mass of lens is the silicone-hydrogel lens and absorbed Vitamin E. For example, the silicone-hydrogel with highest Vitamin E loading (153.6 mg/g) takes up more than 40% more timolol than does the control silicone-hydrogel free of Vitamin E. The rate of drug uptake by the silicone-hydrogels decreases as the Vitamin E loading increases. For example, the silicone-hydrogel with highest Vitamin E loading (153.6 mg/g) required more than 15 days to reach a maximum timolol uptake, while the control gel required only 4 days.

Example 14

Effect of Vitamin E Loading on CyA Uptake by Vitamin E Loaded Contact Lens

Figure 13:
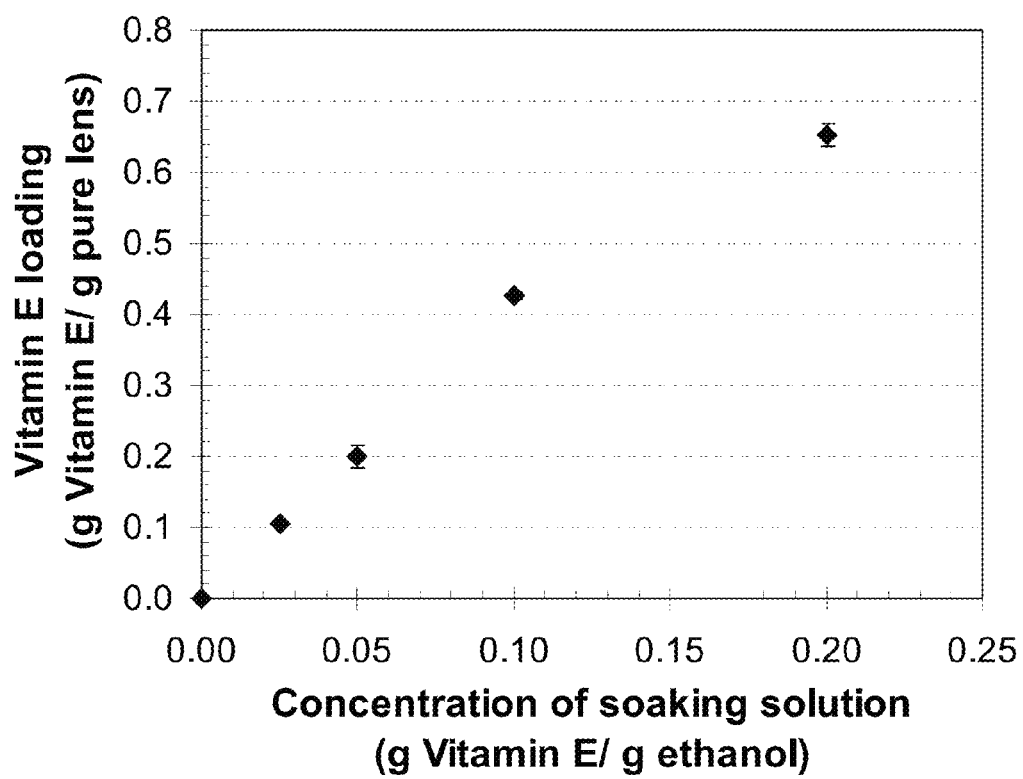
FIG. 13 shows relationship between Vitamin E loading amount in ACUVUE® OASYS™ to the CyA concentration of soaking solution with data plotted as mean±SD (n=3).

To investigate the effect of Vitamin E loading to the CyA uptake by contact lens, ACUVUE® OASYS™ lenses were soaked in Vitamin E/ethanol solution with various concentrations, and the results are shown in FIG. 13. The Vitamin E loading amount was determined by measuring the weight of dry lens before and after loading Vitamin E into the lens. The results show a linear correlation of Vitamin E loading in the lens to the concentration of Vitamin E loading solutions. The results of drug uptake by ACUVUE® OASYS™ lenses with various Vitamin E loading are listed in Table 5. Adding Vitamin E into the contact lens matrix significantly increases the CyA uptake from CyA/PBS solutions and after 120 days 99% of the drug in the initial soaking solution was taken into the contact lens with about 40% Vitamin E loading. Since the equilibrium CyA partition coefficient of pure ACUVUE® OASYS™ was known estimates of the CyA partition coefficient of the Vitamin E phase in the lens (Kve) were made as given in Table 5. The calculated Kve from lenses with different various Vitamin E loadings are similar for different durations of soaking, which suggests that all these samples reach CyA equilibrium between gel matrix containing Vitamin E and PBS medium. The average Kve for CyA is about 20-fold higher than the partition coefficient of pure hydrogel matrix of ACUVUE® OASYS™, which implies that the hydrophobic CyA has a much higher affinity for the Vitamin E phases than for the silicone gel matrix. Vitamin E loaded silicone hydrogel contact lenses have been shown to provide sufficient ion and oxygen permeability to serve as extended-wear ophthalmic drug delivery vehicle, and, therefore, these results demonstrate that by including Vitamin E into the silicone hydrogel matrix, the CyA loading amount can be significantly enhanced without scarifying other critical physical properties needed for the extended wearing of these contact lenses.

TABLE 5

Results of CyA uptake by Vitamin E loaded ACUVUE ® OASYS ™ lenses. Each lens was soaked in 10 ml of 17 µg/ml CyA-PBS solution for various drug uptake durations. Data were shown as mean ± SD (n = 3).

| Vitamin E loading (g Vitamin E/g pure lens) | Drug uptake duration (days) | Drug uptake (µg) | K | Kve |
|---|---|---|---|---|
| 0 | 30 | 103.4 ± 3.1 | 677.50 |  |
| 0.106 | 45 | 134.2 ± 1.3 | 1576.46 | 11492.00 |
| 0.200 | 60 | 151.1 ± 5.4 | 2618.14 | 13268.21 |
| 0.426 | 120 | 160.4 ± 4.7 | 3702.80 | 11244.20 |
| 0.653 | 120 | 166.4 ± 0.7 | 6095.36 | 14833.94 |

Example 15

Figure 14:
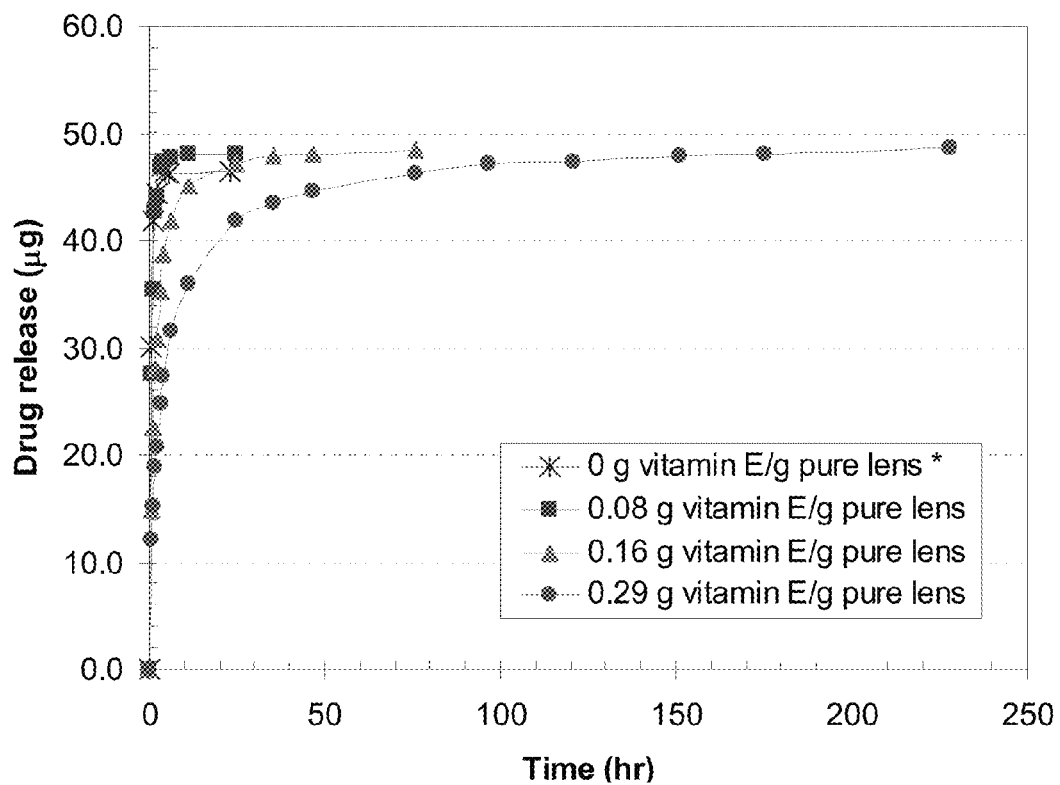
FIG. 14 shows a plot of the release of timolol from NIGHT&DAY™ contact lens loaded from a common ethanol solution of 0.8 mg timolol per mL of Vitamin E-ethanol solution as a function of the concentration of Vitamin E in the lens.
Figure 15:
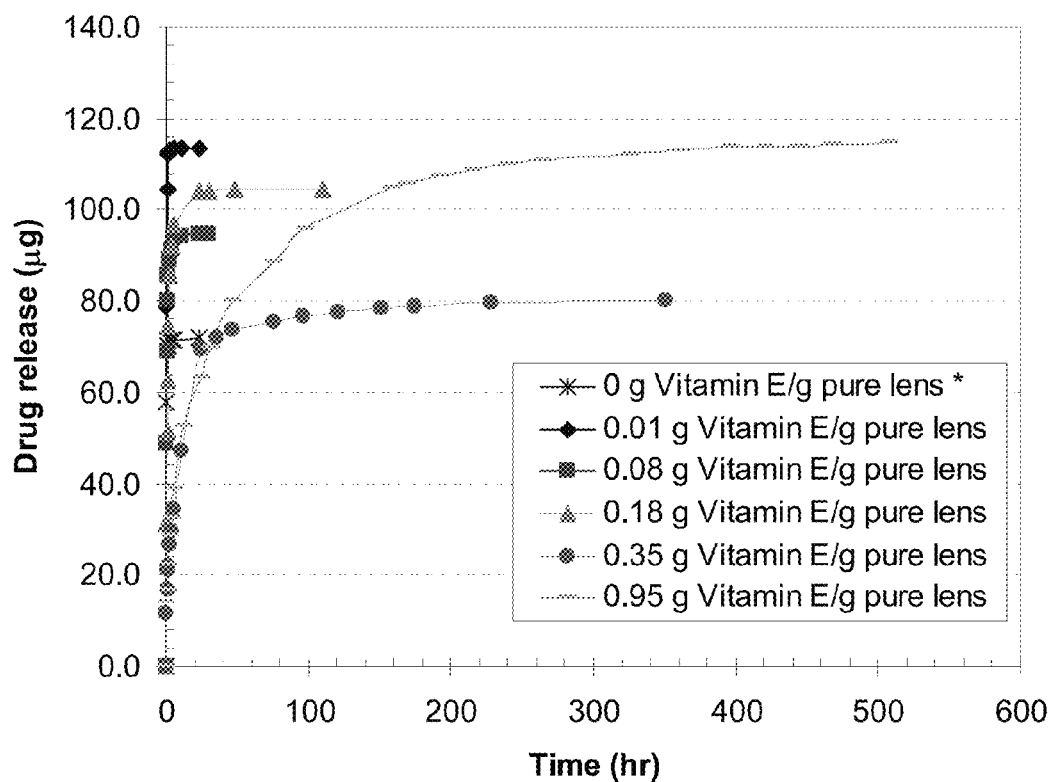
FIG. 15 shows a plot of the release of timolol from $O_2$OPTIX™ contact lens loaded from a common ethanol solution of 0.8 mg timolol per mL of Vitamin E-ethanol solution as a function of the concentration of Vitamin E in the lens.
Figure 16:
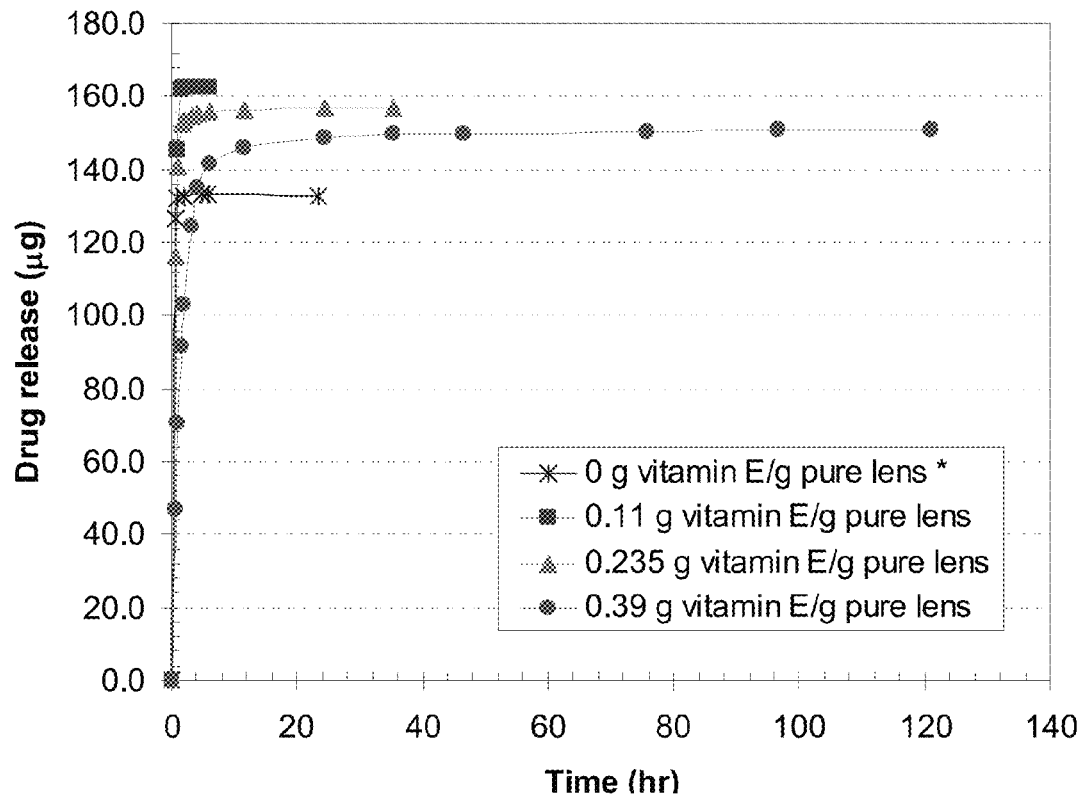
FIG. 16 shows a plot of the release of timolol from PureVision™ contact lens loaded from a common ethanol solution of 0.8 mg timolol per mL of Vitamin E-ethanol solution as a function of the concentration of Vitamin E in the lens.

Effect of Vitamin Loading on Drug (Timolol) Release from Silicone-Hydrogel Lenses The profiles of timolol release by various Vitamin E loaded contact lenses, which were soaked in timolol/Vitamin E-ethanol solution for 24 hours for simultaneous loading of the drug and nutraceutical, are shown in FIGS. 14 through 16 for NIGHT&DAY™, O₂OPTIX™, and PureVision™, respectively. As the Vitamin E loading increased, timolol release rates decreased. For example, as shown in FIG. 15, while the control O₂OPTIX™ Vitamin E free lens released timolol over a period of a single hour, the lens having a Vitamin E loading of 0.018 g Vitamin E/g released timolol for 6 hours, and a lens with 0.953 g of Vitamin E released timolol for more than 200 hours. In addition, the total amount of released drug increased as the Vitamin E loading increased. The trends are similar for other contact lenses.

Figure 17A:
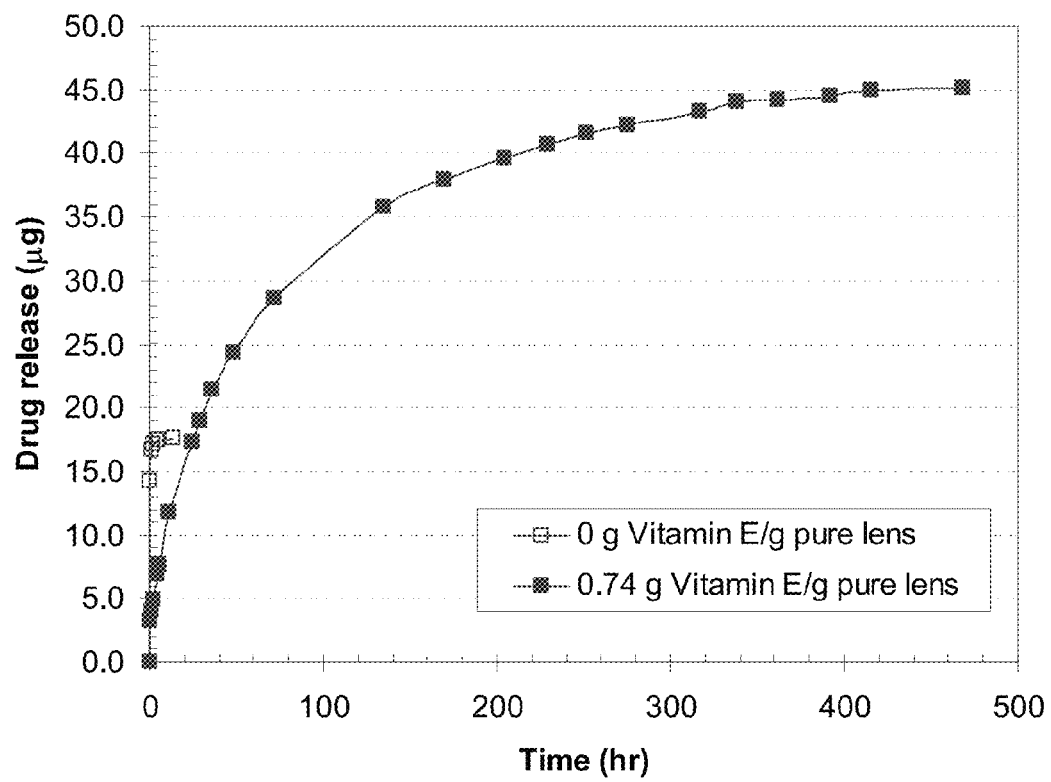
FIGS. 17A-17B shows plots of timolol release from (a) NIGHT&DAY™ or (b) $O_2$OPTIX™ contact lenses where the Vitamin E was loaded from an ethanol solution and timolol was subsequently loaded from a 0.8 mg/mL phosphate buffer solution (PBS) relative to the release from Vitamin E free lenses.
Figure 17B:
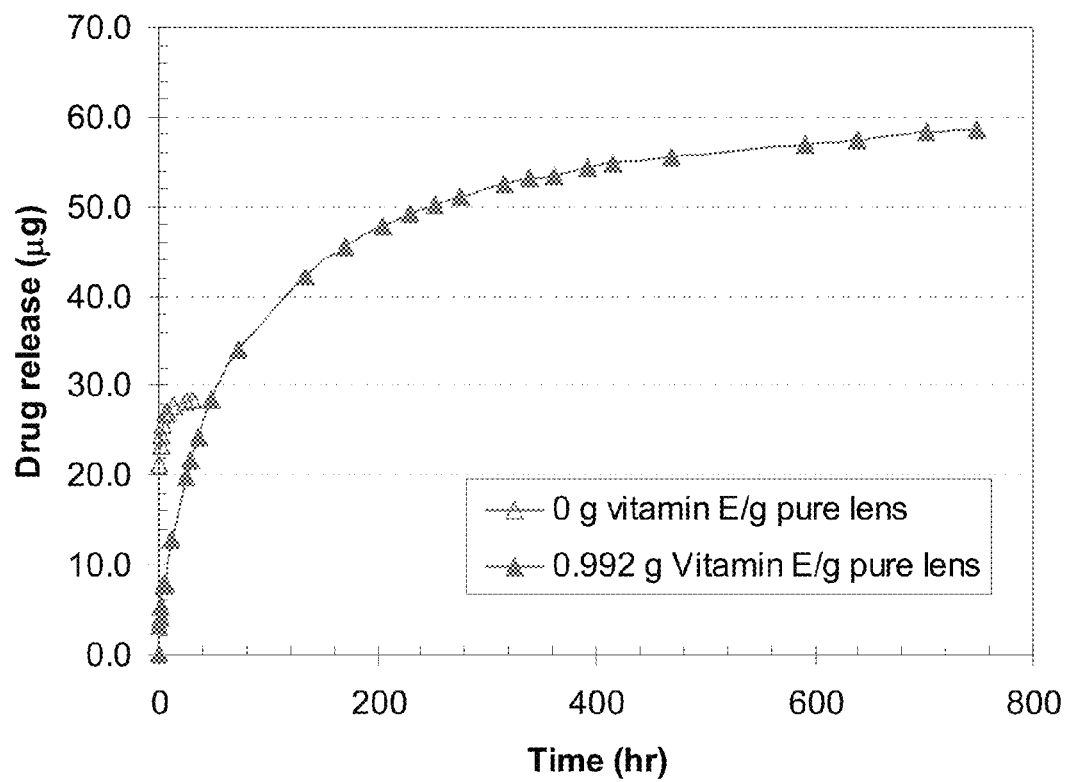

FIG. 17 shows plots of the effect of the Vitamin E loading on timolol release from various contact lenses where a two step mode to load the drug and nutraceutical diffusion attenuator was employed. The Vitamin E was loaded by soaking pure contact lens in Vitamin E-ethanol solution. Subsequently, the lens was dried and timolol was loaded into the dried Vitamin E loaded lenses by soaking in timolol-phosphate buffered saline (PBS) solution (0.8 mg/ml) for 7 days. Vitamin E loadings are indicated in the legend. When timolol was loaded by soaking the Vitamin E loaded silicone-hydrogel lens in a PBS drug solution, the timolol release occurs over a longer period than from timolol loaded nutraceutical free lens. However, the timolol released over any given time period was lower for the nutraceutical-free lenses than it was for the lenses containing Vitamin E.

Example 16

Figure 18A:
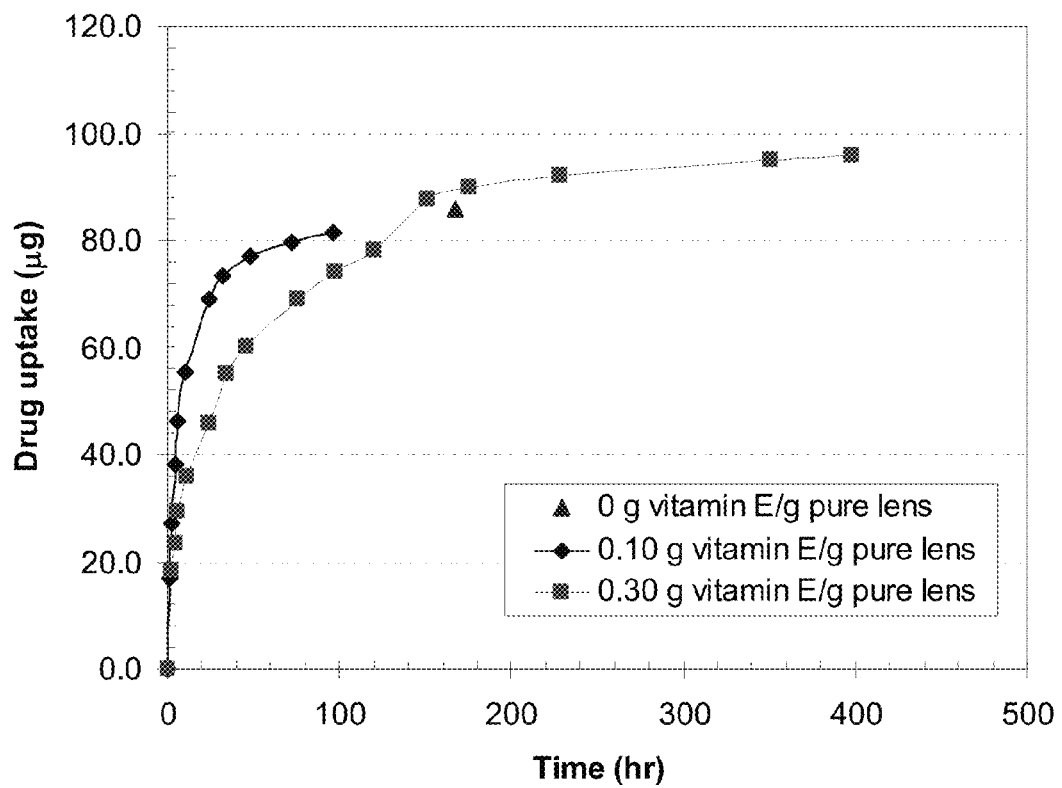
FIGS. 18A-18B shows plots of dexamthasone (a) uptake and (b) release from NIGHT&DAY™ contact lenses where the Vitamin E was loaded from an ethanol solution and dexamthasone was subsequently loaded from a 0.8 mg/mL phosphate buffer solution (PBS).
Figure 18B:
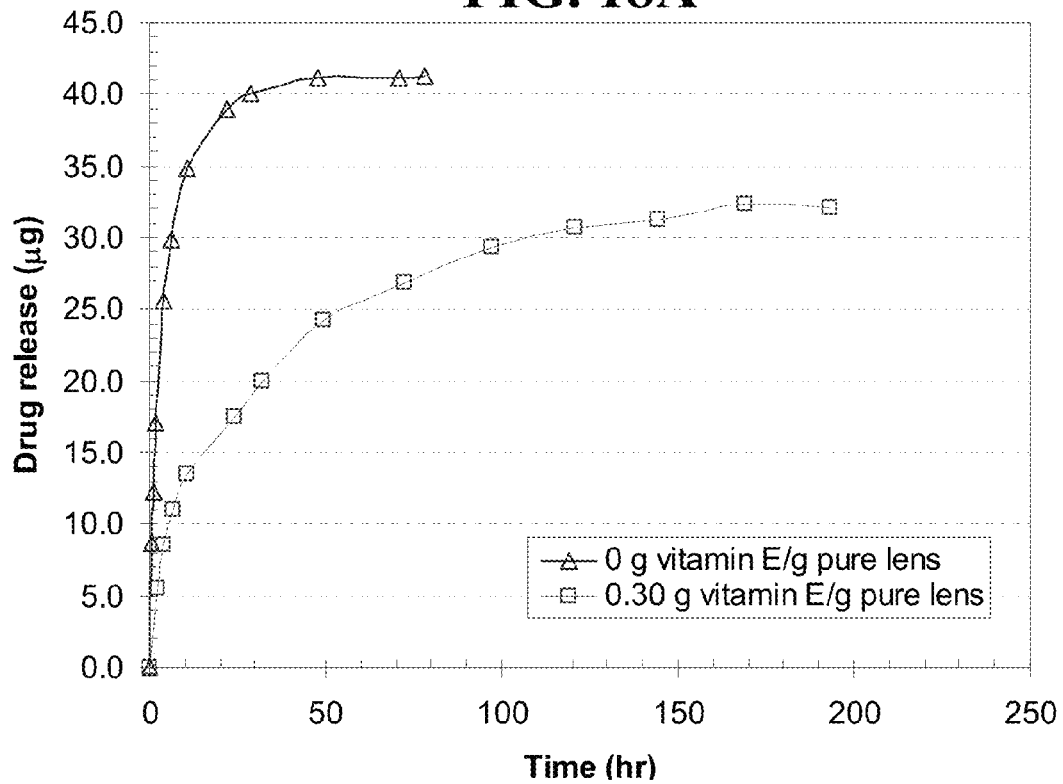
Figure 19A:
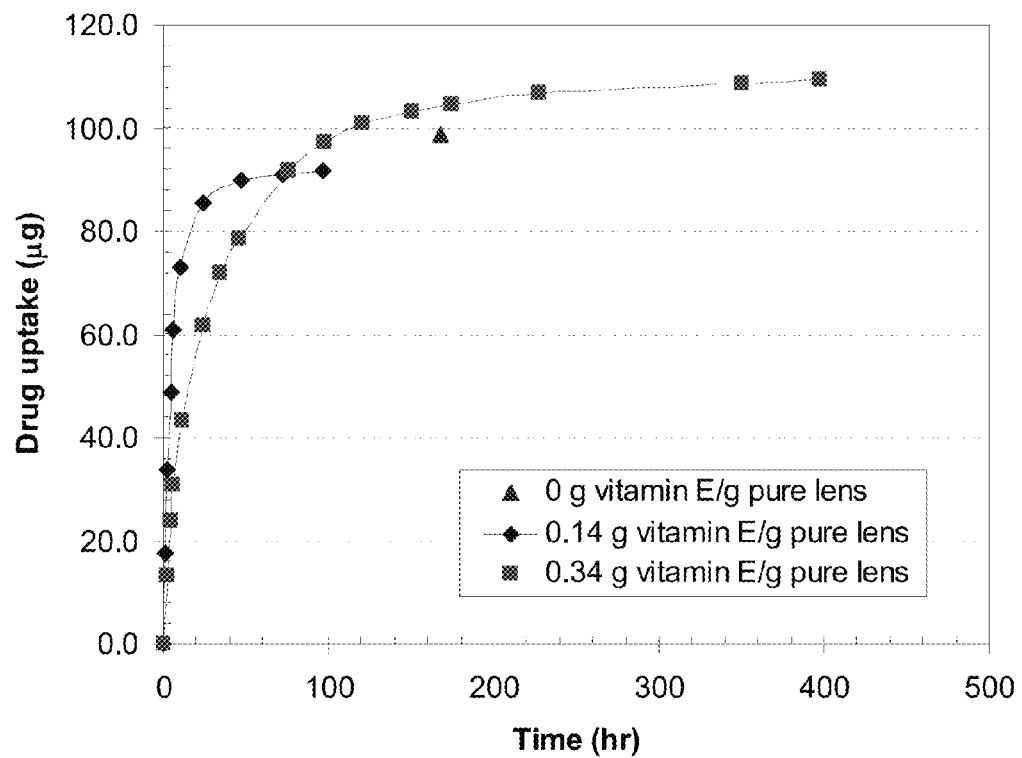
FIGS. 19A-19B shows plots of dexamthasone (a) uptake and (b) release from $O_2$OPTIX™ contact lenses where the Vitamin E was loaded from an ethanol solution and dexamthasone was subsequently loaded from a 0.8 mg/mL phosphate buffer solution (PBS).
Figure 19B:
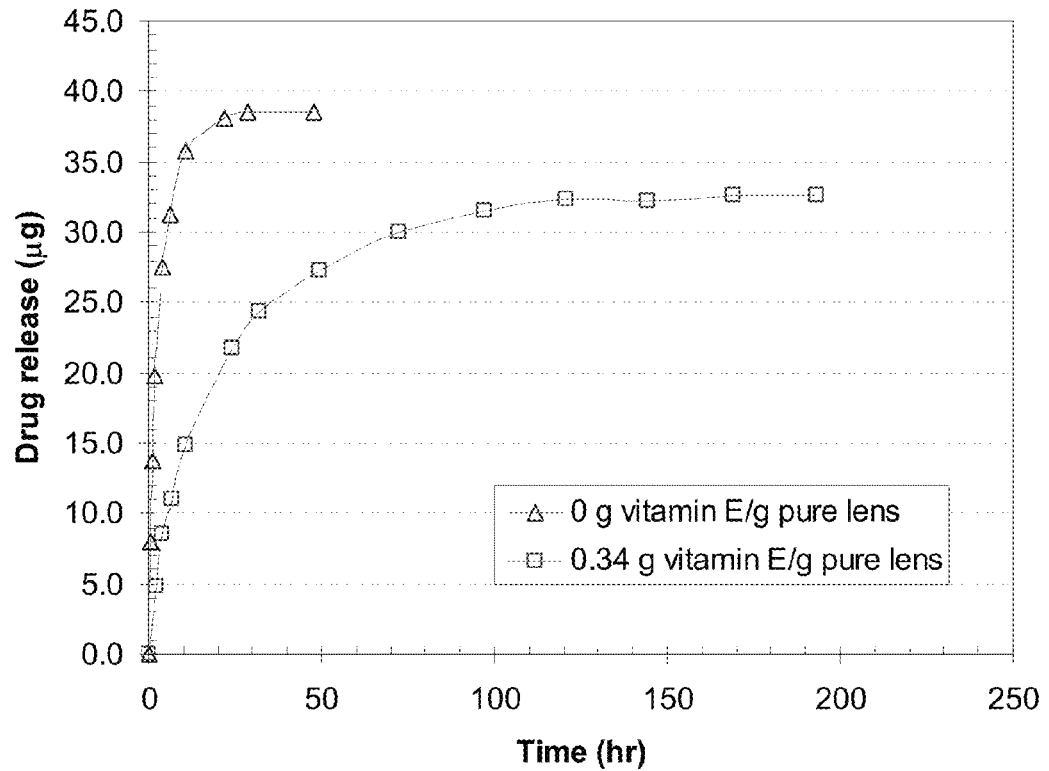
Figure 20A:
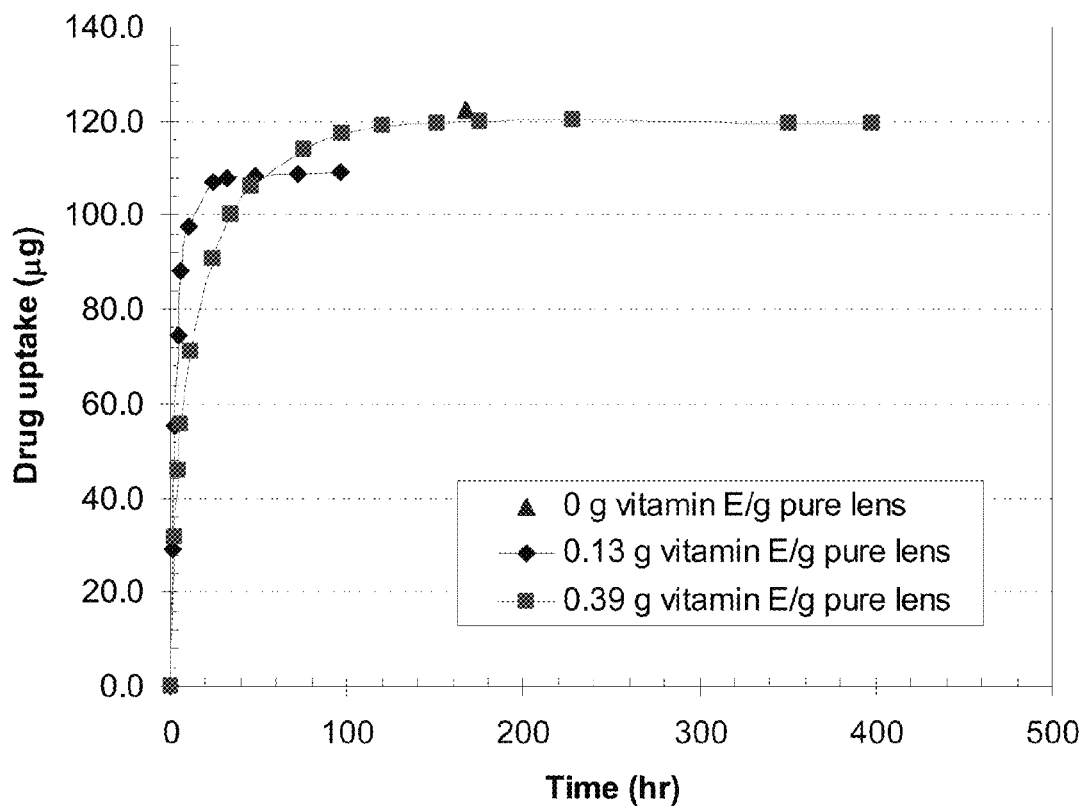
FIGS. 20A-20B shows plots of dexamthasone (a) uptake and (b) release from PureVision™ contact lenses where the Vitamin E was loaded from an ethanol solution and dexamthasone was subsequently loaded from a 0.8 mg/mL phosphate buffer solution (PBS).
Figure 20B:
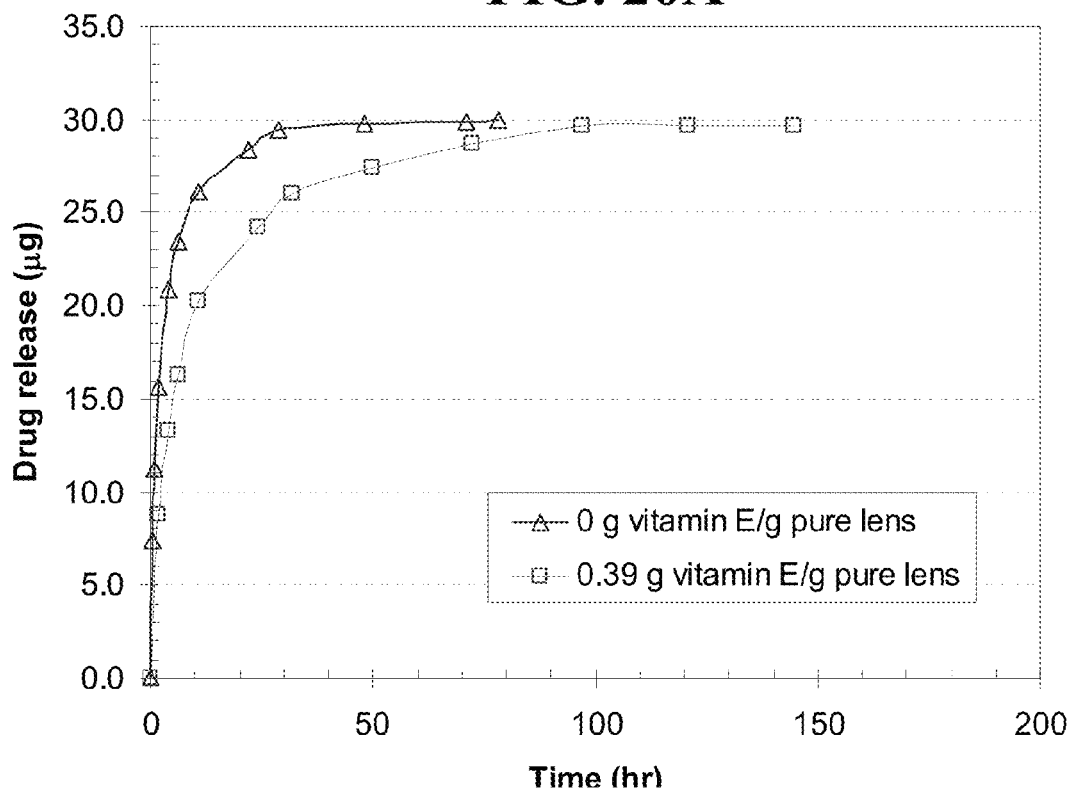
Figure 21A:
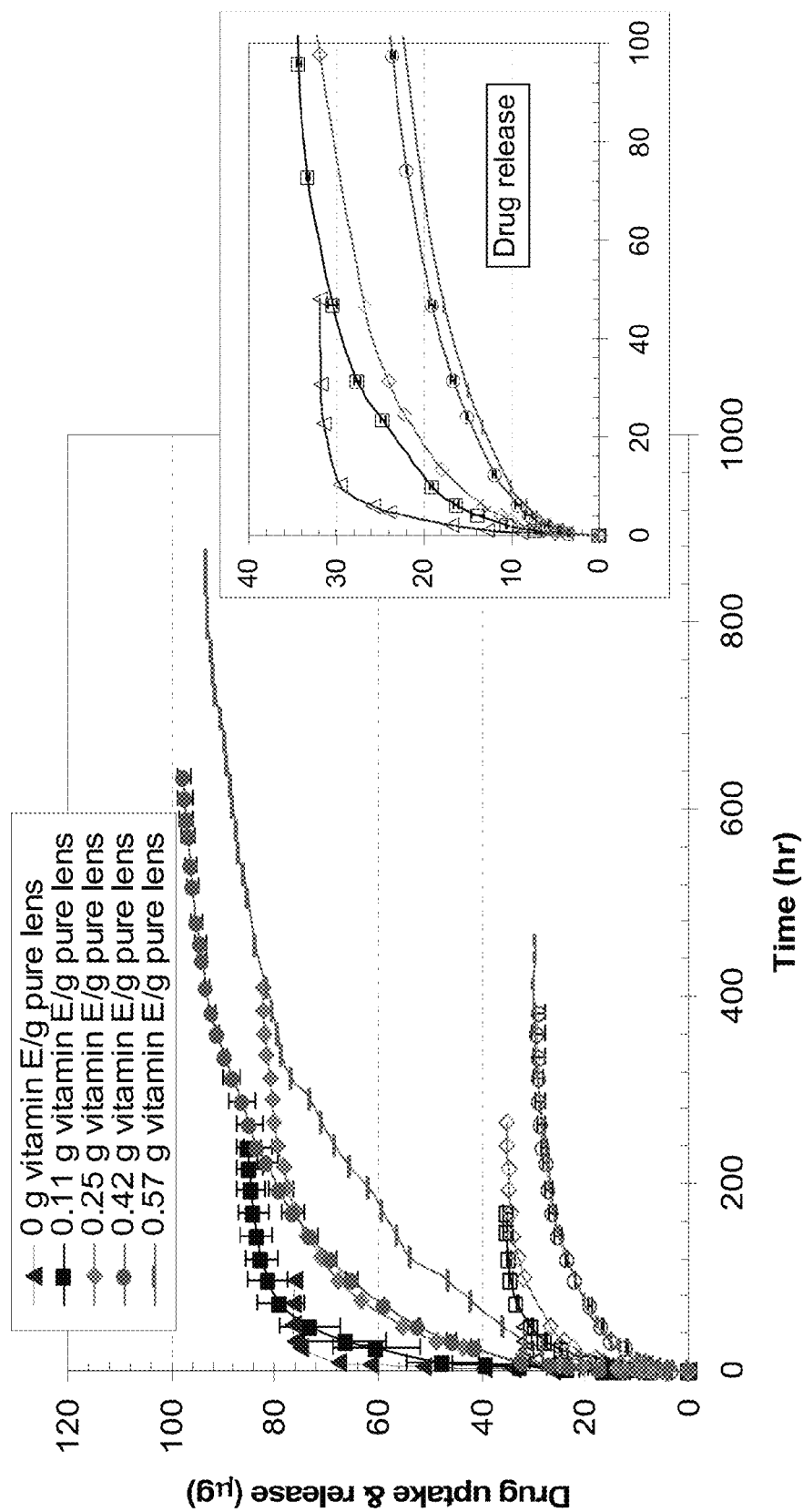
FIGS. 21A-21D shows plots for the uptake and release of DX from Vitamin E loaded contact lenses A) ACUVUE® OASYS™, B) NIGHT&DAY™, C) $O_2$OPTIX™, D) PureVision™ versus time where the lines with solid data points indicate uptake and hollow data points indicate release from lenses with the Vitamin E loadings indicated in the legend, where Vitamin E was loaded by soaking lenses in Vitamin E-ethanol solution, dried, and DX was loaded by soaking the Vitamin E loaded lens in DX-PBS solution (0.08 mg/ml), where data is presented as mean±SD with n=3 for Vitamin E loadings as indicated and where the inserts show magnified views of the plots for drug release during the initial hours.
Figure 21B:
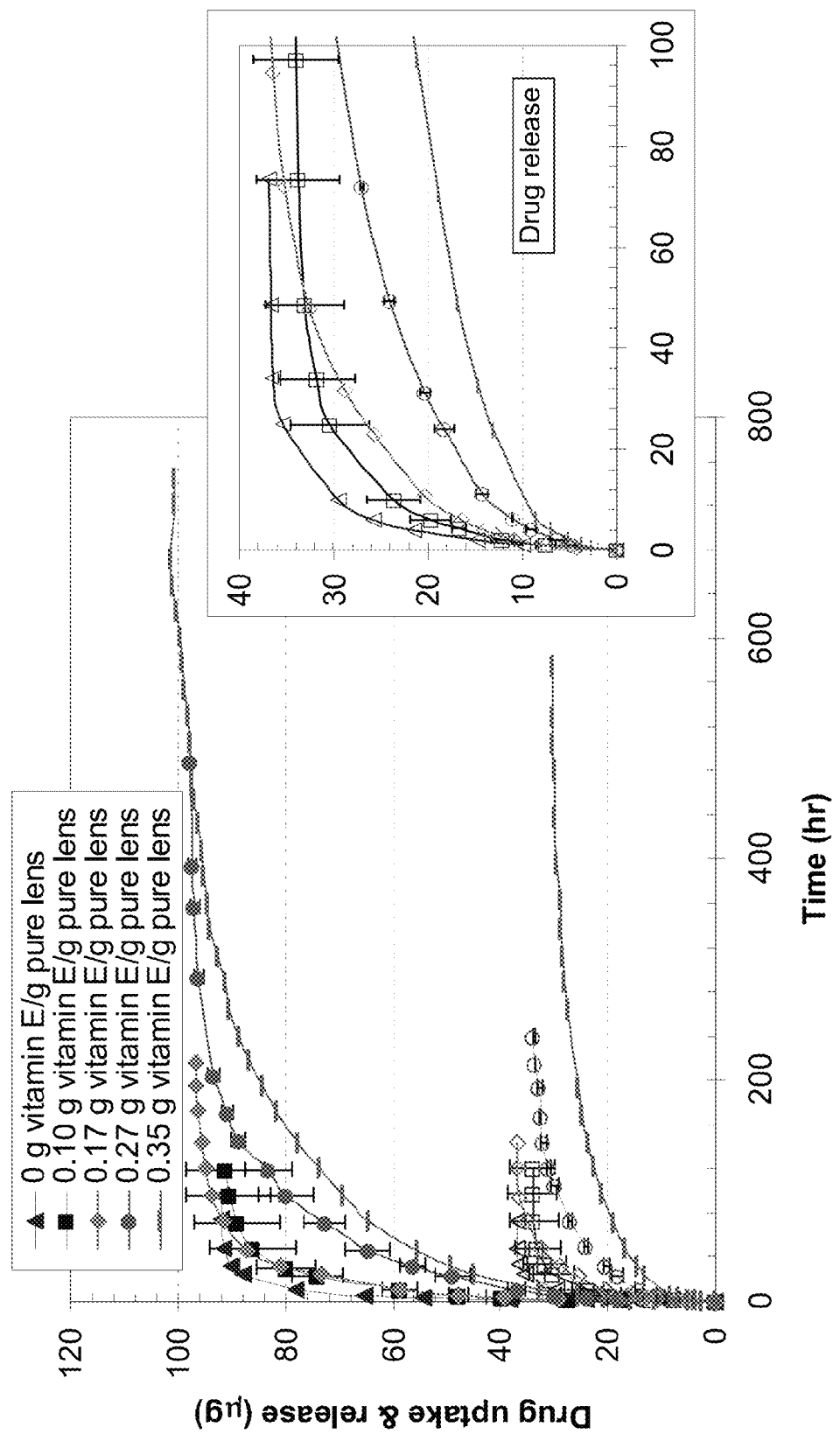
Figure 21C:
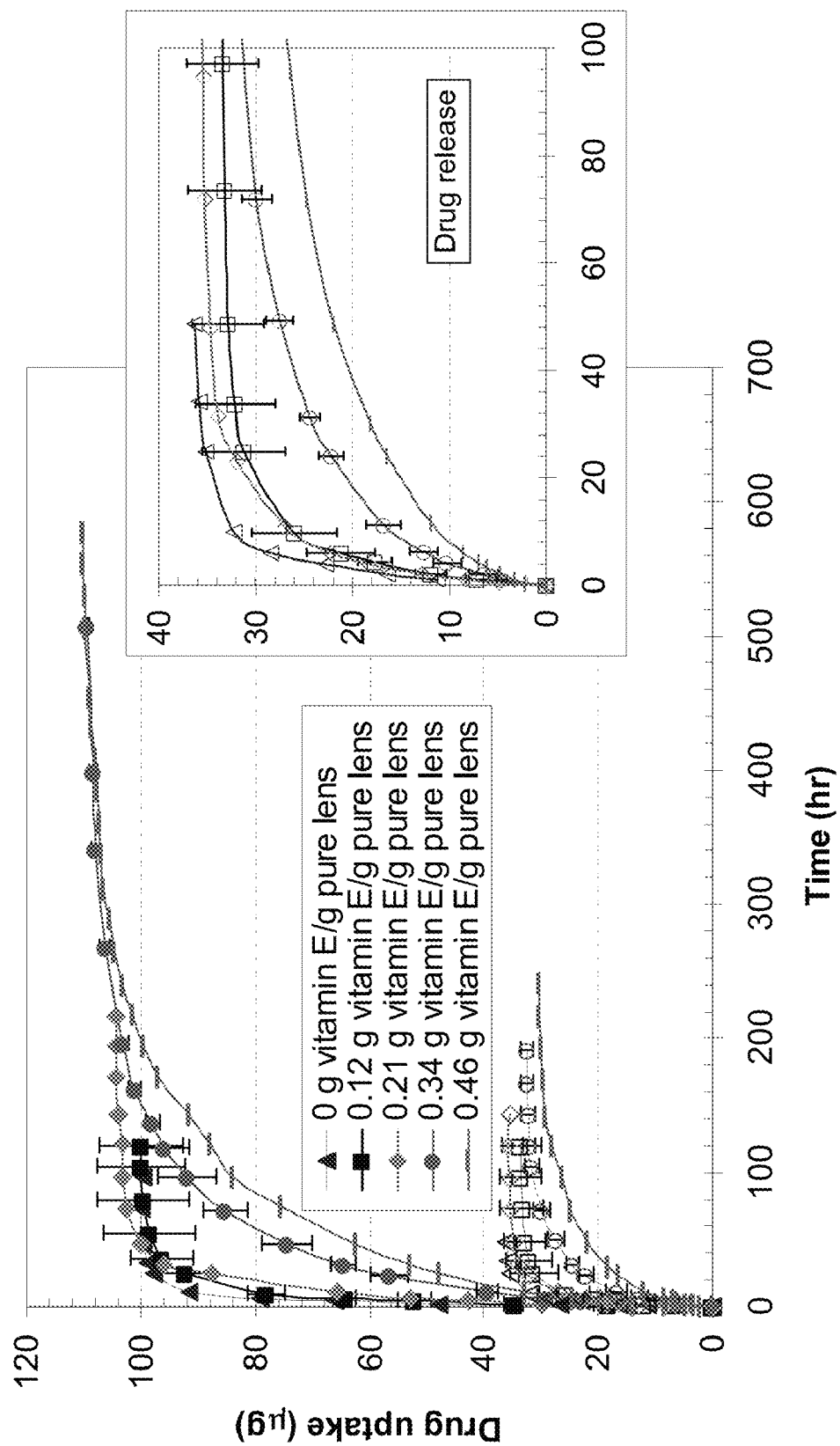
Figure 21D:
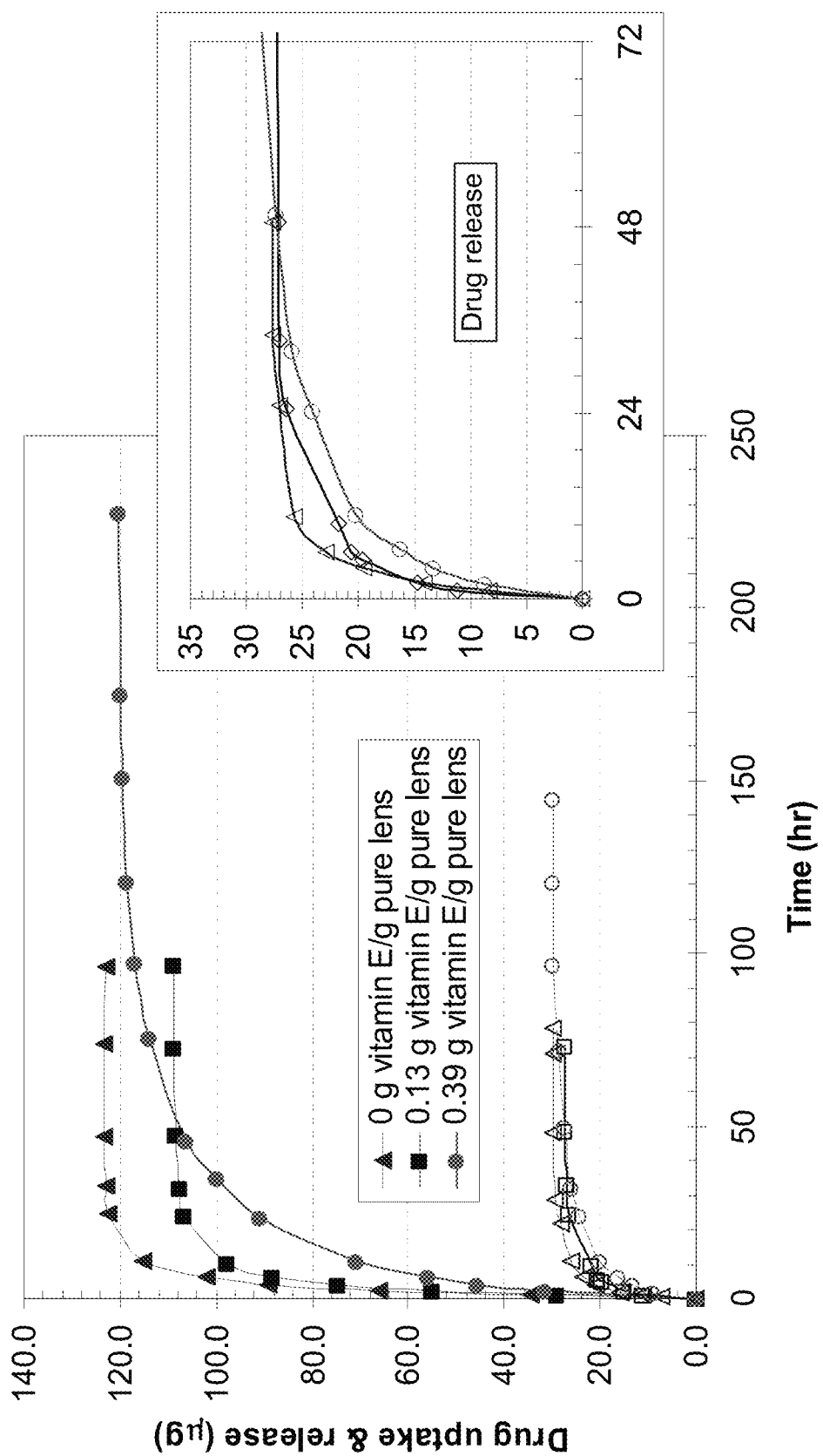
Figure 22A:
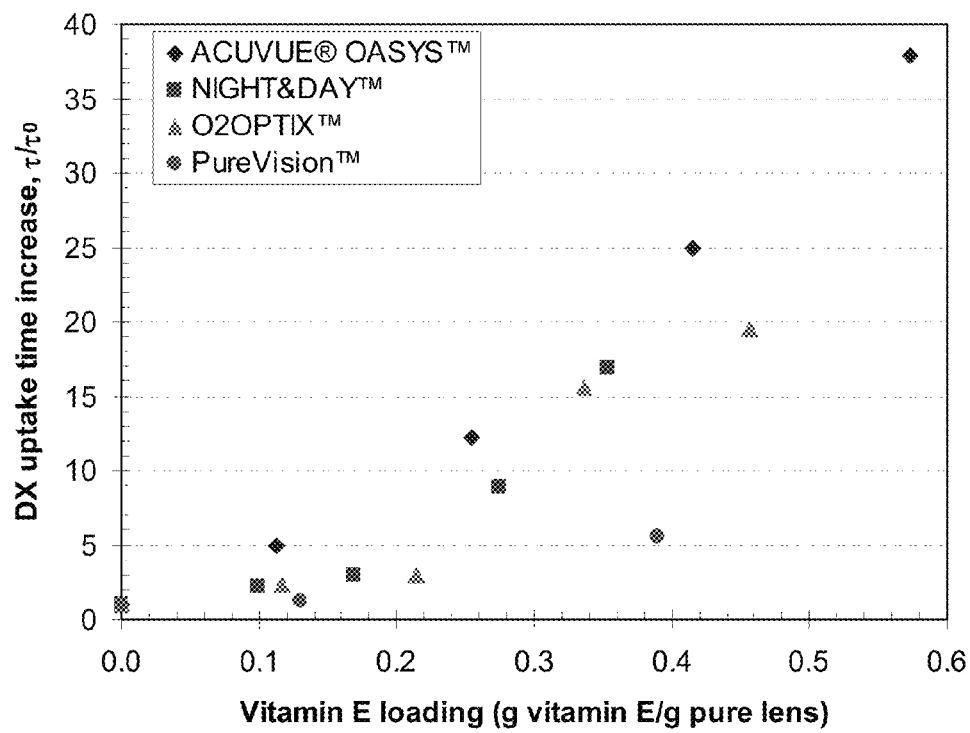
FIGS. 22A-22D shows plots of the DX uptake duration difference for various commercial contact lenses for A) various loadings of Vitamin E and C) various volume ratios, φ, of Vitamin E in the dry lens and DX release duration differences for various commercial contact lenses for B) various loadings of Vitamin E and D) various volume ratios, φ, of Vitamin E in the dry lenses where the identity of the lenses is given in the legend.
Figure 22B:
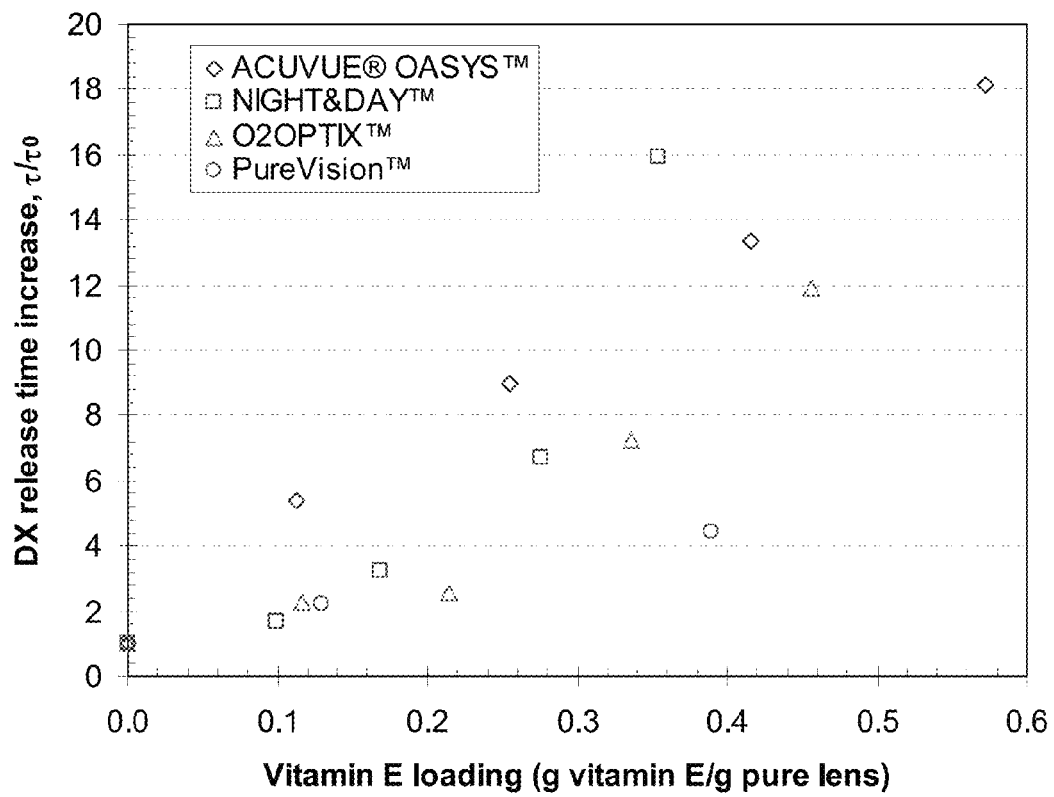
Figure 22C:
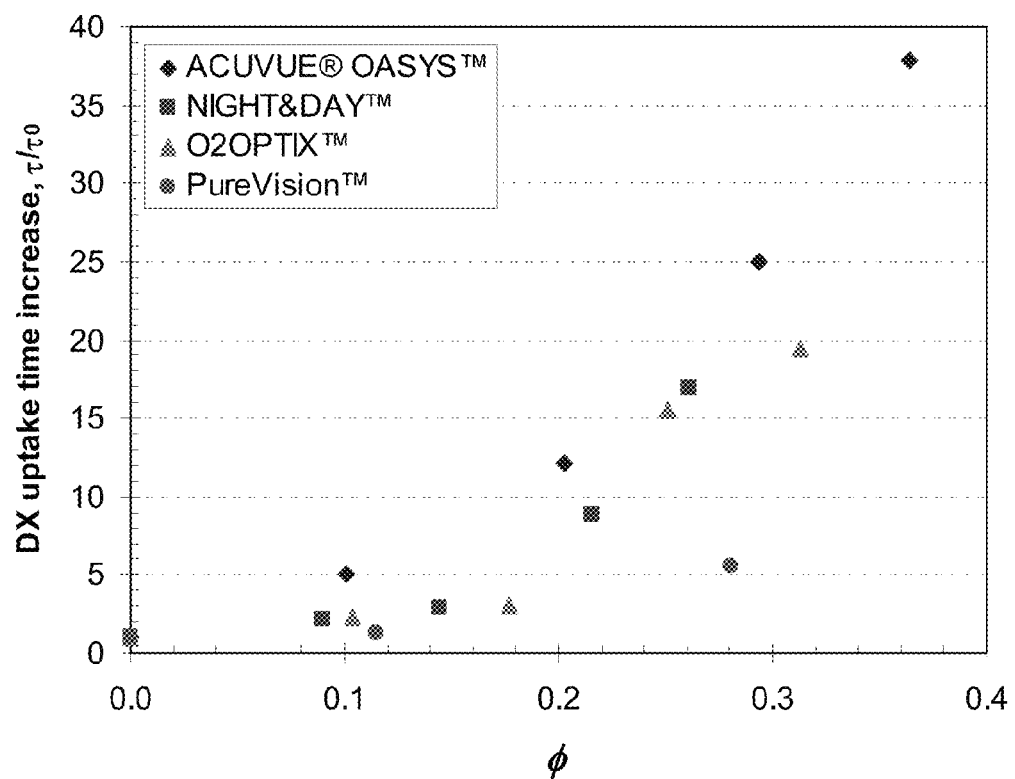
Figure 22D:
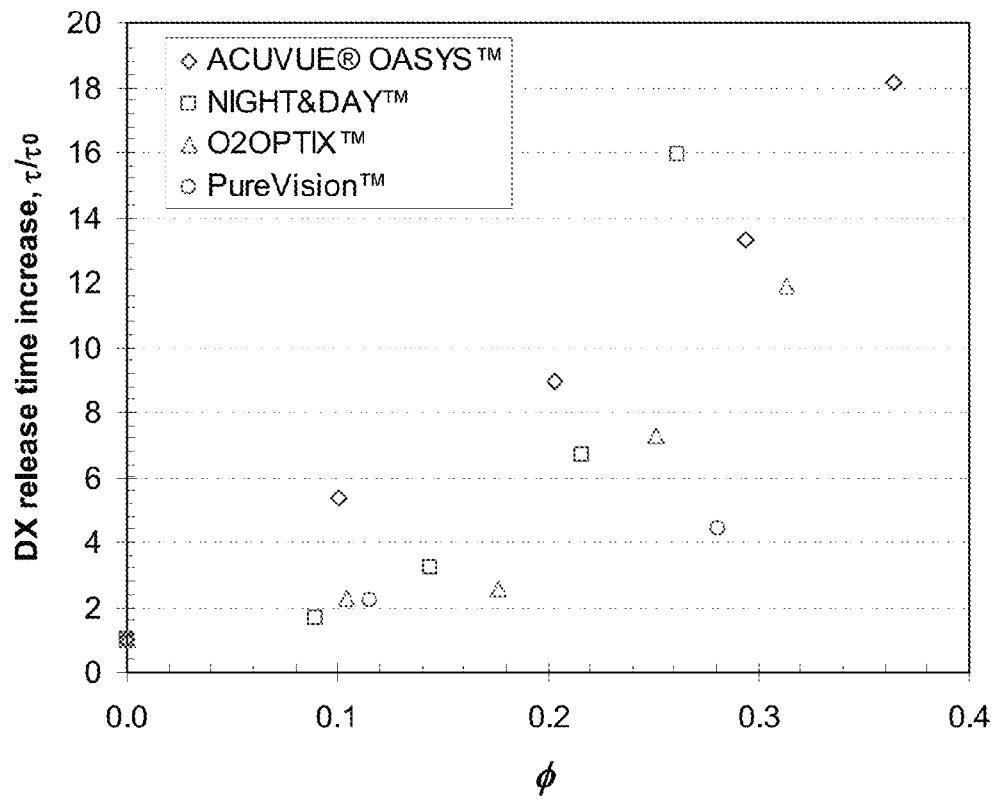

Effect of Vitamin Loading on Drug (Dexamethasone) Release from Silicone-Hydrogel Lenses FIGS. 18 through 20 show dexamethasone release from various contact lenses and the effect of the vitamin loading on the DX release. For lenses whose release is shown in FIGS. 18 through 20, the Vitamin E was loaded by soaking the contact lens in Vitamin E-ethanol solution. Subsequently the lens was dried and dexamethasone was loaded by soaking Vitamin E loaded lens in dexamethasone-PBS solution (0.08 mg/ml) for 7 days. Vitamin E loadings are indicated in the legend of FIGS. 18 through 20. The dexamethasone release occurred over a longer period from Vitamin E containing lenses than from nutraceutical free lenses. The dexamethasone released over any given time period was higher for the nutraceutical free lenses than it was for the lenses containing Vitamin E. This contrasts with the timolol release indicated above, and this difference appears to occur because timolol is a hydrophilic drug but dexamethasone is a hydrophobic drug.

Example 17

Dynamics of Drug by Vitamin E Loaded Lenses

Dynamics of DX uptake and release of Vitamin E loaded lenses with different Vitamin E loadings are shown in FIG. 21. For PureVision™ lens loaded with Vitamin E, only three different Vitamin E loadings were examined since the effect of Vitamin E loading on drug transport is minimal compared to other lenses. The insets in FIG. 21 show plots for drug release for the initial hours. Vitamin E was loaded in the lens, the lens were dried and DX was loaded in the Vitamin E loaded lens by soaking the lens in the DX-PBS solutions. The uptake and release experiments was not examined for ACUVUE® ADVANCE™ lens, which became too weak to easily handle after swelled in Vitamin E solution and as ACUVUE® ADVANCE™ lens showed the most rapid release for both drugs (DX and timolol) as indicated above. As seen in FIG. 21, all lenses exhibit an increase in loading or release time as the Vitamin E loading increases. DX loading time is relatively long for ACUVUE® OASYS™ lenses and relatively short for PureVision™ lenses relative to that of NIGHT&DAY™ and O₂OPTIX lenses for similar Vitamin E loadings regardless of the level of Vitamin E loading.

For loading, an experimentally determined partition coefficient of drug in the Vitamin E loaded lens (K) is defined as:

$$K = \frac{C_{l,f}}{C_{w,f}} = \frac{V_w(C_{w,i} - C_{w,f})}{V_l C_{w,f}} \tag{4}$$

where $V_w$ and $V_l$ are the volumes of the drug-PBS solution and the dry lens (either with or without vitamin loaded), respectively, and $C_{l,f}$, $C_{w,i}$ and $C_{w,f}$ are the equilibrium (final) concentrations of the drug in the lens phase, and the initial and equilibrium (final) concentrations in the aqueous phase, respectively, in the loading experiment. $V_w$ for loading experiments was 2 mL, as the lens was dry before placement of the lens in the drug-PBS solutions. Partition coefficient of drug in the Vitamin E free (pure) lens ($K_{pl}$) can be written as:

$$K_{pl} = \frac{C_{pl,f}}{C_{w,f}} = \frac{V_w(C_{w,i} - C_{w,f})}{V_{pl} C_{w,f}} \tag{5}$$

where $V_{pl}$ and $C_{pl,f}$ are the volume of the dry pure lens and the equilibrium concentration of the drug in the pure lens phase, respectively. The mass balance of drug in the vial yields:

$$M_i = C_{pl,f}V_{pl} + C_{ve,f}V_{ve} + C_{w,f}V_w = K_{pl}C_{w,f}V_{pl} + K_{ve}C_{w,f}V_{ve} + C_{w,f}V_w \tag{6}$$

where $M_i$ is total mass of drug in the vial and $C_{ve,f}$ is the equilibrium concentration of the drug in the vitamin E aggregates. $V_{ve}$ is the volume of Vitamin E aggregates in the lens and is calculated by $V_l(\phi - \phi^*)$. In this model, $\phi$ is the volume ratio of Vitamin E in the dry lens, and $(\phi - \phi^*)$ is the fraction that is present in a separated Vitamin E phase, where a fraction $\phi^*$ either exists within the polymer hydrogel or separated in one or more regions of the lens that do not contribute to drug transport. Partition coefficient of drug in Vitamin E phase ($K_{ve}$) can be obtained as $$K_{ve} = \frac{C_{ve,f}}{C_{w,f}} = \frac{M_i/C_{w,f} - K_{pl}V_{pl} - V_w}{V_l(\phi - \phi^*)} \tag{7}$$

For release experiments, the lenses soaked in drug-PBS solution were directly transferred from the loading solution to the fresh PBS, and thus these were fully hydrated at the beginning of the release experiment. Consequently, $V_w$ is the sum of fresh PBS volume and the loading solution existing in the lens at equilibrium.

The total loading or release time increase for DX by Vitamin E loaded lenses is shown in FIG. 22. The total loading (or release) time ($\tau$) is the duration in loading (or release) for loading (or release) of 90% of total drug. The total loading (or release) time increase defined as ($\tau$) divided by the total loading (or release) time for Vitamin E free (pure) lens ($\tau_0$) plotted versus Vitamin E loading, where Vitamin E loading is percentage of Vitamin E to pure lens in dry weight, is presented in FIG. 22. For dexamethasone loading, time increases for NIGHT&DAY™ and O₂OPTIX are similar with about a 2-fold loading time increase at about 10% Vitamin E loading and about a 10-fold increase for about 30% Vitamin E loading. The effect of about 10% Vitamin E loading for PureVision™ lens on loading duration is negligible and even about 40% Vitamin E loading shows only 6-fold increase. The drug release time increase is qualitatively similar to the drug uptake time increase for DX although the increases in release duration are slightly less than the increases in the loading duration. For example, NIGHT&DAY™ lenses with 27% Vitamin E release shows 6.5-fold increase in release duration compared to a 9-fold increase in loading duration with the same Vitamin E loading. As shown in FIG. 22, the total amount of DX loaded and released are about same for each lens for the various Vitamin E loading within the error margins with the exception of ACUVUE® OASYS™ lenses, suggesting its partition coefficient remains about constant before and after Vitamin E loading. As the values of K for the various lenses, listed in Table 6, below, tend to be independent of Vitamin E loading for each lens except for ACUVUE® OASYS™ lens, the decrease in the loading and release of DX does not appear to be due to a difference in diffusivity, D. Vitamin E was not detected in the release medium, PBS, presumably due to a very low solubility of Vitamin E in PBS.

Figure 23A:
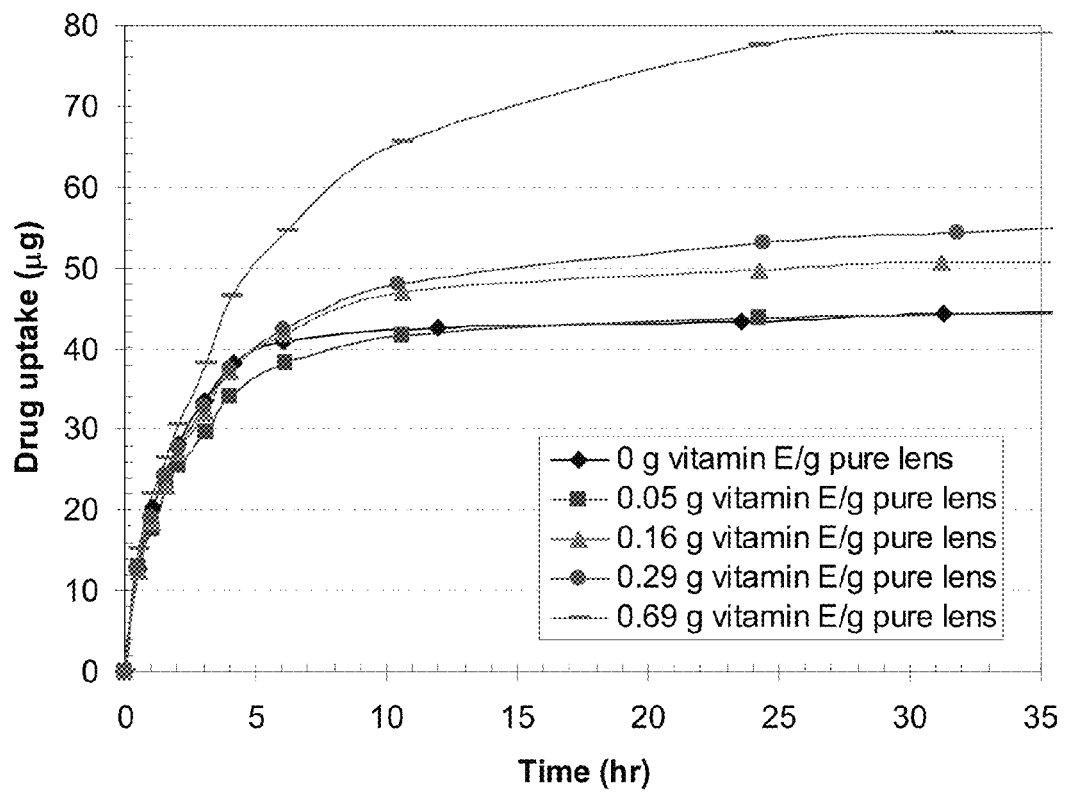
FIGS. 23A-23B shows plots of A) KF uptake by and B) KF release from Vitamin E loaded NIGHT&DAY™ lenses where Vitamin E was loaded by soaking the lenses in Vitamin E-ethanol solution, dried, and KF was loaded by soaking the Vitamin E loaded lenses in KF-PBS solution (0.084 mg/ml).
Figure 23B:
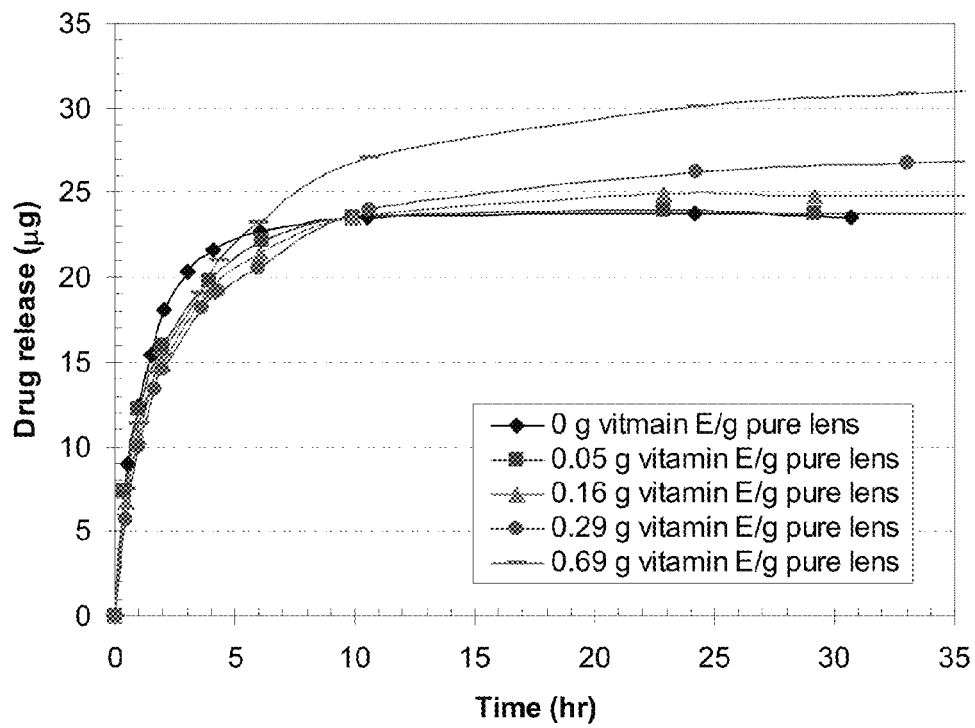
Figure 24A:
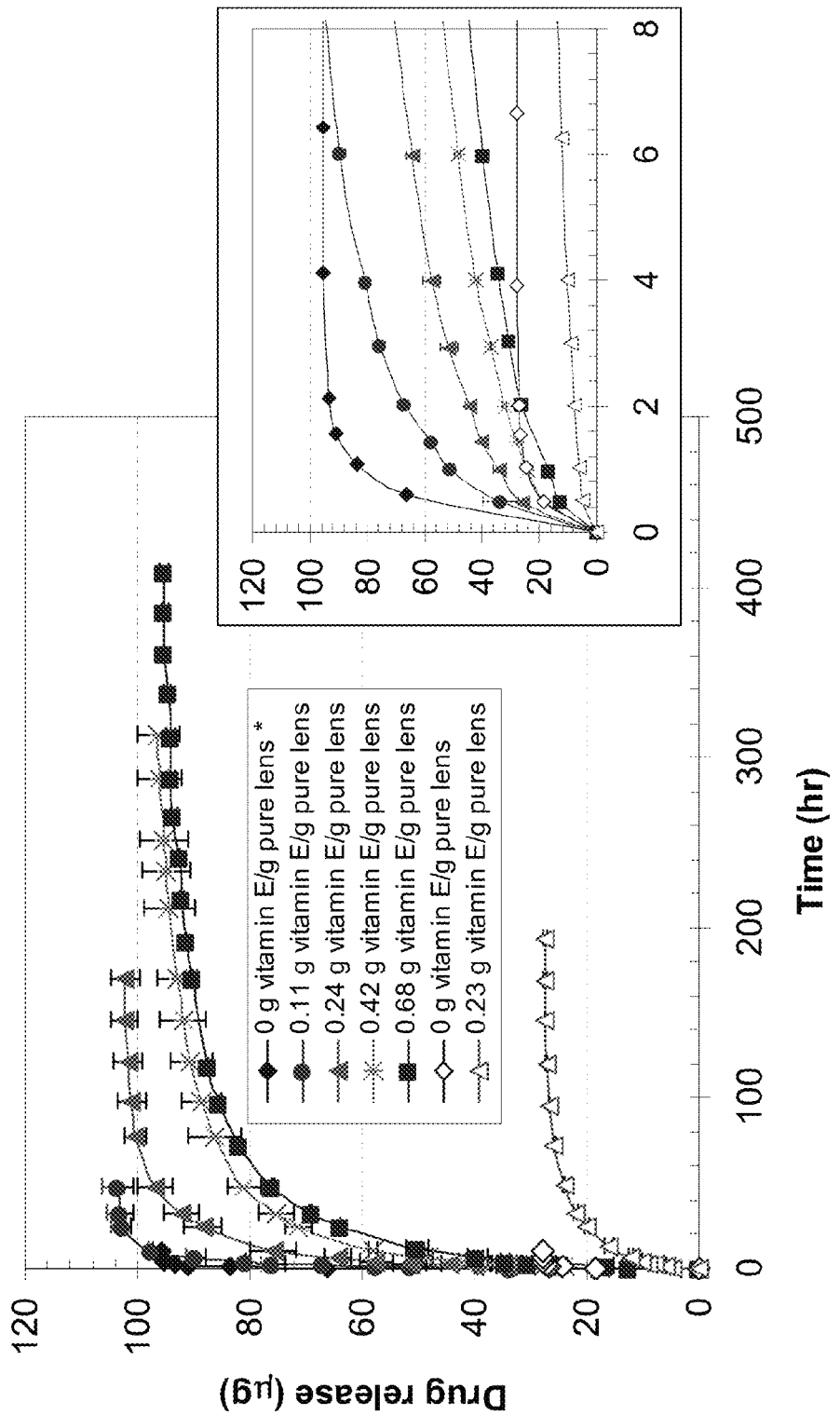
FIGS. 24A-24D shows profiles of timolol release by Vitamin E loaded A) ACUVUE® OASYS™, B) NIGHT&DAY™, C) $O_2$OPTIX™, and D) PureVision™ contact lenses versus time for lenses loaded by soaking in timolol/Vitamin E-ethanol solution (0.8 mg timolol in 3 ml of Vitamin E-ethanol solution of various concentrations) for 24 hours shown as solid marks, or in timolol-PBS solution (0.8 mg/ml) for 7 days shown as hollow marks with Vitamin E loadings indicated in the legends where inserts plot the initial release over 8 hours.
Figure 24B:
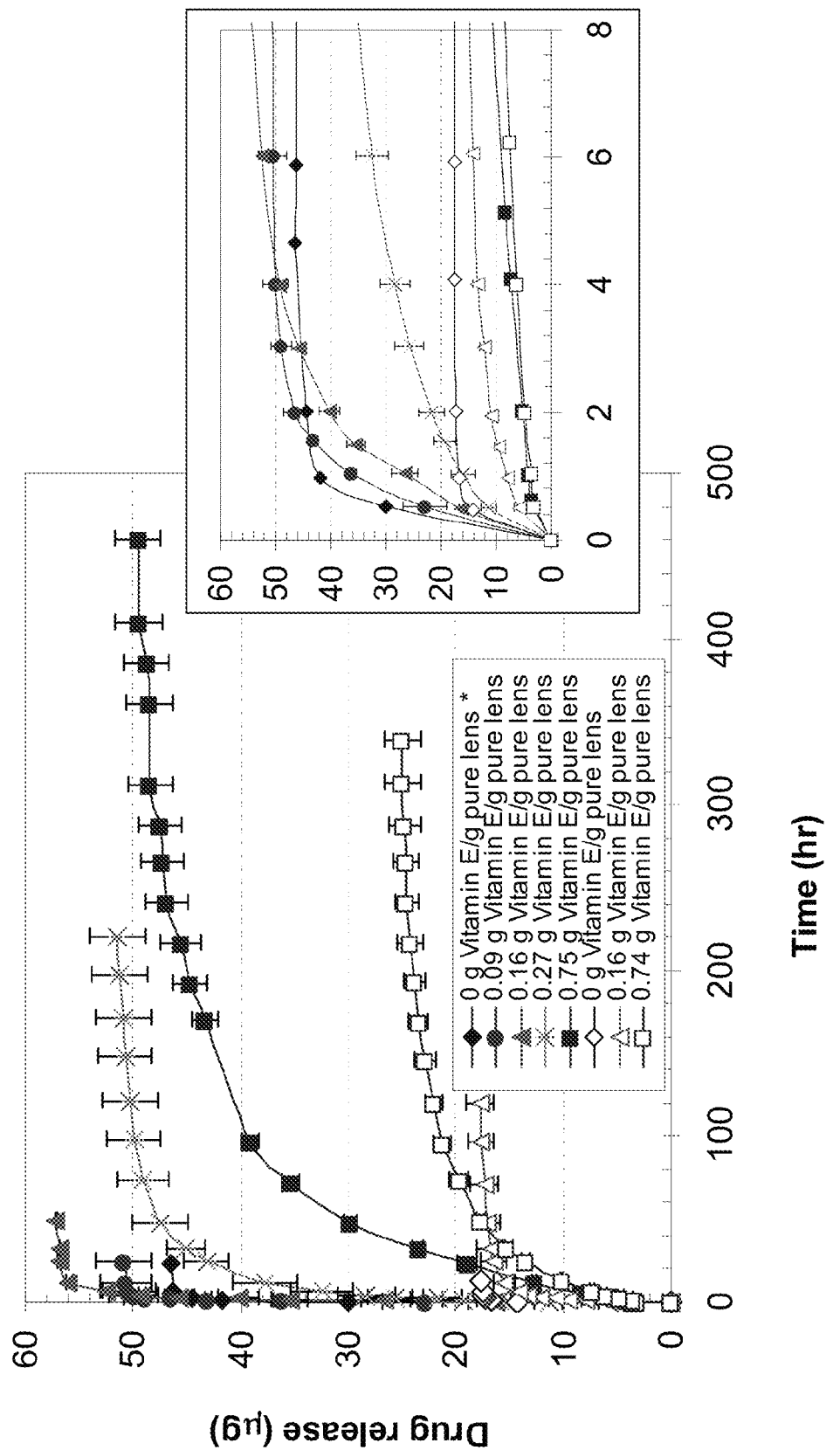
Figure 24C:
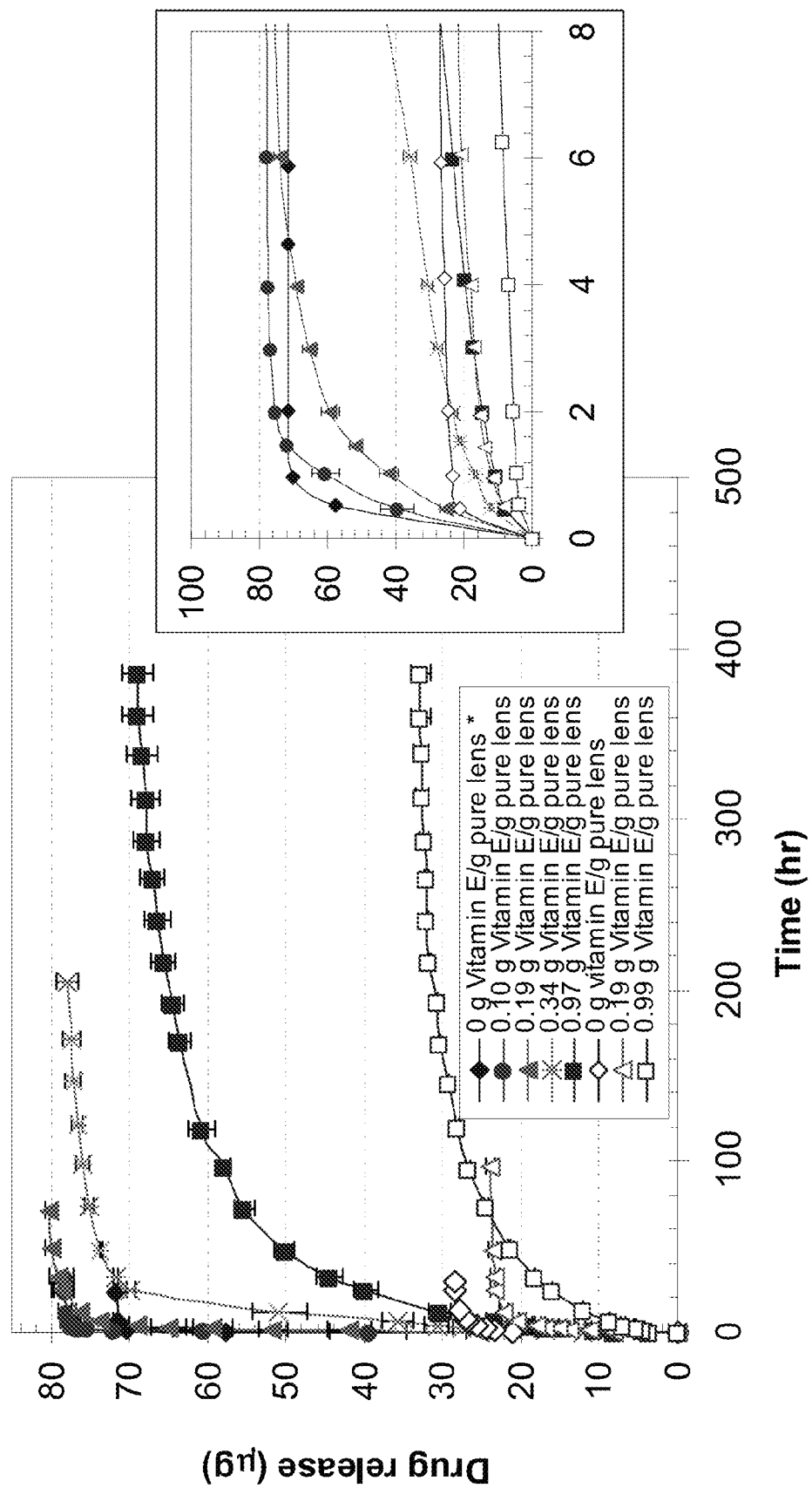
Figure 24D:
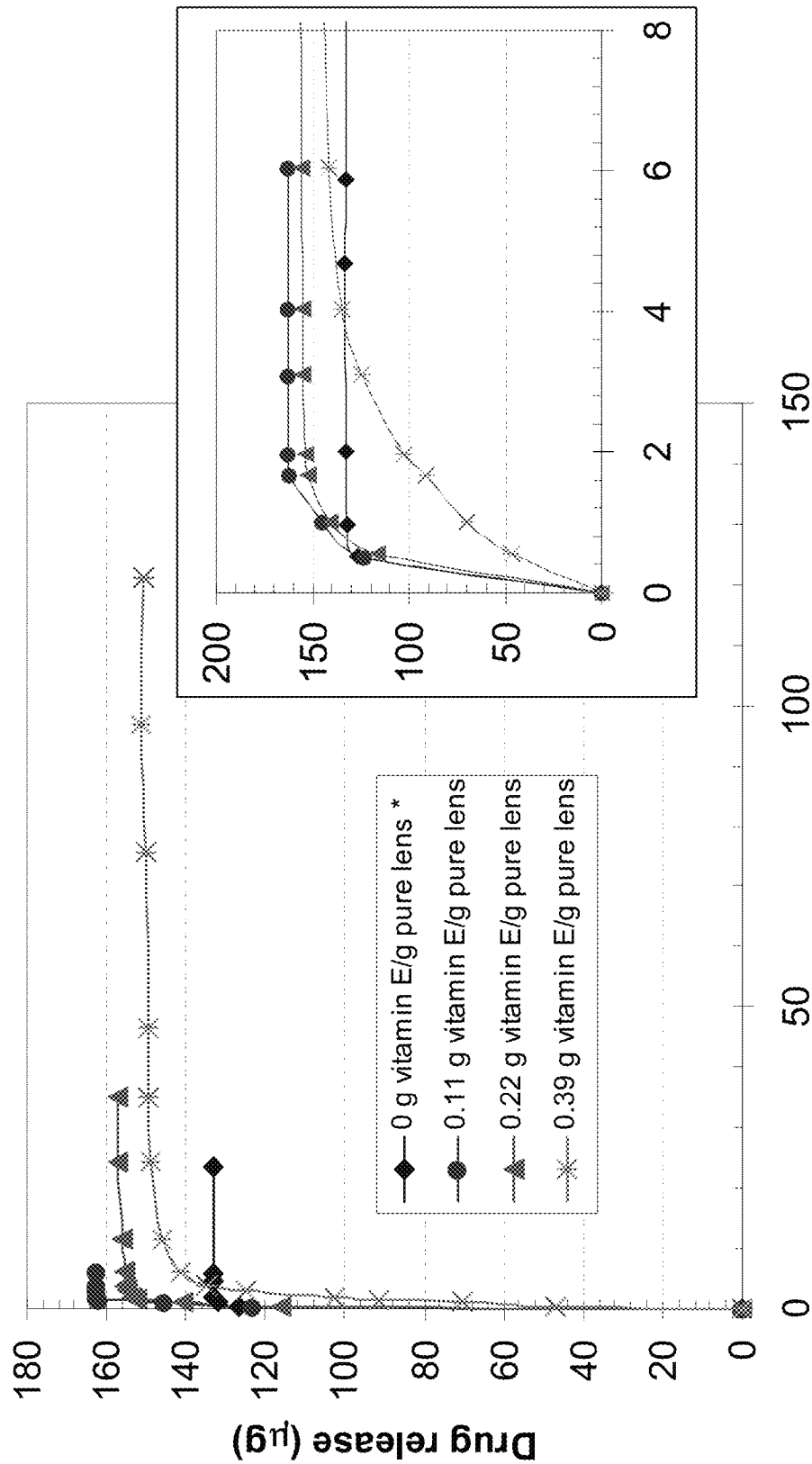

KF uptake and release experiments were conducted with NIGHT&DAY lenses of five different Vitamin E loadings and results are shown in FIG. 23. KF uptake time by a pure lens was about 4 hours and there was no dramatic difference in the uptake time for different vitamin loadings. For example, with the highest Vitamin E loading, 69%, uptake time was only 3 times that of a Vitamin E free (pure) lens. The effect of loading on the release time was also small. Nevertheless, the amount of KF uptake and release clearly depends on the Vitamin E loading and the time increases as Vitamin E loading increases, suggesting that much KF is dissolved in a Vitamin E phase included in the lens. The partition coefficients of KF in the lens (K) and vitamin E ($K_{ve}$) were computed and listed in Table 7, below.

TABLE 6

Partition coefficient (K) of DX in lenses soaked in DX-PBS solution.

| Contact lenses | Vitamin E loading [g Vitamin E/ g pure lens] | K for loading | K for release |
|---|---|---|---|
| ACUVUE® ADVANCE ™ | 0.00 | 64.6 | 57.3 |
| ACUVUE® OASYS ™ | 0.00 | 77.4 | 105.7 |
|  | 0.11 | 89.7 | 116.9 |
|  | 0.24 | 76.7 | 96.2 |
|  | 0.42 | 94.9 | 149.6 |
|  | 0.70 | 80.2 | 120.4 |
| NIGHT&DAY ™ | 0.00 | 119.2 | 137.7 |
|  | 0.10 | 120.3 | 137.8 |
|  | 0.17 | 111.7 | 126.5 |
|  | 0.28 | 106.7 | 137.7 |
|  | 0.35 | 110.4 | 162.8 |
| O₂OPTIX ™ | 0.00 | 131.3 | 146.3 |
|  | 0.12 | 131.0 | 143.9 |

TABLE 6-continued

Partition coefficient (K) of DX in lenses soaked in DX-PBS solution.

| Contact lenses | Vitamin E loading [g Vitamin E/ g pure lens] | K for loading | K for release |
|---|---|---|---|
|  | 0.21 | 120.7 | 134.5 |
|  | 0.34 | 119.4 | 141.8 |
|  | 0.46 | 115.9 | 149.1 |
| PureVision ™ | 0.00 | 290.7 | 326.5 |
|  | 0.13 | 159.6 | 241.7 |
|  | 0.39 | 181.3 | 203.8 |

TABLE 7

Partition coefficient of KF in vitamin loaded NIGHT&DAY® lenses (K) and in Vitamin E ($K_{ve}$).

| Vitamin E loading [g Vitamin E/ g pure lens] | K for loading | $K_{ve}$ for loading | K for release | $K_{ve}$ for release |
|---|---|---|---|---|
| 0.00 | 32.7 | — | 80.7 | — |
| 0.05 | 32.4 | — | 79.1 | — |
| 0.16 | 34.3 | 72.3 | 83.1 | 159.0 |
| 0.29 | 34.1 | 51.0 | 74.3 | 67.2 |
| 0.69 | 48.6 | 82.2 | 86.1 | 107.7 |

FIG. 24 shows timolol release from timolol-Vitamin E loaded lenses for different loadings of Vitamin E. Vitamin E loadings are indicated in FIG. 24 where insets show plots for drug release for the initial 8 hours. Timolol and Vitamin E were loaded into lenses simultaneously by soaking the lens in 0.8 mg/ml of timolol/Vitamin E-ethanol solution for 24 hours. For Vitamin E free (pure) lenses, timolol was loaded by soaking in a timolol/ethanol solution of 0.8 mg/ml for 3 hours. As clearly indicated in FIG. 24, the rate of timolol release by all lenses decreased as the Vitamin E loading increased with the exception of PureVision™ where the release rate decreased with increasing Vitamin loading, although the total amount of drug released did not change significantly. For comparable Vitamin E loadings, ACUVUE® OASYS™ and NIGHT&DAY™ had the longest duration of timolol release and PureVision™ had the shortest. For example, ACUVUE® OASYS™ lens with a 11% Vitamin E loading released about 100 μg of timolol over a period of 9 hours where a period of 31.5 hours was observed for a 24% Vitamin E loaded lens. A PureVision™ lens released a slightly higher amount of timolol (about 150 μg) over about 1 hour for all the Vitamin E loadings. The effect of Vitamin E loading in the release duration compared to the equivalent Vitamin E free (pure) lens was observed to be greatest for NIGHT&DAY™ and least for PureVision™ lenses over the examined range of Vitamin E loadings as seen in FIG. 25. Specifically, NIGHT&DAY™ shows a 9.8-fold increased release duration for a 16% Vitamin E loading (about 5.5 hours), a 76-fold duration increase for a 27% Vitamin E loading (43 hours), and a 341-fold duration increase for a 74% Vitamin E loading (192 hours). The total amount of timolol released by NIGHT&DAY™ was the lowest, about 50 μg. O₂OPTIX™ with a 20% Vitamin E loading releases about 80 μg of timolol over about 4.9 hours and a 34% Vitamin E loaded lenses required about 24 hours. The 20-30% Vitamin E loaded lenses: ACUVUE® OASYS™, NIGHT&DAY™, and O₂OPTIX™ can deliver timolol for about one day. The drug transport data for PureVision™ lenses suggests that the Vitamin E simply dissolves in the matrix leading to negligible barrier effect. However the drug transport data for ACUVUE® OASYS™ lenses shows a significant barrier effect, which in combination with the EW data suggests that the barrier effect in these lenses likely arises due to Vitamin E that coats polymer fibers rather than forming larger aggregates, which appears to be the mechanism for NIGHT&DAY™ and O₂OPTIX™ lenses.

In other experiments, timolol was loaded separately from Vitamin E into lenses by an alternate protocol where Vitamin E was loaded into lenses by soaking the lenses in Vitamin E-ethanol for 24 hours and drying the lenses. Subsequently, timolol was loaded into the Vitamin E loaded lens by soaking in timolol-PBS for 7 days. Timolol release profiles of the NIGHT&DAY™, ACUVUE® OASYS™ and O₂OPTIX™ lenses for sequential loading of Vitamin E and timolol are also shown in FIG. 24. As can be seen in FIG. 24, this method results in lenses with increased timolol release duration and with high Vitamin E loadings (70% for ACUVUE® OASYS™, 74% for NIGHT&DAY™, and 97% for O₂OPTIX™) an increased amount of timolol released from Vitamin E loaded lenses when compared to release from Vitamin E free (pure) lenses. Therefore, loading timolol and Vitamin E at the same time through ethanol medium is a more efficient way to preparation timolol-Vitamin E loaded lenses. For O₂OPTIX™, with an equivalent amount of Vitamin E loading, the release profiles from the lenses that had timolol and Vitamin E loaded sequentially are almost the same as those where timolol and Vitamin E were loaded simultaneously. However, even though the release durations for ACUVUE® OASYS™ and NIGHT&DAY™ loaded by different methods are similar, the release profiles are slightly different. The difference is likely due to the non-homogeneous distribution of timolol inside the lens. Timolol loaded by drug-PBS solution partitions into the gel matrix by diffusion over a long period of time, leading to a relatively homogeneous distribution in the lens. On the other hand, timolol uptake in drug-ethanol solution may display a high drug concentration in the center region of the lens after ethanol evaporation.

The increased duration for timolol loading or release from Vitamin E containing lenses is greater than that for DX or KF at comparable Vitamin E loadings. For example, NIGHT&DAY™ with 27% Vitamin E loading has a 76 times greater timolol release duration though only a 6 fold increased duration for DX loaded lenses in spite of the greater release duration for DX (107 hours) than timolol (43 hours). O₂OPTIX™ with 34% vitamin loading also showed a larger release duration increase over that of a Vitamin E free lens of 15.5 times for timolol as opposed to the 5 fold release duration increase for DX. This is an unexpected result as DX is more hydrophobic than timolol at pH 7.4 in PBS medium where timolol exists primarily in a charged form and a partition coefficient increase for DX in a Vitamin E loaded lens would be expected to be large relative to that of timolol leading to a larger increase in release duration for DX. The reduction in release rates is consistent with the formation of phase separation of Vitamin E in the lens material where the formed Vitamin E phases act as diffusion barriers. Alternately, the Vitamin E phase need not be macroscopic aggregates but could be present as an adsorbed phase on the polymer where the effective diffusivity of the drug is the average of the surface and the bulk diffusivities weighted by the fraction of the Vitamin E bound and the free drug, respectively, where the Vitamin E phase adsorbed on the polymer surfaces hinders surface diffusion of the drug.

To examine the stability of Vitamin E loading in the lenses and potential morphology change over time, a second drug loading and release was conducted with some lenses. NIGHT&DAY™ lenses with various Vitamin E loadings were kept in PBS solution after a first release experiment for at least 6 month, soaked in 250 ml of DI water with moderate stirring for 48 hours to remove residual timolol. These cleaned Vitamin E lenses were dried as described above for Vitamin E included lenses and the dry weight was measured to ensure that the Vitamin E loading remained the same as the initial loading. The dry weight of the lens was within 1% difference of that measured immediately after the initial Vitamin E loading, which indicates that Vitamin E does not diffuse into PBS during the storage. The lenses were reloaded with timolol by soaking the lens in a 0.8 mg/ml timolol-PBS solution for 7 days. After the drug loading, the drug release profiles were measured in 2 ml PBS, as shown in FIG. 26. The release profiles were almost identical to the initial release profiles. For example, NIGHT&DAY™ lenses with 16% Vitamin E loading released 22 μg timolol in 10.5 hours in the second release experiment, which is nearly identical to the result from the first release experiment that was conducted 6 months previously (21 μg), regardless of the drug loading method (drug-PBS or drug-ethanol medium) employed. This indicates that the morphology of the Vitamin E laden lenses is stable even after soaking in PBS for 6 months, and thus the drug release behavior of these lenses will not degrade during packaging and shelf storage. The morphology of the Vitamin E laden lenses does not change during PBS soaking, likely because of the negligible solubility of Vitamin E in PBS.

DXP release profiles for various Vitamin E loaded NIGHT&DAY™, O₂OPTIX™, ACUVUE® OASYS™ and PureVision™ lenses having various Vitamin E loadings can be seen in FIG. 27. DXP was loaded separately from Vitamin E into these lenses. Vitamin E was loaded into lenses by soaking in Vitamin E-ethanol solution for 24 hours followed by drying in the manner described above. The dried Vitamin E loaded lenses were soaked in 0.7 mg/ml DXP-PBS solutions for a sufficient time to establish equilibrium partitioning of the DXP between the solution and lens. Uptake dynamics were not measured directly as the DXP provided an absorbance beyond the range that the UV-VIS spectrometer could measure at the concentrations employed using the experimental methods employed for other drugs as described above. The equilibrium uptake was confirmed by comparing the drug release profile, the time to reach equilibrium. In all experiments using DXP-Vitamin E loaded lenses, the uptake periods were longer than the release equilibrium time, suggesting that equilibrium was achieved during loading. FIG. 27 shows that, similar to the release profiles observed for timolol, the DXP release rate decreases as Vitamin E content increases while the total DXP release amount was relatively independent of the Vitamin E loading. For similar Vitamin E loading, ACUVUE® OASYS™ displays a longer drug release time, followed by NIGHT&DAY™ and O₂OPTIX™ lenses, which are longer than the release from PureVision™ lenses. For example, ACUVUE® OASYS™ lenses with a 10% Vitamin E loading and 23% Vitamin E loading releases about 27 μg of DXP in 7 days and 3 weeks respectively, while 40 μg of DXP is released in 8 hours from a 36% Vitamin E loaded PureVision™ lens. While there are no significant difference in drug release time for DX and DXP from Vitamin E free (pure) lenses (10 hours and 7.5 hours by NIGHT&DAY™, 10.5 hours and 14 hours by ACUVUE® OASYS™, respectively), Vitamin E loading has a stronger retardation of the drug release rate for DXP than for DX. With a loading of about 24% Vitamin E, NIGHT&DAY™ lenses showed 40-fold increased release duration of about 12 days as opposed to the 6.7-fold increase of release duration of about 4.5 days for DX. Although not to be bound by a mechanism, these results suggest that Vitamin E separate phases in the lenses serve as diffusion barriers for hydrophilic ionic DXP that should not diffuse through a hydrophobic Vitamin E phase as opposed to the hydrophobic DX which should have the ability to diffuse through Vitamin E. Although the drug release duration is much longer, the increase of the ratio of the release duration time relative to a Vitamin E free lens for various Vitamin E loadings for DXP is similar to that observed for timolol, as shown in FIG. 28. It This suggests that the attenuation in drug release rates is similar for all hydrophilic drugs, even though the diffusivities of the drugs in the pure lenses may be vastly different, which will be further discussed later.

Another hydrophilic ophthalmic drug, fluconazole, was employed to examine the effect of Vitamin E loading in release from contact lens. FIG. 29 shows the fluconazole release dynamics for Vitamin E loaded NIGHT&DAY™, ACUVUE® OASYS™ and O₂OPTIX™ lenses. Employing the same method used with DXP, fluconazole was loaded in the lenses after loading of Vitamin E. Vitamin E was loaded by soaking the lens in Vitamin E-ethanol solution for 24 hour. The lens was dried and soaked in a 0.7 mg/ml fluconazole-PBS solution for a sufficient time to achieve equilibrium content of the drug in the lenses. Vitamin E loading extended the fluconazole release duration relative to Vitamin E free (pure) lens without significantly greater drug uptake as can be seen in the final release profiles. For example, 17%, 26%, 39% and 66% Vitamin E loaded NIGHT&DAY™ lenses released about 60 µg of fluconazole over a period of 10 hours, 24 hours, 88 hours and 227 hour respectively, which are 6.2, 14, 55 and 142-fold release duration increases, respectively. The total amount of fluconazole released by the different lenses was similar, although O₂OPTIX™ displayed a slightly higher drug release of about 80 µg. With similar Vitamin E loadings, ACUVUE® OASYS™ shows a longer fluconazole release period then NIGHT&DAY™ and O₂OPTIX™. For example, with 21% Vitamin E loading, ACUVUE® OASYS™ released about 70 µg of fluconazole in 91 hours, a 20-fold release duration increase over a Vitamin E free lens, as opposed to 8.6 hours (7.3 fold) for O₂OPTIX™ lenses and 9.9 hours for NIGHT&DAY™ lenses. Similarly to timolol, lenses with 20~30% of Vitamin E loading, are able to deliver fluconazole for about one day.

FIG. 30 shows results of CyA release by Vitamin E loaded ACUVUE® OASYS™ lenses in 1.75 ml PBS medium at perfect sink condition. As shown in FIG. 30A, the drug release rate decreases as the Vitamin E loading amount in the contact lenses increases, even though the total drug uptake amount increases. For example, during the first 7 days, ACUVUE® OASYS™ with loadings of 0%, 10% and 20% of Vitamin E released CyA into PBS at an average rate of 8.7, 8.0 and 5.5 µg/day, respectively. Due to the high bioavailability of contact lens, these Vitamin E loaded lens should provide sufficient amount of CyA compared to current therapeutic treatment of Restasis® eye drops. It is also noted that the drug release duration by these contact lenses are significantly extended with higher Vitamin E loading as shown in FIG. 30B. For example, for pure ACUVUE® OASYS™ lens, 60% of the inclusive CyA in the lens was released in 7 days, while it took 16 and 46 days for ACUVUE® OASYS™ with 10% and 20% Vitamin E loading to release the same percentage of drugs, respectively. In addition, with 10% of Vitamin E loading, the loaded CyA in the contact lens can be released for more than 45 days, which is sufficient for the desired aim of continuous one-month drug delivery by silicone contact lens. These results demonstrated that a tailored CyA release profile by silicone hydrogel contact lenses, such as ACUVUE® OASYS™, can be achieved by manipulating the drug concentration in soaking solutions and the Vitamin E loading amount in the lens.

The effect of Vitamin E loading on hydrophilic drug transport is summarized in FIG. 28. As clearly shown for NIGHT&DAY™, ACUVUE® OASYS™ and O₂OPTIX™ lenses having the same volume fraction of Vitamin E in the lens, the release duration for DX is much less than for DXP, timolol and fluconzole, while in PureVision™ there is no significant effect of Vitamin E loading on the drug release time. The three hydrophilic drugs release by Vitamin E loaded ACUVUE® OASYS™ and O₂OPTIX™ lens with equivalent amounts of Vitamin E loading showed similar time duration ratio as Vitamin E free lenses, while fluconazole released by NIGHT&DAY™ lens exhibits a smaller duration increase than timolol and DXP at similar vitamin loadings. In addition, for the three hydrophilic drugs, the drug release duration ratio is not linear, but fits a quadratic function of the volume fraction of Vitamin E in the lenses. In general, the results show a significant effect of Vitamin E loading in contact lens for extending the drug release duration, especially for hydrophilic drugs, in most commercial silicone contact lenses and this effect is influenced by the specific composition of lens structure.

Hydrophilic drugs have a negligible partitioning into Vitamin E. The increase in release duration for charged drugs is likely due to the presence of Vitamin E aggregates formed within the hydrogel that act as diffusion barriers that increase the length of the path that a charged drug molecule takes to diffuse from within the hydrogel to the external fluid reservoir, as indicated in the schematic drug path through a lens shown in FIG. 1. The path length of the tortuous path l should scale as $h(1+\alpha(\phi-\phi^*))$, where h is the half thickness of lens, and $\alpha$ depends on the microstructure, including particle size and aspect ratio, of the Vitamin E aggregates distribution in the gel; $\phi$ is the volume ratio of Vitamin E in the dry gel, and $(\phi-\phi^*)$ is the fraction that is present as the Vitamin E particles. The fraction $\phi^*$ is the fraction of Vitamin E that exists within the material of the lens or as separated phases in regions of the lens that do not contribute to drug transport. For a diffusion-controlled release, the time for release scales as $$\frac{l^2}{D}.$$

The lens thickness increases due to Vitamin E uptake, and assuming isotropic expansion and small Vitamin E loadings, the resulting half thickness is $h=h_0(1+\phi/3)$, where $h_0$ is a half thickness of pure lens. The time of release thus scales as:

$$\tau \sim \frac{h_0^2}{D}\left(1+\frac{\phi}{3}\right)^2 (1+\alpha(\phi-\phi^*))^2 \qquad (8)$$

The term $$\left(1+\frac{\phi}{3}\right)^2$$

does not make a significant contribution to the increase in release duration for $\phi$ values less than about 1, where this term is less than 2. Neglecting this term the duration relative to a Vitamin E free lens is:

$$\frac{\tau}{\tau_0} \sim ((1-\alpha\phi^*)^2 + 2\phi(\alpha-\alpha^2\phi^*) + \alpha^2\phi^2) \quad (9)$$

where $\phi > \phi^*$ and time r is the duration for 90% release and $\tau_0$ is the corresponding duration for the lens without Vitamin E. The parameters $\alpha$ and $\phi^*$ can be obtained by fitting the data shown in FIG. 28 to the above model. The error between the experimental data and model prediction is defined $\sqrt{\Sigma\{(\tau/\tau_0)-(\tau/\tau_0)_{ex}\}^2/\Sigma(\tau/\tau_0)_{ex}}$ where $(\tau/\tau_0)$ and $(\tau/\tau_0)_{ex}$ are the predicted release time ratio by model and the experimental release duration ratio relative to Vitamin E free (pure) lenses, respectively. The parameters $\alpha$ and $\phi^*$ for timolol, fluconazole and DXP were obtained using the function 'fminsearch' in MATLAB® with minimization of the error and are given in Table 8, below. For a given lens, the same value of $\phi^*$. was imposed in all fits since this parameter should be the same for all the drugs as it only depends on the interaction of Vitamin E with the lens matrix. Also the values of $\alpha$ should be similar for all drugs since this is a geometric parameter that only depends on the microstructure of the Vitamin E laden lenses. The good fits between the model and the data with identical $\phi^*$. and similar $\alpha$ for each drug further substantiate the mechanisms and the model presented above.

TABLE 8

Parameters of scaling theory for timolol

| Contact lens | Timolol $\phi^*$ | Timolol $\alpha$ | Fluconazole $\phi^*$ | Fluconazole $\alpha$ | DXP $\phi^*$ | DXP $\alpha$ |
|---|---|---|---|---|---|---|
| ACUVUE® OASYS ™ | 0.016 | 24.4 | 0.033 | 23.8 | 0.002 | 27.48 |
| NIGHT&DAY ™ | 0.053 | 46.47 | 0.092 | 35.98 | −0.003 | 27.41 |
| O₂OPTIX ™ | 0.093 | 33.25 | 0.097 | 34.02 | 0.076 | 38.33 |
| PureVision ™ | 0.119 | 1.06 | | | 0.131 | 10.955 |

The above model is not probable for hydrophobic drugs as they can partition into Vitamin E phase where drug transport can occur by diffusion around the Vitamin E aggregates and by dissolution and diffusion through these aggregates. Accordingly, the increase in release time is much greater for hydrophilic drugs such as timolol compared to hydrophobic drugs such as dexamethasone or KF, which can partition into the Vitamin E aggregate phases, diffuse through these phases and into the lens matrix. Thus the transport of hydrophobic drugs through the Vitamin E-laden silicon hydrogel lens can be considered as diffusion through regions of the hydrogel matrix and regions of Vitamin E arranged in series. For series arrangement of the hydrogel (G) and the Vitamin E (V) phases, the effective diffusivity can be shown to be:

$$D_{eff} = \frac{1}{\sum K_i \phi_i} \left(\sum \frac{\phi_i}{D_i K_i}\right)^{-1} \quad (10)$$

where $D_i$, $K_i$, $\phi_i$ are the diffusivity, partition coefficients (with respect to PBS), and volume fractions of the ith phase, with i=G and V for the gydrogel and the Vitamin E phase, respectively. Thus, the ratio of duration of release for a Vitamin E containing lens to a Vitamin E free (pure) lens is given by the expression:

$$\frac{\tau}{\tau_0} = \sum K_i \phi_i \left(\sum \frac{\phi_i}{D_i K_i}\right) = (K_G \phi_G + K_V \phi_V)\left(\frac{\phi_G}{K_G} + \frac{D_G \phi_V}{D_V K_V}\right) \quad (11)$$

Contact lenses have a specific geometry, such as its curvature and variable thicknesses from center to edge, depending on the power of the lens. However, the diameter of a lens (about 14 mm) is much larger than its thickness (about 80 to 100 μm) and so we can simplify the geometry of lens for the model as a thin flat film with different thickness on the axis perpendicular to direction of overall diffusion. In this form, the mass transfer for transport in the contact lens can be described by the equations:

$$\frac{\partial C}{\partial t} = D\frac{\partial^2 C}{\partial y^2} \quad (12)$$

where C is the drug concentration in the hydrogel, D is the effective diffusivity and y and t denote the transverse coordinate and time, respectively. The boundary conditions for the drug release experiment are:

$$\frac{\partial C}{\partial y}(t, y=0) = 0 \quad (13)$$

$$C(t, y=h(x)) = KC_w$$

where h is the half-thickness of the lens, which depends on the curved lateral coordinate x, and $C_w$ is the drug concentration in the release medium. The first boundary condition requires symmetry at the center of the lens and the second boundary condition requires equilibrium between the drug concentration in the lens and that in the PBS phase. A mass balance on the PBS in the beaker yields $$V_w \frac{dC_w}{dt} = -2D \int_0^S P(x) \frac{\partial C}{\partial y}\bigg|_{y=h} dx \quad (14)$$

where $V_w$ is the PBS volume, $P(x)$ is the perimeter of the lens at the coordinate x, and S is half of the maximum arc length. Finally, the initial conditions for the drug release experiments are:

$$C(y,t=0)=C_i$$

$$C_w(t=0)=0 \quad (15)$$

For fluid volumes that are much larger than lens volumes and where the solubility of timolol, fluzonazole and DXP is very high in PBS at this pH 7.4, perfect sink conditions are satisfied. Even though the solubility of DX is not as high as timolol in PBS, the release of DX establishes a perfect sink condition for short initial times. Under perfect sink conditions, the set of equations listed above can be solved analytically to give the following solution for the concentration profile in the lens:

$$C = \sum_{n=0}^{\infty} \frac{(-1)^n 4 C_i}{(2n+1)\pi} \cos\left(\frac{(2n+1)\pi}{2h(x)} y\right) e^{-\frac{(2n+1)^2 \pi^2}{4h(x)^2} Dt} \quad (16)$$

In the short time limit, the concentration profile can be expressed as:

$$C = \frac{2}{\sqrt{\pi}} C_i \int_0^{\frac{h-y}{\sqrt{4Dt}}} e^{-\eta^2} d\eta \quad (17)$$

for times shorter than the $h(x)/\sqrt{4Dt}$. By using equation (14) and equation (17), one obtains the following:

$$V_w \frac{dC_w}{dt} = 2D \frac{2}{\sqrt{\pi}} \frac{C_i}{\sqrt{4Dt}} \int_0^S P(x)dx = D \frac{2}{\sqrt{\pi}} \frac{C_i}{\sqrt{4Dt}} A_{surface} \quad (18)$$

where $A_{surface}$ is the total surface area of the lens. The equation (14) can be integrated to give, $$C_w = \frac{2\sqrt{Dt}}{\sqrt{\pi}} C_i \frac{A_{surface}}{V_w} \quad (19)$$

The fractional release $$f \equiv \frac{V_w C_w}{V_{gel} C_i}$$

can be expressed as $$f = \frac{2\sqrt{Dt}}{\sqrt{\pi}} \frac{A_{surface}}{V_{gel}} = \frac{2}{\sqrt{\pi}} \sqrt{\frac{Dt}{\bar{h}^2}} \quad (20)$$

where $\bar{h}$ is the mean thickness of the lens defined as $$\bar{h} \equiv \frac{V_{gel}}{A_{surface}}.$$

The above equation is only valid for times shorter than $h_{min}/\sqrt{4Dt}$, where $h_{min}$ is the minimum lens thickness, which typically equals the center thickness for negative power contact lenses.

Figure 31:
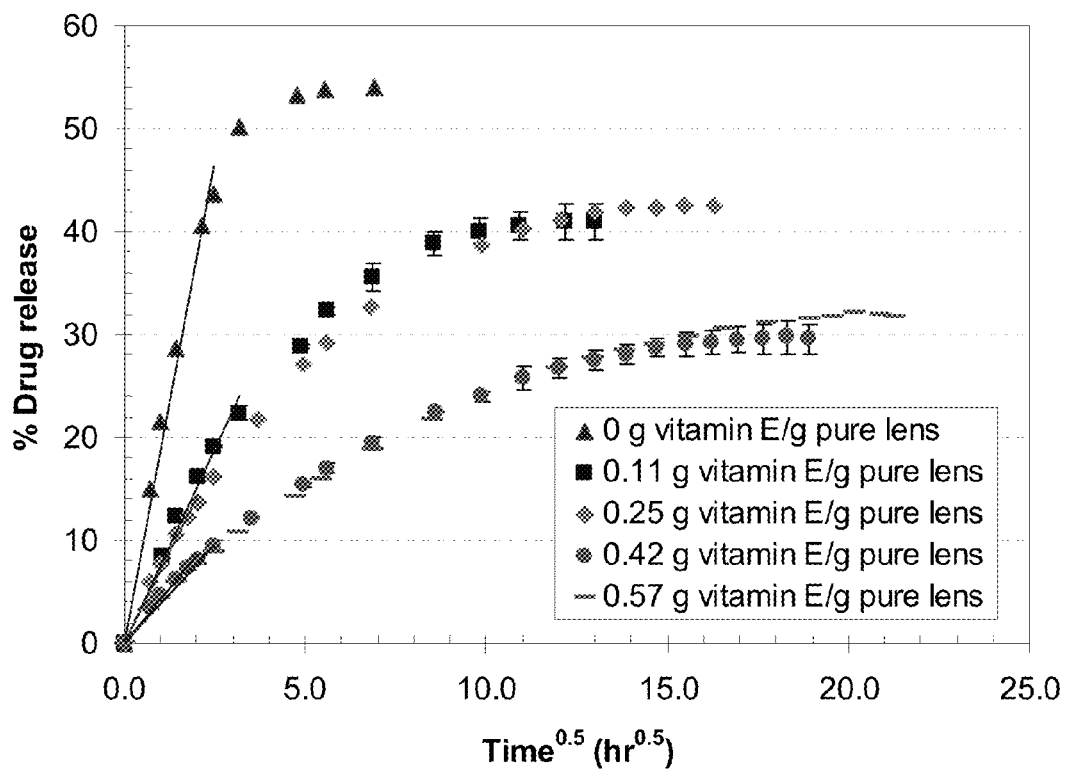
Figure 31:
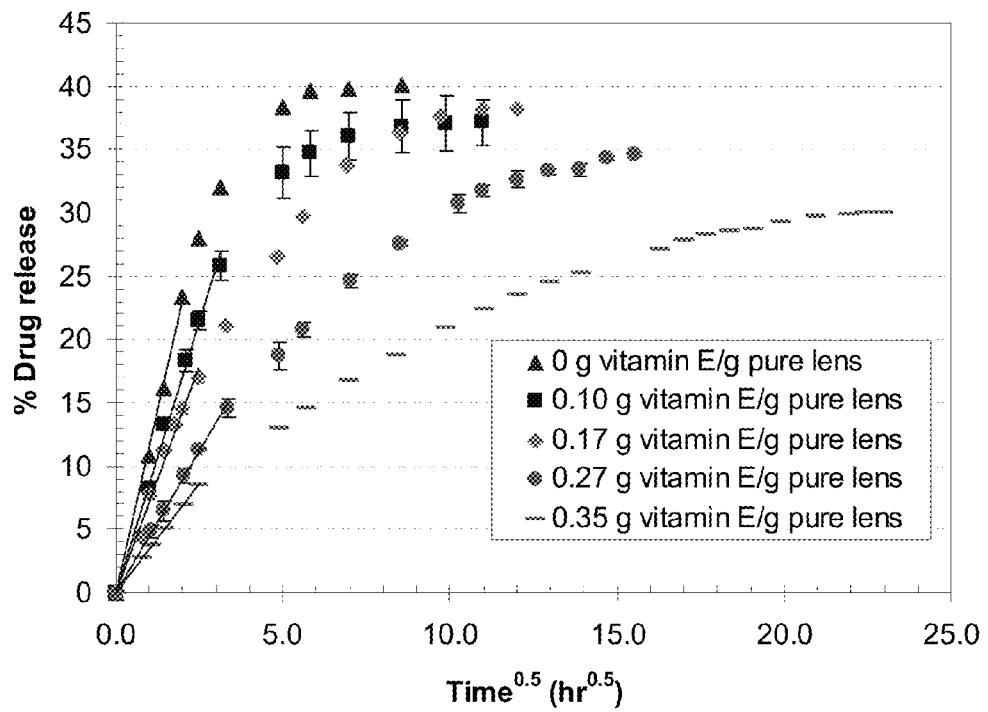
Figure 31:
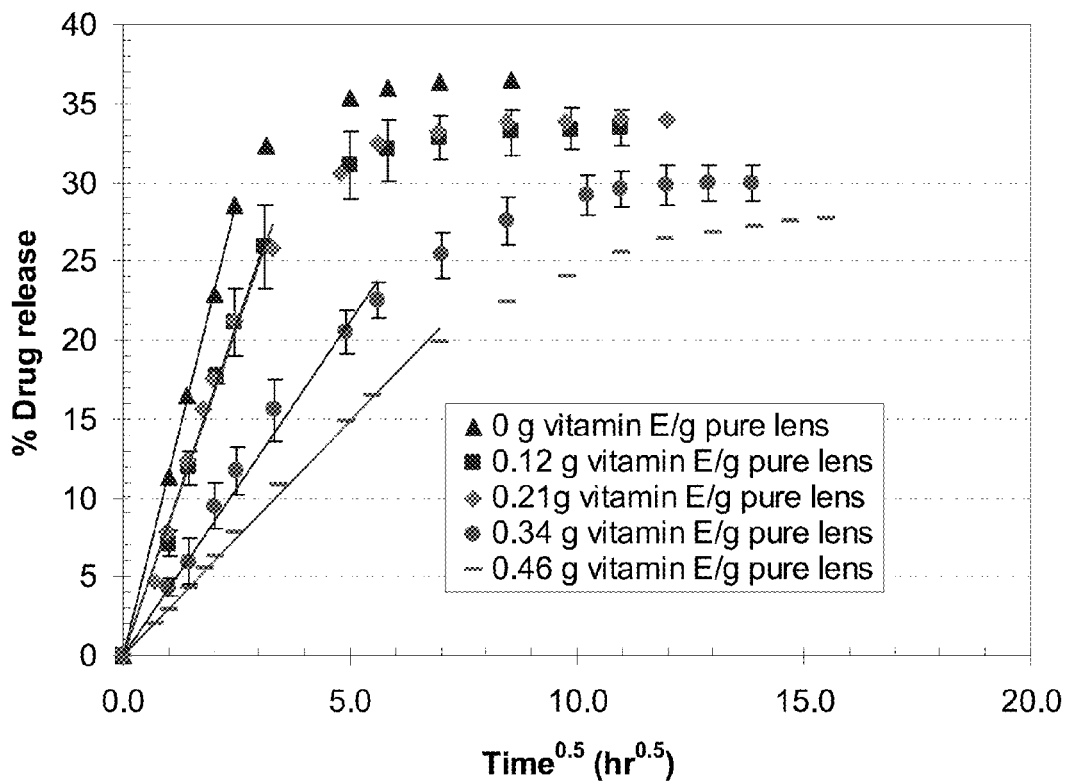
Figure 31:
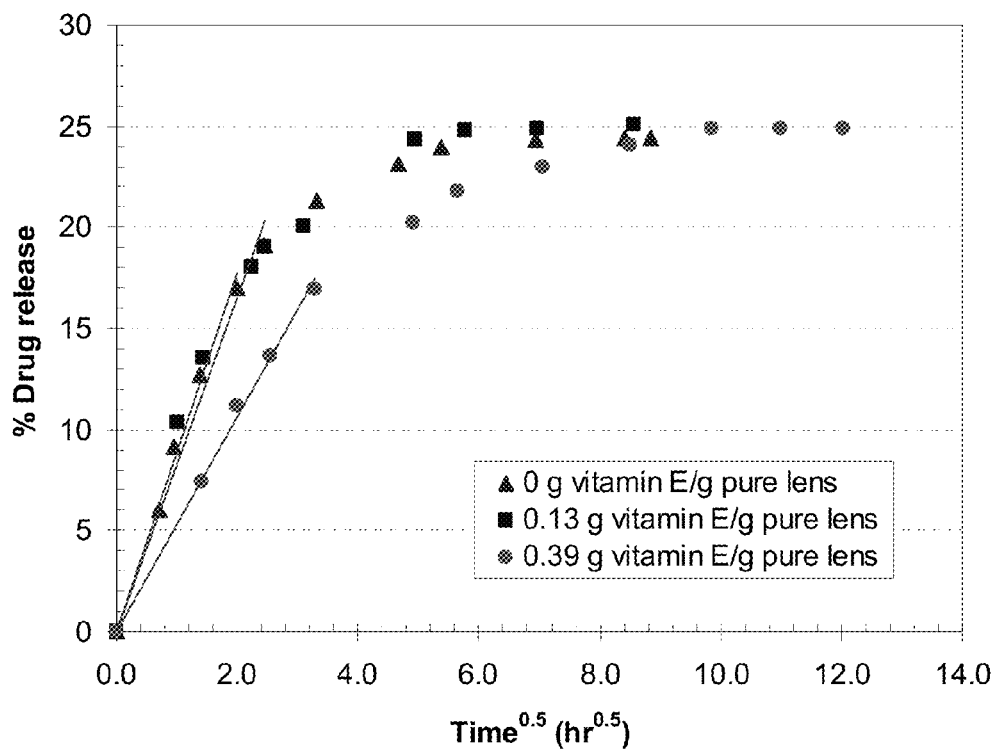
Figure 31:
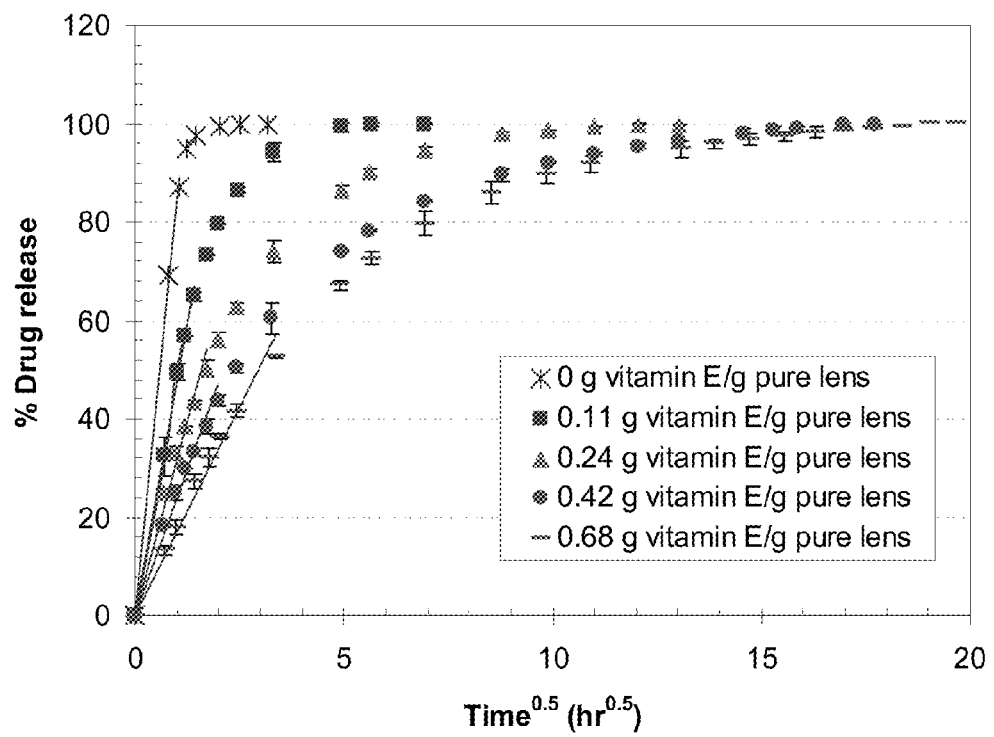
Figure 31:
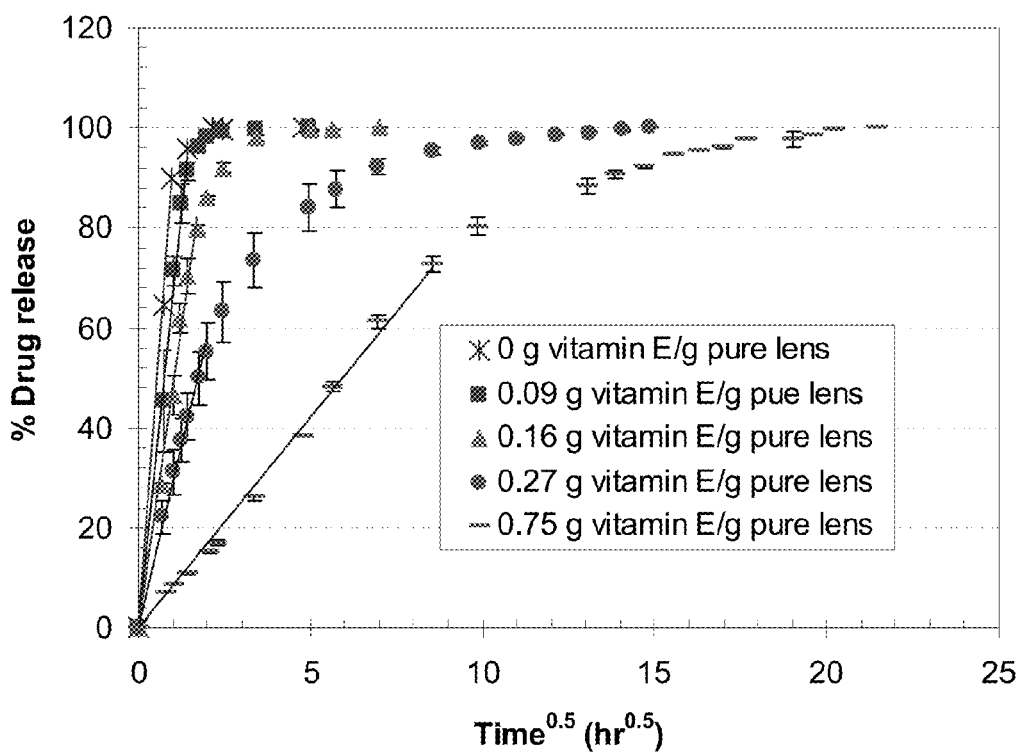
Figure 31:
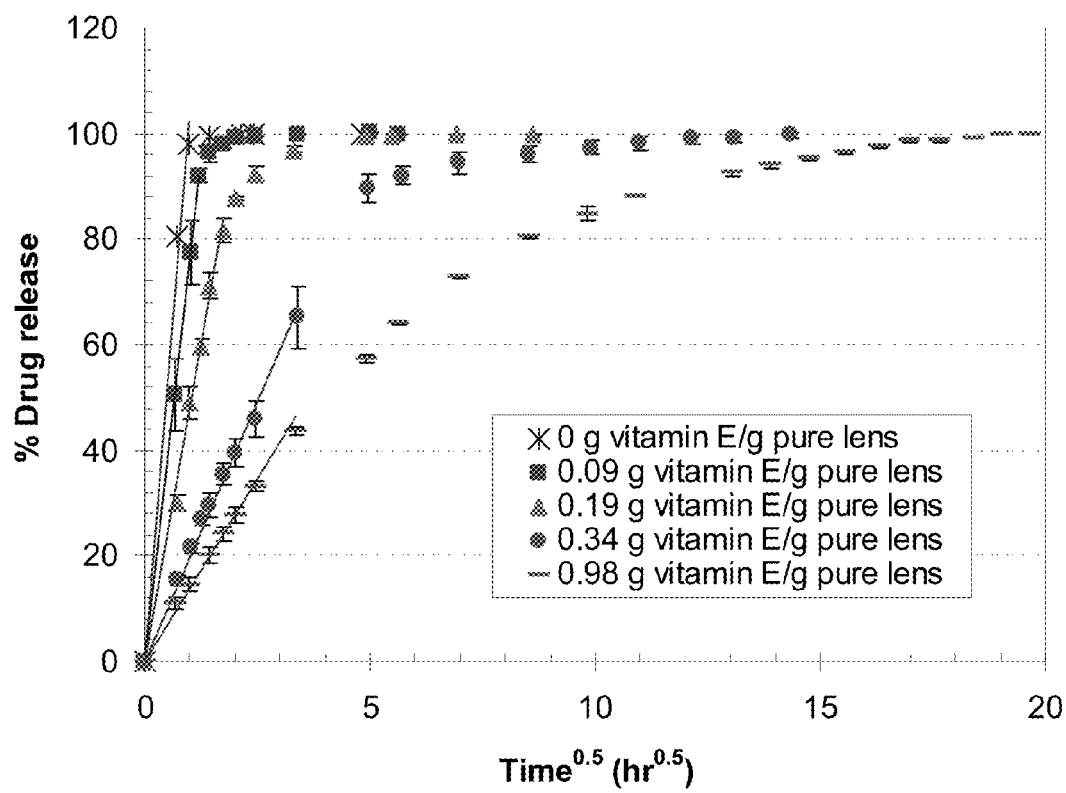
Figure 31:
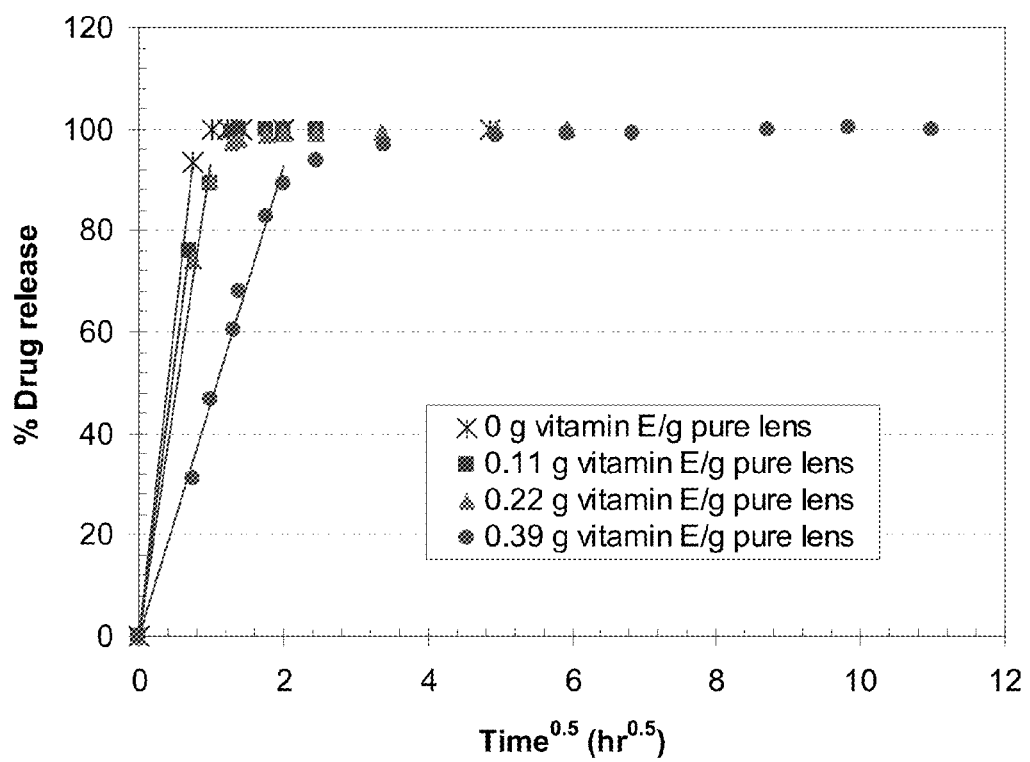
Figure 31:
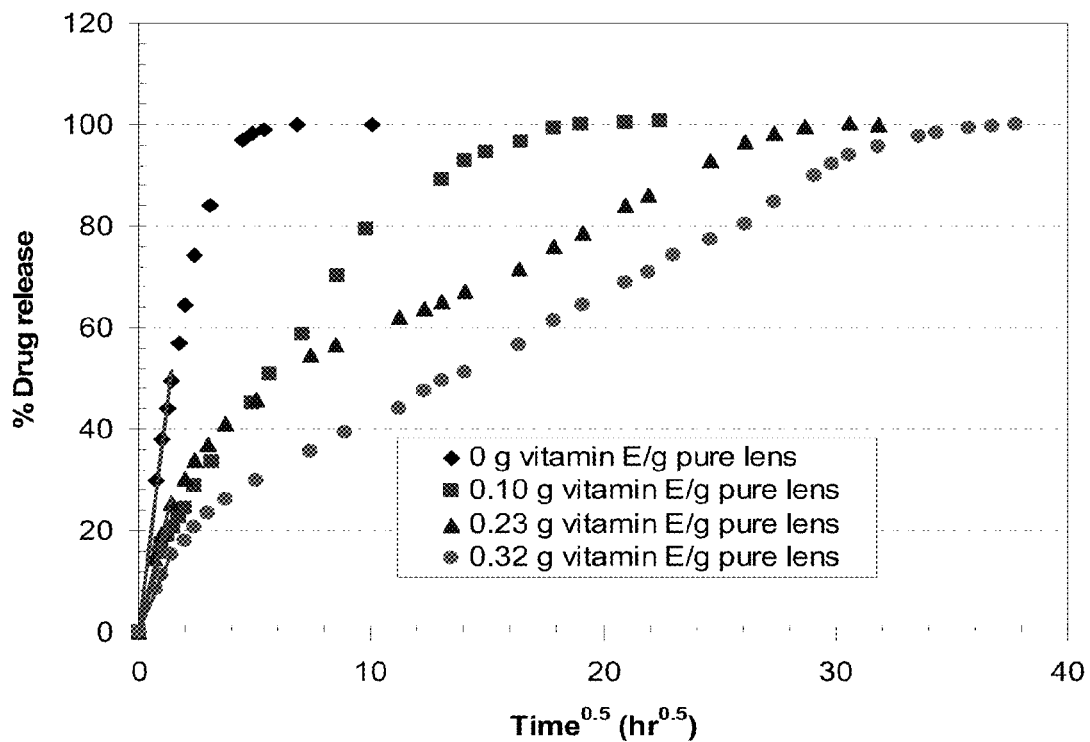
Figure 31:
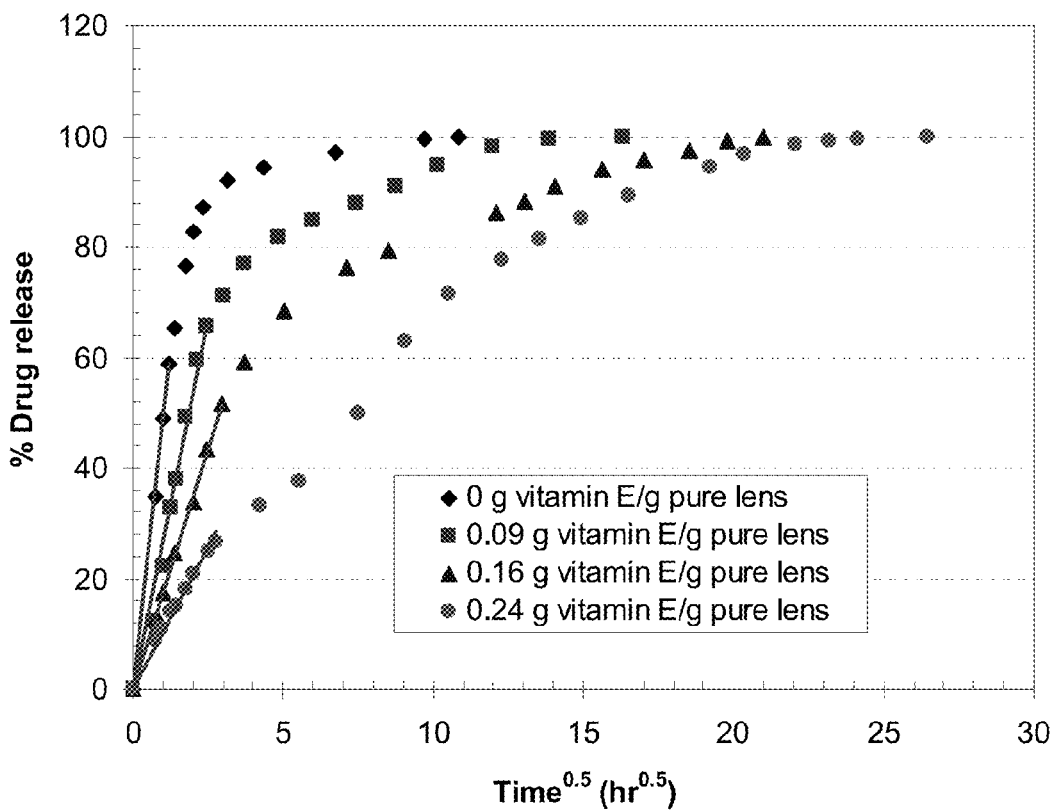
Figure 31:
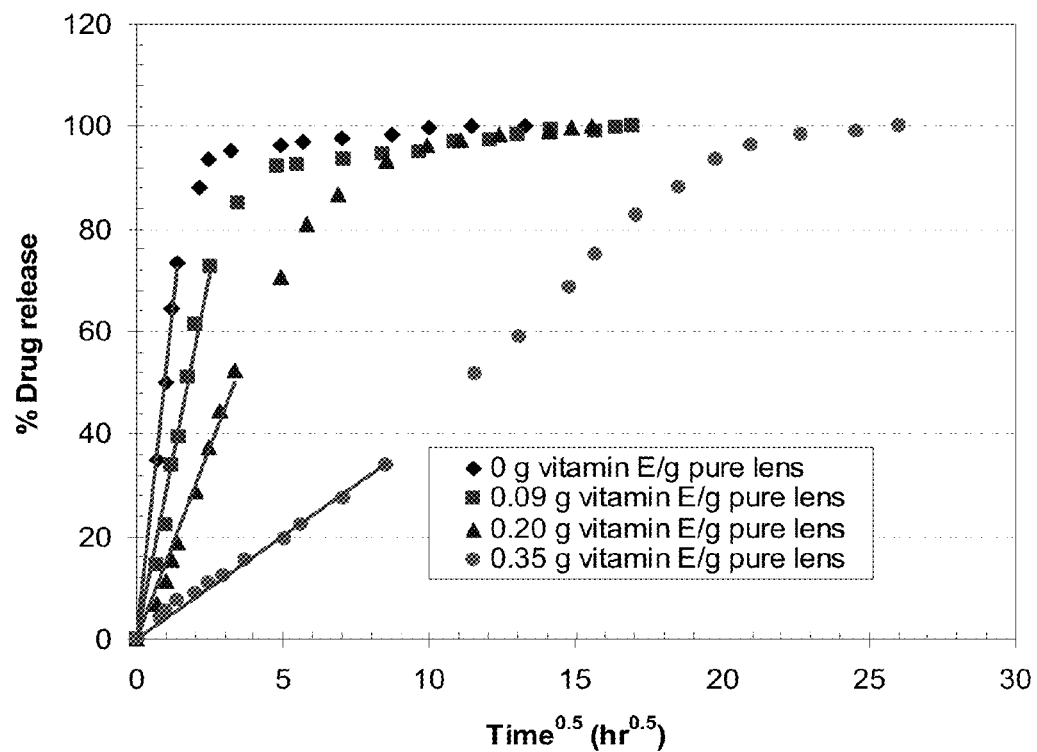
Figure 31:
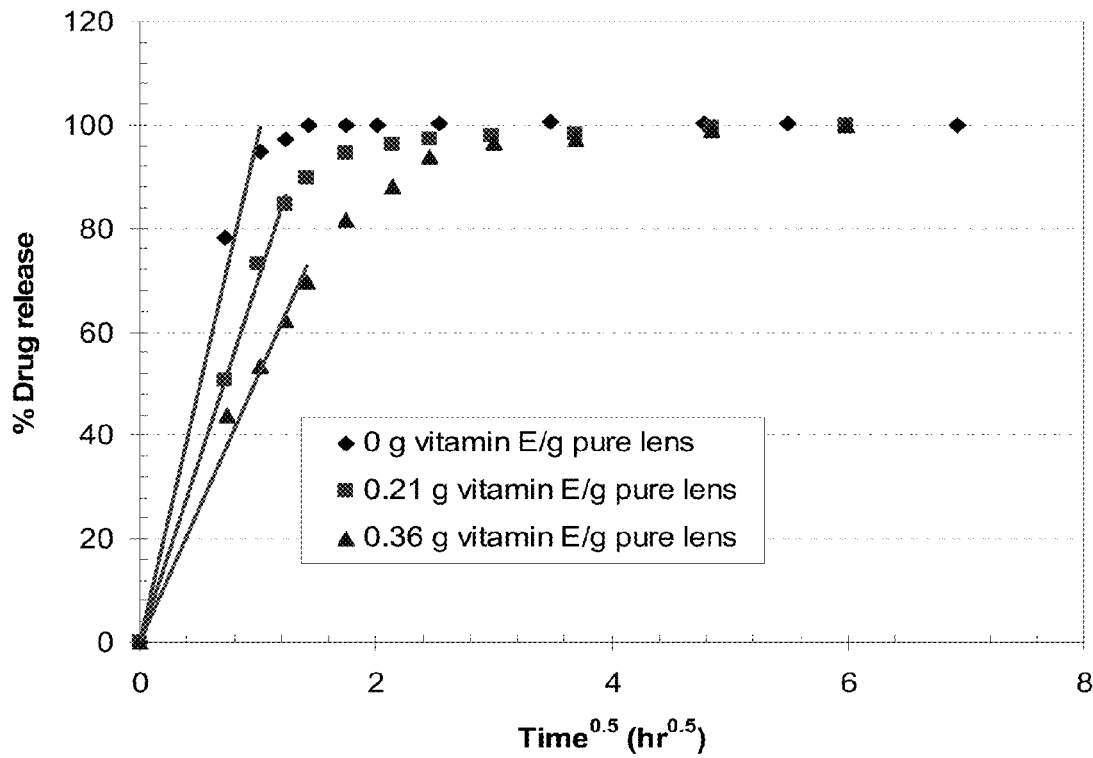
Figure 31:
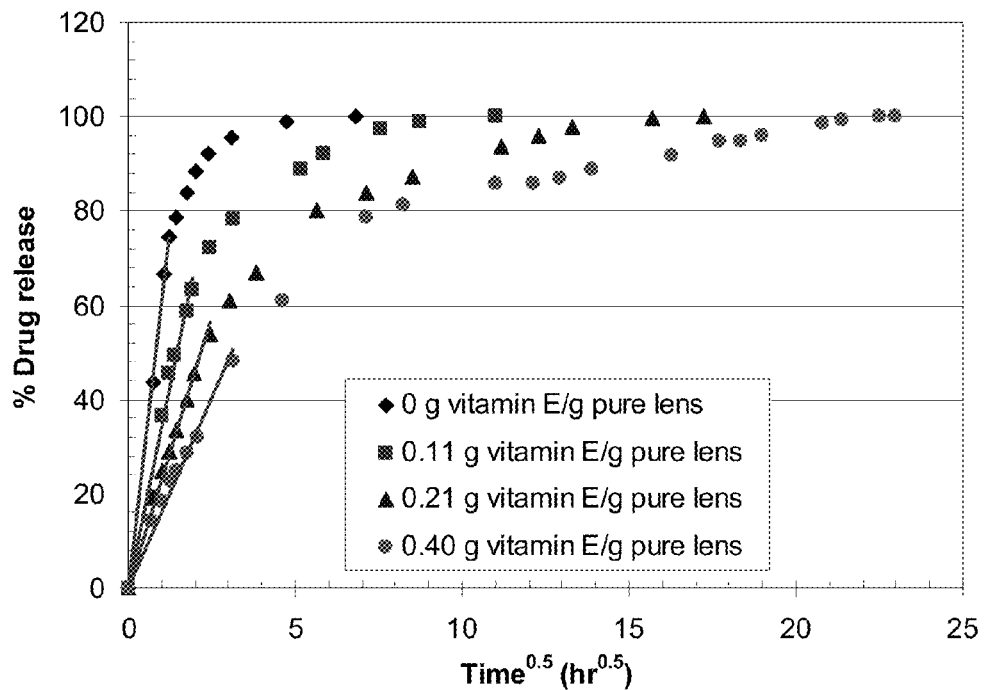
Figure 31:
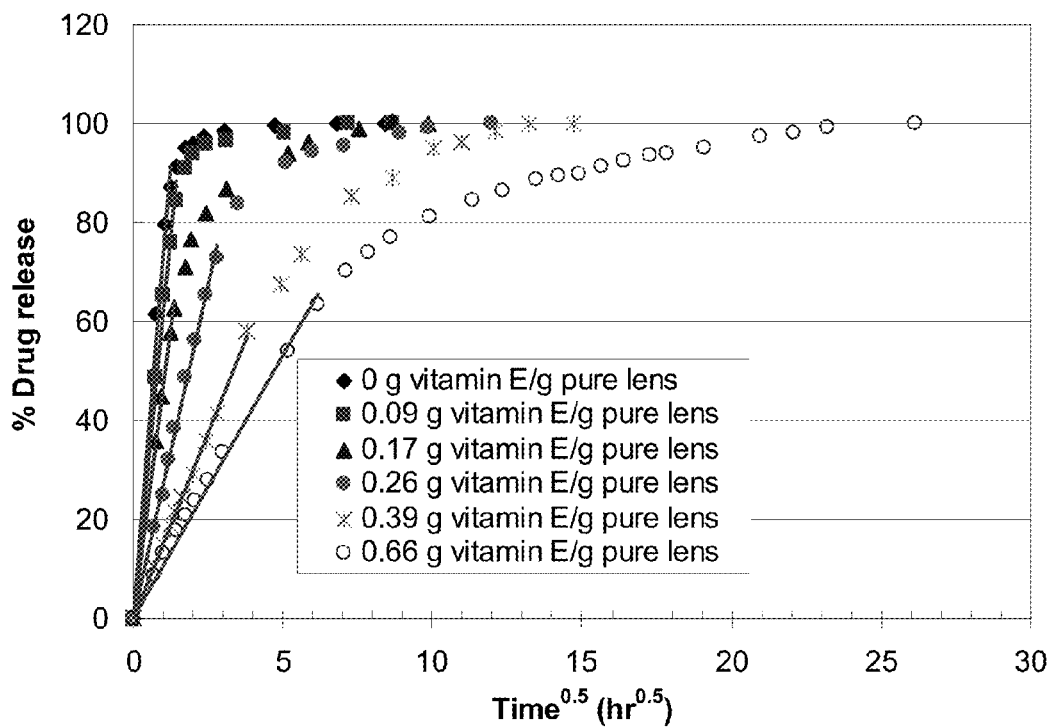
Figure 31:
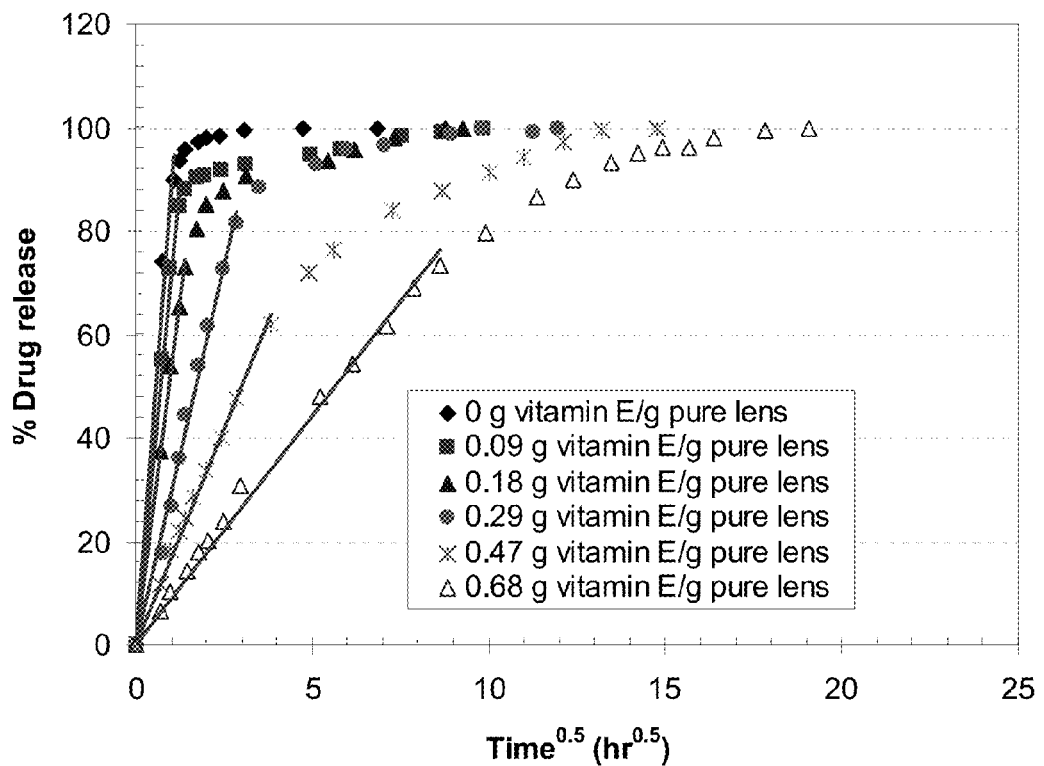
Figure 32A:
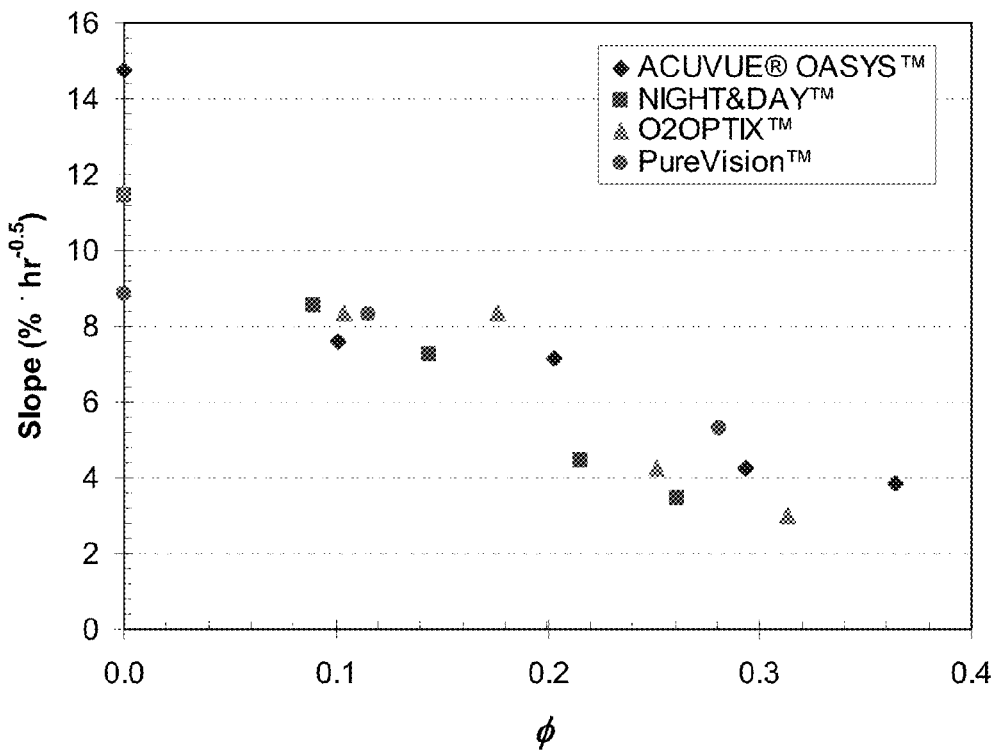
Figure 32B:
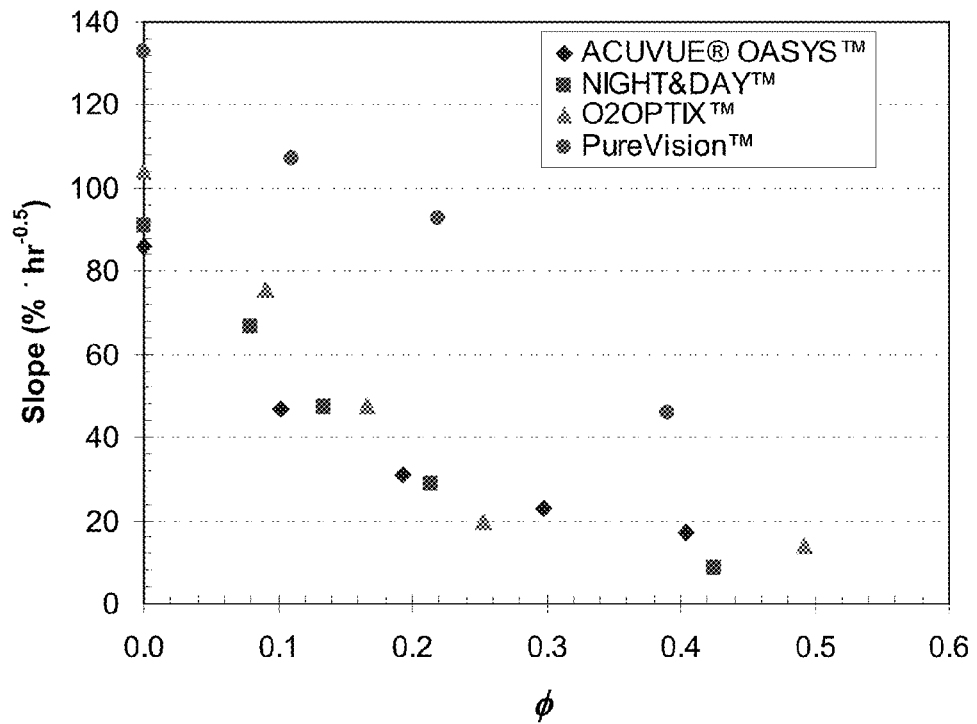
Figure 32C:
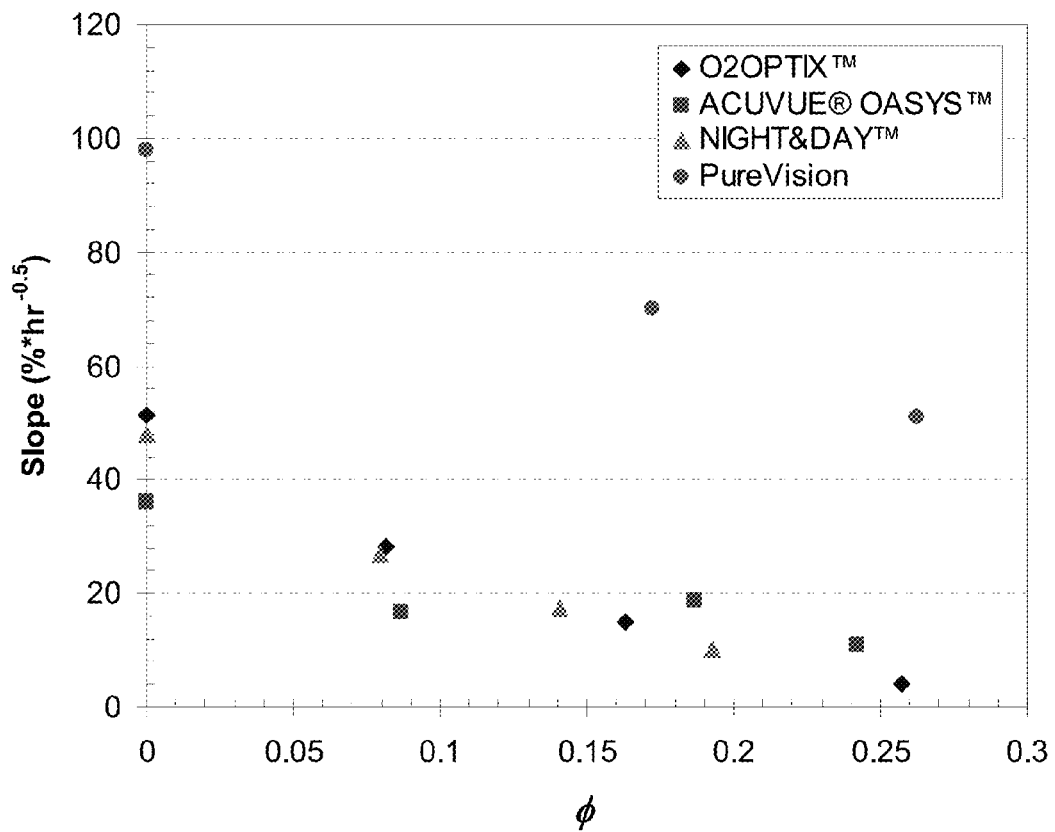
Figure 32D:
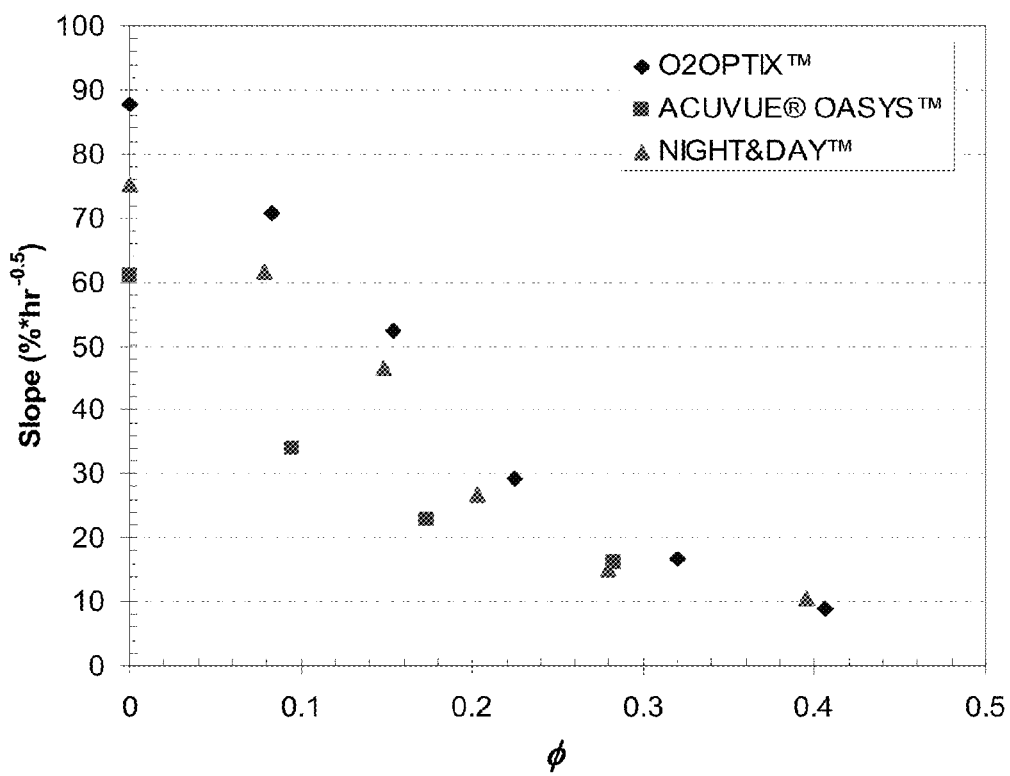

FIG. 31 plots % drugs release by Vitamin E loaded lenses as a function of the square root of time, for DX, timolol, fluzonazole and DXP. The lines of FIG. 31 are best fit straight lines over short time release data having $R^2$ larger than 0.98. All of the data for the initial hours fit the straight line well, which suggest that the transport of these drugs in the Vitamin E loaded lens may be diffusion controlled, although comparison of release profiles by different thickness lens would be needed to confirm that transport is diffusion controlled. The straight lines can be expressed by the equation:

$$\frac{M_t}{M_\infty}(\%) = \frac{2}{\sqrt{\pi}} \sqrt{\frac{Dt}{\bar{h}^2}} \times 100 \quad (21)$$

where $M_t$ is the mass of drug released at time t, $M_\infty$ the mass of drug release as time approaches infinity and for perfect sink condition $M_\infty = M_0$ (initial drug loading). Therefore, from the slope of the straight line in FIG. 31, diffusivities of drug in the Vitamin E loaded lens can be determined if the mean lens thickness is known. The slope for DX, timolol, fluzonazole and DXP release is plotted versus Vitamin E loading in FIG. 32A-D. The slope decreases as Vitamin E loading increases for all lenses for all drugs release, which means $(\sqrt{D}/h)$ decreases. For example, DX release by $O_2$OPTIX lens with 34% Vitamin E loading shows slope of about 37% of the slope for pure lens. The h also increases as Vitamin E loading increases and lens expands symmetrically for all expansion axes (isotropic expansion) as described above. The increase of h might be 6.8% for hydrated $O_2$OPTIX lens with 34% Vitamin E loading from FIG. 5B. Consequently, $\sqrt{D}$ is 39.5% of that of pure lens, i.e., D of DX in the 34% Vitamin E loaded $O_2$OPTIX lens is 15% of that of the vitamin free (pure) lens. In the same manner, D of timolol in the 34% Vitamin E loaded $O_2$OPTIX lens is 4% of that in the Vitamin E free (pure) lens. The ratios of diffusivities of DX (or timolol) in Vitamin E loaded lens to Vitamin E free (pure) lens $D/D_0$ for the other lenses are computed in the same manner and are listed in Table 9, below. In Table 9, the values of $D/D_0$ for timolol loaded lenses are smaller than those with DX for comparable Vitamin E loadings. In addition, it is noted that $\sqrt{D_0}$ of timolol is larger than that of DX by an order of magnitude, i.e., $D_0$ of timolol is larger by a factor of about 3, the effect of decrease on diffusivity is much larger for timolol.

TABLE 9

Ratio of diffusivities of drug in Vitamin E loaded lens to pure lens ($D/D_0$).

| Contact lenses | Vitamin E loading [g Vitamin E/ g pure lens] | $D/D_0$ DX | Timolol |
|---|---|---|---|
| ACUVUE ® OASYS ™ | 0.00 | 1.00 | 1.00 |
| | 0.11 | 0.28 | 0.31 |
| | 0.24 | 0.25 | 0.14 |
| | 0.42 | 0.09 | 0.08 |
| | 0.57 | 0.08 | — |
| | 0.68 | — | 0.05 |
| NIGHT&DAY ™ | 0.00 | 1.00 | 1.00 |
| | 0.09 | — | 0.55 |
| | 0.10 | 0.57 | — |
| | 0.16 | 0.43 | 0.29 |
| | 0.27 | 0.17 | 0.11 |
| | 0.35 | 0.11 | — |
| | 0.74 | — | 0.01 |
| $O_2$OPTIX ™ | 0.00 | 1.00 | 1.00 |
| | 0.10 | — | 0.56 |
| | 0.12 | 0.55 | — |
| | 0.20 | 0.58 | 0.24 |
| | 0.34 | 0.15 | 0.04 |
| | 0.46 | 0.08 | — |
| | 0.97 | — | 0.03 |
| PureVision ™ | 0.00 | 1.00 | 1.00 |
| | 0.11 | — | 0.67 |
| | 0.13 | 0.91 | — |
| | 0.22 | — | 0.53 |
| | 0.39 | 0.64 | 0.14 |

For two systems with identical geometries but with different diffusivities, the profiles for fractional drug release versus the product of diffusivity and time are identical. Thus if the introduction of Vitamin E leads to a uniform decrease in diffusivity everywhere in the hydrogel, the fractional release curves with and without Vitamin E are expected to overlap when plotted against Dt. However, introduction of Vitamin E leads to an increase in hydrogel thickness and there is no exact scaling to account for this increase. However, the increase can be approximated by plotting the release fraction against $$\frac{D}{D_0}\frac{h_0^2}{h^2}t.$$

These plots are shown in FIG. 33 for timolol release from the ACUVUE® OASYS™ and NIGHT&DAY™, which have the largest effect of Vitamin E uptake on timolol diffusivity. The release curves do not overlap for both lens types. This suggests that the diffusivity in Vitamin E laden hydrogels of these two types is position dependent with smaller diffusivities near the center of the hydrogel, possibly due to a higher concentration of Vitamin E in the hydrogel center. A non uniform distribution of Vitamin E is possible because during the process of ethanol evaporation, Vitamin E may diffuse towards the center as ethanol evaporates. The dependence of diffusivity on position causes the $\tau/\tau_0$ shown in FIG. 33A to be much greater than $D/D_0$ shown in FIG. 34.

FIG. 35 plots % drug release by silicone contact lens as function of square root of time for CyA. The best fit straight lines are also shown in the figure. The straight lines fit the data well with $R^2$ values larger than 0.96, showing that the drug transport in these lenses is diffusion controlled. The slope is clearly larger for ACUVUE® OASYS™ showing the drug diffusivity is highest for these lenses amongst those explored here. Equation (21) is not strictly valid because the system did not reach equilibrium during loading, however the short time data should still satisfy Equation (21) since the concentration in the region of the lens close to the surface was near equilibrium concentration.

The CyA % release by Vitamin E loaded ACUVUE® OASYS™ versus square root of time and the best fit straight lines for short time release were also plotted in FIG. 36. All the $R^2$ values of the fitting results for these ACUVUE® OASYS™ lenses with various Vitamin E loaded lens are about 0.99, suggesting that the CyA delivery by these Vitamin E loaded silicone hydrogel lenses are controlled by diffusion transport as well. Since CyA is a hydrophobic drug with high partition coefficient in Vitamin E phase, the inclusive CyA in the lens can partition into the Vitamin E aggregates inside the contact lens when diffuses through out the entire gel matrix into PBS medium. Therefore, the effect of attenuating the drug release rate by loading Vitamin E into the contact lens could result from the difference of drug diffusivity between silicone gel matrix region and Vitamin E aggregates, which is similar to the mechanism of extended release of hydrophobic dexamethasone by the same systems. The comparison of CyA and dexamethasone delivery duration increase by Vitamin E loaded ACUVUE® OASYS™ are plotted in FIG. 37, suggesting that Vitamin E has similar effect on slowing the drug delivery of both drugs.

Example 18

Preparation of a HEMA Gel with Surfactant and Vitamin E

HEMA gels loaded with both surfactant and Vitamin E were prepared by adding Vitamin E and surfactant (8% loading by weight in dry lens). On soaking these lenses in PBS, vitamin diffuses out along with the surfactant. This sharply contrasts the case without surfactant in which the Vitamin E does not diffuse out due to very limited solubility of Vitamin E in PBS.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An appliance for delivery of a bioactive agent comprising:
   a silicone-hydrogel lens;
   a diffusion attenuator consisting of Vitamin E within said lens; and
   at least one bioactive agent.

2. The appliance of claim 1, wherein said bioactive agent comprises a drug or a nutraceutical.

3. The appliance of claim 1, wherein said bioactive agent is selected from the group consisting of timolol, pilocarpine, latanoprost, dexamethasone, prednisilone, cyclosporine, ciprofloxacin, ciloxan, gentamycin, ketotifen, ivermectin, pyrimethamine, Vitamin B-1, Vitamin B-2, Vitamin B-3, Vitamin B-5, panthenol, pantothenic acid, Vitamin B-6, Vitamin B-8, Vitamin B-9, Vitamin B-12, Cobalamin, Folic Acid, Biotin, Choline Inositol, Para Amino Benzoic Acid, Ascorbic Acid, Vitamin C, Beta Carotene, Vitamin D, Copper salts, Chromium salts, Iodine salts, Iron salts, Manganese salts, Magnesium salts, Molybdenum salts, Phosphorous salts, Potassium salts, Sodium salts, Selenium salts, and Zinc salts.

4. The appliance of claim 1, further comprising a second diffusion attenuator comprising Vitamin A, a silicone oil, or a hydrocarbon oil.

5. The appliance of claim 1, further comprising a surface active agent.

6. A method of preparation for a contact lens for delivery of a bioactive agent comprising the steps of:
   providing a silicone-hydrogel lens;
   soaking said lens in a first solution comprising a diffusion attenuator consisting of Vitamin E;
   soaking said lens in a second solution comprising at least one bioactive agent; and
   removing one or more solvents.

7. The method of claim 6, wherein said solvent comprise a non-aqueous solvent.

8. The method of claim 7, wherein said solvent comprises ethanol.

9. The method of claim 6, wherein said solvent is an aqueous solvent.

10. The method of claim 6, wherein said bioactive agent is selected from the group consisting of timolol, pilocarpine, latanoprost, dexamethasone, prednisilone, cyclosporine, ciprofloxacin, ciloxan, gentamycin, ketotifen, ivermectin, pyrimethamine, Vitamin B-1, Vitamin B-2, Vitamin B-3, Vitamin B-5, panthenol, pantothenic acid, Vitamin B-6, Vitamin B-8, Vitamin B-9, Vitamin B-12, Cobalamin, Folic Acid, Biotin, Choline Inositol, Para Amino Benzoic Acid, Ascorbic Acid, Vitamin C, Beta Carotene, Vitamin D, Copper salts, Chromium salts, Iodine salts, Iron salts, Manganese salts, Magnesium salts, Molybdenum salts, Phosphorous salts, Potassium salts, Sodium salts, Selenium salts, and Zinc salts.

11. The method of claim 6, wherein said first solution further comprises a second diffusion attenuator comprising Vitamin A, a silicone oil, or a hydrocarbon oil.

12. The method of claim 6, further comprising a surface active agent.

13. A method of delivery of a bioactive agent to an eye comprising the steps of:

providing a silicon-hydrogel contact lens containing a diffusion attenuator consisting of Vitamin E and at least one bioactive agent; and placing said lens in an eye, wherein said lens delivers said bioactive agent for a period of time of at least 8 hours.

14. The method of claim 13, wherein said bioactive agent comprises a drug or a nutraceutical.

15. The method of claim 13, wherein said bioactive agent is selected from the group consisting of timolol, pilocarpine, latanoprost, dexamethasone, prednisilone, cyclosporine, ciprofloxacin, ciloxan, gentamycin, ketotifen, ivermectin, pyrimethamine, Vitamin B-1, Vitamin B-2, Vitamin B-3, Vitamin B-5, panthenol, pantothenic acid, Vitamin B-6, Vitamin B-8, Vitamin B-9, Vitamin B-12, Cobalamin, Folic Acid, Biotin, Choline Inositol, Para Amino Benzoic Acid, Ascorbic Acid, Vitamin C, Beta Carotene, Vitamin D, Copper salts, Chromium salts, Iodine salts, Iron salts, Manganese salts, Magnesium salts, Molybdenum salts, Phosphorous salts, Potassium salts, Sodium salts, Selenium salts, and Zinc salts.

16. The method of claim 13, further comprising a second diffusion attenuator comprising Vitamin A, a silicone oil, or a hydrocarbon oil.

17. The method of claim 13, further comprising a surface active agent.

* * * * *

UNITED STATES PATENT AND TRADEMARK OFFICE
CERTIFICATE OF CORRECTION

PATENT NO. : 8,404,265 B2
APPLICATION NO. : 12/841504
DATED : March 26, 2013
INVENTOR(S) : Anuj Chauhan and Jinah Kim It is certified that error appears in the above-identified patent and that said Letters Patent is hereby corrected as shown below:

In the Specifications:

Column 1,
Line 37, "$1^2/D$" should read --$l^2/D$--.

Column 3,
Line 47, "($M_4$)" should read --($M_f$)--.

Column 4,
Line 20, "dexamthasone" should read --dexamethasone--.
Lines 22-23, "dexamthasone" should read --dexamethasone--.
Line 25, "dexamthasone" should read --dexamethasone--.
Lines 27-28, "dexamthasone" should read --dexamethasone--.
Line 31, "dexamthasone" should read --dexamethasone--.
Lines 33-34, "dexamthasone" should read --dexamethasone--.
Line 48, "shows plots" should read --show plots--.
Line 56, "shows plots" should read --show plots--.

Column 5,
Line 4, "shows plots" should read --show plots--.
Line 11, "shows plots" should read --show plots--.
Line 18, "shows plots" should read --show plots--.
Line 25, "shows plots" should read --show plots--.
Line 32, "shows plots" should read --show plots--.
Line 39, "shows plots" should read --show plots--.
Line 44, "shows plots" should read --show plots--.
Line 53, "shows plots" should read --show plots--.
Line 58, "shows plots" should read --show plots--.

Signed and Sealed this
Twentieth Day of August, 2013

Teresa Stanek Rea
*Acting Director of the United States Patent and Trademark Office*

Column 31,
Line 6, "time r" should read --time τ--.
Line 64, "for the gydrogel" should read --for the hydrogel--.

Column 33,
Line 5,

" $$C = \frac{2}{\sqrt{\pi}} C_i \int_0^{\frac{h-y}{\sqrt{4Dt}}} e^{-\eta^2} d\eta$$ " should read -- $$C = \frac{2}{\sqrt{\pi}} C_i \int_0^{\frac{h-y}{\sqrt{4Dt}}} e^{-\eta^2} d\eta$$ --.

In the Claims:

Column 36,
Line 43, "solvent comprise" should read --solvent comprises--.